US008641711B2

(12) United States Patent
Kelly et al.

(10) Patent No.: US 8,641,711 B2
(45) Date of Patent: Feb. 4, 2014

(54) METHOD AND APPARATUS FOR GASTROINTESTINAL TRACT ABLATION FOR TREATMENT OF OBESITY

(75) Inventors: Douglas Kelly, Palo Alto, CA (US); David S. Utley, Redwood City, CA (US); Robert A. Ganz, Minnetonka, MN (US); Michael P. Wallace, Pleasanton, CA (US); Nathan Every, Seattle, WA (US)

(73) Assignee: Covidien LP, Mansfield, MA (US)

( * ) Notice: Subject to any disclaimer, the term of this patent is extended or adjusted under 35 U.S.C. 154(b) by 1643 days.

(21) Appl. No.: 12/114,628

(22) Filed: May 2, 2008

(65) Prior Publication Data

US 2008/0275445 A1 Nov. 6, 2008

Related U.S. Application Data

(60) Provisional application No. 60/916,248, filed on May 4, 2007, provisional application No. 60/958,543, filed on Jul. 6, 2007, provisional application No. 60/958,562, filed on Jul. 6, 2007.

(51) Int. Cl.
*A61B 18/18* (2006.01)

(52) U.S. Cl.
USPC .............................. 606/45; 606/41

(58) Field of Classification Search
USPC ....................................... 606/41–45
See application file for complete search history.

(56) References Cited

U.S. PATENT DOCUMENTS

| 552,832 A | 1/1896 | Fort |
| 1,798,902 A | 3/1931 | Raney |
| 3,517,128 A | 6/1970 | Hines |
| 3,901,241 A | 8/1975 | Allen, Jr. |
| 3,924,628 A | 12/1975 | Droegemueller et al. |
| 4,011,872 A | 3/1977 | Komiya |
| 4,196,724 A | 4/1980 | Wirt et al. |

(Continued)

FOREIGN PATENT DOCUMENTS

| DE | 3838840 | 5/1990 |
| DE | 4303882 | 8/1994 |

(Continued)

OTHER PUBLICATIONS

Wallace et al.; U.S. Appl. No. 13/051,738 entitled "Selectively expandable operative element support structure and methods of use," filed Mar. 18, 2011.

(Continued)

*Primary Examiner* — Linda Dvorak
*Assistant Examiner* — Amanda Scott
(74) *Attorney, Agent, or Firm* — Holland & Hart LLP

(57) ABSTRACT

Devices and methods for ablating tissue in the wall of various organs of the gastrointestinal tract of a patient in order to cure or ameliorate metabolic pathophysiological conditions such as obesity, insulin resistance, or type 2 diabetes mellitus are provided. Ablational treatment of target areas may be fractional or partial, rendering a post-treatment portion of target tissue ablated and another portion that is substantially intact. Fractional ablation is achieved by controlling the delivery of ablational energy across the surface area being treated, and controlling the depth of energy penetration into tissue. Surface area control of energy delivery may controlled by the spatial pattern of distributed ablation elements or by the selective activation of a subset of a dense pattern of ablation elements. Embodiments of the device include an ablational electrode array that spans 360 degrees and an array that spans an arc of less than 360 degrees.

48 Claims, 37 Drawing Sheets

(56) References Cited

U.S. PATENT DOCUMENTS

| | | | |
|---|---|---|---|
| 4,304,239 | A | 12/1981 | Perlin |
| 4,311,154 | A | 1/1982 | Sterzer et al. |
| 4,407,298 | A | 10/1983 | Lentz et al. |
| 4,411,266 | A | 10/1983 | Cosman |
| 4,423,812 | A | 1/1984 | Sato |
| 4,532,924 | A | 8/1985 | Auth et al. |
| 4,565,200 | A | 1/1986 | Cosman |
| 4,640,298 | A | 2/1987 | Pless et al. |
| 4,658,836 | A | 4/1987 | Turner |
| 4,662,383 | A | 5/1987 | Sogawa et al. |
| 4,674,481 | A | 6/1987 | Boddie, Jr. et al. |
| 4,676,258 | A | 6/1987 | Inokuchi et al. |
| 4,705,041 | A | 11/1987 | Kim |
| 4,709,698 | A | 12/1987 | Johnston et al. |
| 4,740,207 | A | 4/1988 | Kreamer |
| 4,765,331 | A | 8/1988 | Petruzzi et al. |
| 4,776,349 | A | 10/1988 | Nashef et al. |
| 4,860,744 | A | 8/1989 | Johnson et al. |
| 4,887,614 | A | 12/1989 | Shirakami et al. |
| 4,895,138 | A | 1/1990 | Yabe |
| 4,901,737 | A | 2/1990 | Toone |
| 4,906,203 | A | 3/1990 | Margrave et al. |
| 4,907,589 | A | 3/1990 | Cosman |
| 4,930,521 | A | 6/1990 | Metzger et al. |
| 4,943,290 | A | 7/1990 | Rexroth et al. |
| 4,947,842 | A | 8/1990 | Marchosky et al. |
| 4,949,147 | A | 8/1990 | Bacuvier |
| 4,955,377 | A | 9/1990 | Lennox et al. |
| 4,966,597 | A | 10/1990 | Cosman |
| 4,969,890 | A | 11/1990 | Sugita et al. |
| 4,976,711 | A | 12/1990 | Parins et al. |
| 4,979,948 | A * | 12/1990 | Geddes et al. .................. 606/33 |
| 4,998,539 | A | 3/1991 | Delsanti |
| 5,006,119 | A | 4/1991 | Acker et al. |
| 5,010,895 | A | 4/1991 | Maurer et al. |
| 5,019,075 | A | 5/1991 | Spears et al. |
| 5,035,696 | A | 7/1991 | Rydell |
| 5,045,056 | A | 9/1991 | Behl |
| 5,046,512 | A | 9/1991 | Murchie |
| 5,047,028 | A | 9/1991 | Qian |
| 5,056,532 | A | 10/1991 | Hull et al. |
| 5,057,107 | A | 10/1991 | Parins et al. |
| 5,078,717 | A | 1/1992 | Parins et al. |
| 5,083,565 | A | 1/1992 | Parins |
| 5,084,044 | A | 1/1992 | Quint |
| 5,088,979 | A | 2/1992 | Filipi et al. |
| 5,094,233 | A | 3/1992 | Brennan |
| 5,100,423 | A | 3/1992 | Fearnot |
| 5,106,360 | A | 4/1992 | Ishiwara et al. |
| 5,117,828 | A | 6/1992 | Metzger et al. |
| 5,122,137 | A | 6/1992 | Lennox |
| 5,125,928 | A | 6/1992 | Parins et al. |
| 5,151,100 | A | 9/1992 | Abele et al. |
| 5,156,151 | A | 10/1992 | Imran |
| 5,163,938 | A | 11/1992 | Kambara et al. |
| 5,171,299 | A | 12/1992 | Heitzmann et al. |
| 5,190,541 | A | 3/1993 | Abele et al. |
| 5,192,297 | A | 3/1993 | Hull |
| 5,197,963 | A | 3/1993 | Parins |
| 5,197,964 | A | 3/1993 | Parins |
| 5,205,287 | A | 4/1993 | Erbel et al. |
| 5,215,103 | A | 6/1993 | Desai |
| 5,232,444 | A | 8/1993 | Just et al. |
| 5,236,413 | A | 8/1993 | Fiering |
| 5,242,441 | A | 9/1993 | Avitall |
| 5,254,126 | A | 10/1993 | Filipi et al. |
| 5,255,679 | A | 10/1993 | Imran |
| 5,256,138 | A | 10/1993 | Vurek et al. |
| 5,257,451 | A | 11/1993 | Edwards et al. |
| 5,257,635 | A | 11/1993 | Langberg |
| 5,263,493 | A | 11/1993 | Avitall |
| 5,275,162 | A | 1/1994 | Edwards et al. |
| 5,275,169 | A | 1/1994 | Afromowitz et al. |
| 5,275,608 | A | 1/1994 | Forman et al. |
| 5,275,610 | A | 1/1994 | Eberbach |
| 5,277,201 | A | 1/1994 | Stern |
| 5,281,216 | A | 1/1994 | Klicek |
| 5,281,217 | A | 1/1994 | Edwards et al. |
| 5,281,218 | A | 1/1994 | Imran |
| 5,290,286 | A | 3/1994 | Parins |
| 5,292,321 | A | 3/1994 | Lee |
| 5,293,869 | A | 3/1994 | Edwards et al. |
| 5,305,696 | A | 4/1994 | Mendenhall |
| 5,309,910 | A | 5/1994 | Edwards et al. |
| 5,313,943 | A | 5/1994 | Houser et al. |
| 5,314,438 | A | 5/1994 | Shturman |
| 5,314,466 | A | 5/1994 | Stern et al. |
| 5,316,020 | A | 5/1994 | Truffer |
| 5,324,284 | A | 6/1994 | Imran |
| 5,327,905 | A | 7/1994 | Avitall |
| 5,328,467 | A | 7/1994 | Edwards et al. |
| 5,334,196 | A | 8/1994 | Scott et al. |
| 5,336,222 | A | 8/1994 | Durgin, Jr. et al. |
| 5,345,936 | A | 9/1994 | Pomeranz et al. |
| 5,348,554 | A | 9/1994 | Imran et al. |
| 5,363,861 | A | 11/1994 | Edwards et al. |
| 5,365,926 | A | 11/1994 | Desai |
| 5,365,945 | A | 11/1994 | Halstrom |
| 5,366,490 | A | 11/1994 | Edwards et al. |
| 5,368,557 | A | 11/1994 | Nita et al. |
| 5,368,592 | A | 11/1994 | Stern et al. |
| 5,370,675 | A | 12/1994 | Edwards et al. |
| 5,370,678 | A | 12/1994 | Edwards et al. |
| 5,372,138 | A | 12/1994 | Crowley et al. |
| 5,375,594 | A | 12/1994 | Cueva |
| 5,383,874 | A | 1/1995 | Jackson et al. |
| 5,383,876 | A | 1/1995 | Nardella |
| 5,383,917 | A | 1/1995 | Desai et al. |
| 5,385,544 | A | 1/1995 | Edwards et al. |
| 5,397,339 | A | 3/1995 | Desai |
| 5,398,683 | A | 3/1995 | Edwards et al. |
| 5,401,272 | A | 3/1995 | Perkins |
| 5,403,311 | A | 4/1995 | Abele et al. |
| 5,409,453 | A | 4/1995 | Lundquist et al. |
| 5,409,483 | A | 4/1995 | Campbell et al. |
| 5,411,025 | A | 5/1995 | Webster, Jr. |
| 5,413,573 | A | 5/1995 | Koivukangas |
| 5,415,657 | A | 5/1995 | Taymor-Luria |
| 5,421,819 | A | 6/1995 | Edwards et al. |
| 5,423,808 | A | 6/1995 | Edwards et al. |
| 5,423,811 | A | 6/1995 | Imran et al. |
| 5,423,812 | A | 6/1995 | Ellman et al. |
| 5,425,704 | A | 6/1995 | Sakurai et al. |
| 5,428,658 | A | 6/1995 | Oettinger et al. |
| 5,433,739 | A | 7/1995 | Sluijter et al. |
| 5,435,805 | A | 7/1995 | Edwards |
| 5,441,499 | A | 8/1995 | Fritzsch |
| 5,443,470 | A | 8/1995 | Stern et al. |
| 5,454,782 | A | 10/1995 | Perkins |
| 5,454,809 | A | 10/1995 | Janssen |
| 5,456,662 | A | 10/1995 | Edwards et al. |
| 5,456,682 | A | 10/1995 | Edwards et al. |
| 5,458,571 | A | 10/1995 | Lampropoulos et al. |
| 5,458,596 | A | 10/1995 | Lax et al. |
| 5,458,597 | A | 10/1995 | Edwards et al. |
| 5,462,545 | A | 10/1995 | Wang et al. |
| 5,465,717 | A | 11/1995 | Imran et al. |
| 5,470,308 | A | 11/1995 | Edwards et al. |
| 5,471,982 | A | 12/1995 | Edwards et al. |
| 5,472,441 | A | 12/1995 | Edwards et al. |
| 5,484,400 | A | 1/1996 | Edwards et al. |
| 5,486,161 | A | 1/1996 | Lax et al. |
| 5,490,984 | A | 2/1996 | Freed |
| 5,496,271 | A | 3/1996 | Burton et al. |
| 5,496,311 | A | 3/1996 | Abele et al. |
| 5,500,012 | A | 3/1996 | Brucker et al. |
| 5,505,728 | A | 4/1996 | Ellman et al. |
| 5,505,730 | A | 4/1996 | Edwards |
| 5,507,743 | A | 4/1996 | Edwards et al. |
| 5,509,419 | A | 4/1996 | Edwards et al. |
| 5,514,130 | A | 5/1996 | Baker |
| 5,514,131 | A | 5/1996 | Edwards et al. |
| 5,517,989 | A | 5/1996 | Frisbie et al. |
| 5,520,684 | A | 5/1996 | Imran |

(56) References Cited

U.S. PATENT DOCUMENTS

| | | |
|---|---|---|
| 5,522,815 A | 6/1996 | Burgin, Jr. et al. |
| 5,524,622 A | 6/1996 | Wilson |
| 5,531,676 A | 7/1996 | Edwards et al. |
| 5,531,677 A | 7/1996 | Lundquist et al. |
| 5,533,958 A | 7/1996 | Wilk |
| 5,536,240 A | 7/1996 | Edwards et al. |
| 5,536,267 A | 7/1996 | Edwards et al. |
| 5,540,655 A | 7/1996 | Edwards et al. |
| 5,540,679 A | 7/1996 | Fram et al. |
| 5,542,916 A | 8/1996 | Hirsch et al. |
| 5,542,928 A | 8/1996 | Evans et al. |
| 5,549,644 A | 8/1996 | Lundquist et al. |
| 5,549,661 A | 8/1996 | Korkis et al. |
| RE35,330 E | 9/1996 | Malone et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,562,720 A | 10/1996 | Stern et al. |
| 5,566,221 A | 10/1996 | Smith et al. |
| 5,569,241 A | 10/1996 | Edwards |
| 5,571,116 A | 11/1996 | Bolanos et al. |
| 5,578,007 A | 11/1996 | Imran |
| 5,588,432 A | 12/1996 | Crowley |
| 5,588,960 A | 12/1996 | Edwards et al. |
| 5,591,195 A | 1/1997 | Taheri et al. |
| 5,599,345 A | 2/1997 | Edwards et al. |
| 5,609,151 A | 3/1997 | Mulier et al. |
| 5,621,780 A | 4/1997 | Smith et al. |
| 5,624,439 A | 4/1997 | Edwards et al. |
| 5,651,780 A | 7/1997 | Jackson et al. |
| 5,651,788 A | 7/1997 | Fleischer et al. |
| 5,658,278 A | 8/1997 | Imran et al. |
| 5,672,153 A | 9/1997 | Lax et al. |
| 5,676,674 A | 10/1997 | Bolanos et al. |
| 5,688,266 A | 11/1997 | Edwards et al. |
| 5,688,490 A | 11/1997 | Tournier et al. |
| 5,702,438 A | 12/1997 | Avitall |
| 5,709,224 A | 1/1998 | Behl et al. |
| 5,713,942 A | 2/1998 | Stern et al. |
| 5,716,410 A | 2/1998 | Wang et al. |
| 5,720,293 A | 2/1998 | Quinn et al. |
| 5,730,128 A | 3/1998 | Pomeranz et al. |
| 5,732,698 A | 3/1998 | Swanson et al. |
| 5,738,096 A | 4/1998 | Ben-Haim |
| 5,748,699 A | 5/1998 | Smith |
| 5,769,846 A | 6/1998 | Edwards et al. |
| 5,769,880 A | 6/1998 | Truckai et al. |
| 5,779,698 A | 7/1998 | Clayman et al. |
| 5,797,835 A | 8/1998 | Green |
| 5,797,903 A | 8/1998 | Swanson et al. |
| 5,800,334 A | 9/1998 | Wilk |
| 5,800,429 A | 9/1998 | Edwards |
| 5,807,261 A | 9/1998 | Benaron et al. |
| 5,820,629 A | 10/1998 | Cox |
| 5,823,197 A | 10/1998 | Edwards |
| 5,823,955 A | 10/1998 | Kuck et al. |
| 5,827,273 A | 10/1998 | Edwards |
| 5,830,129 A | 11/1998 | Baer et al. |
| 5,830,213 A | 11/1998 | Panescu et al. |
| 5,833,688 A | 11/1998 | Sieben et al. |
| 5,836,874 A | 11/1998 | Swanson et al. |
| 5,842,984 A | 12/1998 | Avitall |
| 5,846,196 A | 12/1998 | Siekmeyer et al. |
| 5,860,974 A | 1/1999 | Abele |
| 5,861,036 A | 1/1999 | Godin |
| 5,863,291 A | 1/1999 | Schaer |
| 5,871,483 A | 2/1999 | Jackson et al. |
| 5,876,340 A | 3/1999 | Tu et al. |
| 5,888,743 A | 3/1999 | Das |
| 5,891,134 A | 4/1999 | Goble et al. |
| 5,895,355 A | 4/1999 | Schaer |
| 5,902,263 A | 5/1999 | Patterson et al. |
| 5,904,711 A | 5/1999 | Flom et al. |
| 5,925,044 A | 7/1999 | Hofmann et al. |
| 5,938,694 A | 8/1999 | Jaraczewski et al. |
| 5,964,755 A | 10/1999 | Edwards |
| 5,976,129 A | 11/1999 | Desai |
| 5,984,861 A | 11/1999 | Crowley |
| 5,997,534 A | 12/1999 | Tu et al. |
| 6,006,755 A | 12/1999 | Edwards |
| 6,010,511 A | 1/2000 | Murphy |
| 6,012,457 A | 1/2000 | Lesh |
| 6,016,437 A | 1/2000 | Tu et al. |
| 6,023,638 A | 2/2000 | Swanson et al. |
| 6,027,499 A | 2/2000 | Johnston et al. |
| 6,033,397 A | 3/2000 | Laufer et al. |
| 6,039,701 A | 3/2000 | Sliwa et al. |
| 6,041,260 A | 3/2000 | Stern et al. |
| 6,044,846 A | 4/2000 | Edwards |
| 6,053,172 A | 4/2000 | Hovda et al. |
| 6,053,913 A | 4/2000 | Tu et al. |
| 6,056,744 A | 5/2000 | Edwards |
| 6,059,719 A | 5/2000 | Yamamoto et al. |
| 6,068,629 A | 5/2000 | Haissaguerre et al. |
| 6,071,277 A | 6/2000 | Farley et al. |
| 6,073,052 A | 6/2000 | Zelickson et al. |
| 6,086,558 A | 7/2000 | Bower et al. |
| 6,091,993 A | 7/2000 | Bouchier et al. |
| 6,091,995 A | 7/2000 | Ingle et al. |
| 6,092,528 A | 7/2000 | Edwards |
| 6,095,966 A | 8/2000 | Chornenky et al. |
| 6,096,054 A | 8/2000 | Wyzgala et al. |
| 6,102,908 A | 8/2000 | Tu et al. |
| 6,112,123 A | 8/2000 | Kelleher et al. |
| 6,120,434 A | 9/2000 | Kimura et al. |
| 6,123,703 A | 9/2000 | Tu et al. |
| 6,123,718 A | 9/2000 | Tu et al. |
| 6,138,046 A | 10/2000 | Dalton |
| 6,142,994 A | 11/2000 | Swanson et al. |
| 6,146,149 A | 11/2000 | Daound |
| 6,149,647 A | 11/2000 | Tu et al. |
| 6,162,237 A | 12/2000 | Chan |
| 6,179,836 B1 | 1/2001 | Eggers et al. |
| 6,182,666 B1 | 2/2001 | Dobak, III |
| 6,183,468 B1 | 2/2001 | Swanson et al. |
| 6,193,644 B1 | 2/2001 | Dobak, III et al. |
| 6,197,022 B1 | 3/2001 | Baker |
| 6,237,355 B1 | 5/2001 | Li |
| 6,238,392 B1 | 5/2001 | Long |
| 6,245,065 B1 | 6/2001 | Panescu et al. |
| 6,254,598 B1 | 7/2001 | Edwards et al. |
| 6,258,087 B1 | 7/2001 | Edwards et al. |
| 6,258,118 B1 | 7/2001 | Baum et al. |
| 6,273,886 B1 | 8/2001 | Edwards et al. |
| 6,321,121 B1 | 11/2001 | Zelickson et al. |
| 6,325,798 B1 | 12/2001 | Edwards et al. |
| 6,325,800 B1 | 12/2001 | Durgin et al. |
| 6,338,726 B1 | 1/2002 | Edwards et al. |
| 6,355,031 B1 | 3/2002 | Edwards et al. |
| 6,355,032 B1 | 3/2002 | Hovda et al. |
| 6,358,245 B1 | 3/2002 | Edwards et al. |
| 6,363,937 B1 | 4/2002 | Hovda et al. |
| 6,383,181 B1 | 5/2002 | Johnston et al. |
| 6,394,949 B1 | 5/2002 | Crowley et al. |
| 6,402,744 B2 | 6/2002 | Edwards et al. |
| 6,405,732 B1 | 6/2002 | Edwards et al. |
| 6,409,723 B1 | 6/2002 | Edwards |
| H2037 H | 7/2002 | Yates et al. |
| 6,415,016 B1 | 7/2002 | Chornenky et al. |
| 6,416,511 B1 | 7/2002 | Lesh et al. |
| 6,423,058 B1 | 7/2002 | Edwards et al. |
| 6,425,877 B1 | 7/2002 | Edwards |
| 6,428,536 B2 | 8/2002 | Panescu et al. |
| 6,432,104 B1 | 8/2002 | Eurgin et al. |
| 6,440,128 B1 | 8/2002 | Edwards et al. |
| 6,448,658 B2 | 9/2002 | Takata et al. |
| 6,451,014 B1 | 9/2002 | Wakikaido et al. |
| 6,454,790 B1 | 9/2002 | Neuberger et al. |
| 6,464,697 B1 | 10/2002 | Edwards et al. |
| 6,468,272 B1 | 10/2002 | Koblish et al. |
| 6,514,246 B1 | 2/2003 | Swanson et al. |
| 6,514,249 B1 | 2/2003 | Maguire et al. |
| 6,535,768 B1 | 3/2003 | Baker et al. |

(56) References Cited

U.S. PATENT DOCUMENTS

| | | | |
|---|---|---|---|
| 6,544,226 B1 | 4/2003 | Gaiser et al. | |
| 6,547,776 B1 | 4/2003 | Gaiser et al. | |
| 6,547,787 B1 | 4/2003 | Altman et al. | |
| 6,551,302 B1 | 4/2003 | Rosinko et al. | |
| 6,551,310 B1 | 4/2003 | Ganz et al. | |
| 6,551,315 B2 | 4/2003 | Kortenbach et al. | |
| 6,558,400 B2 | 5/2003 | Deem et al. | |
| 6,562,034 B2 | 5/2003 | Edwards et al. | |
| 6,569,162 B2 | 5/2003 | He | |
| 6,572,578 B1 | 6/2003 | Blanchard | |
| 6,572,610 B2 | 6/2003 | Kovalcheck et al. | |
| 6,572,639 B1 | 6/2003 | Ingle et al. | |
| 6,575,966 B2 | 6/2003 | Lane et al. | |
| 6,589,238 B2 | 7/2003 | Edwards et al. | |
| 6,613,047 B2 | 9/2003 | Edwards | |
| 6,641,581 B2 | 11/2003 | Muzzammel | |
| 6,663,626 B2 | 12/2003 | Truckai et al. | |
| 6,673,070 B2 | 1/2004 | Edwards et al. | |
| 6,682,528 B2 | 1/2004 | Frazier et al. | |
| 6,689,130 B2 | 2/2004 | Arai et al. | |
| 6,695,764 B2 | 2/2004 | Silverman et al. | |
| 6,712,074 B2 | 3/2004 | Edwards et al. | |
| 6,712,814 B2 | 3/2004 | Edwards et al. | |
| 6,712,815 B2 | 3/2004 | Sampson et al. | |
| 6,740,082 B2 | 5/2004 | Shadduck | |
| 6,749,607 B2 | 6/2004 | Edwards et al. | |
| 6,752,806 B2 | 6/2004 | Durgin et al. | |
| 6,800,083 B2 | 10/2004 | Hiblar et al. | |
| 6,837,886 B2 | 1/2005 | Collins et al. | |
| 6,846,312 B2 | 1/2005 | Edwards et al. | |
| 6,860,878 B2 | 3/2005 | Brock | |
| 6,866,663 B2 | 3/2005 | Edwards et al. | |
| 6,872,206 B2 | 3/2005 | Edwards et al. | |
| 6,917,834 B2 | 7/2005 | Koblish et al. | |
| 6,918,906 B2 | 7/2005 | Long | |
| 6,923,808 B2 | 8/2005 | Taimisto | |
| 6,929,642 B2 | 8/2005 | Xiao et al. | |
| 6,953,469 B2 | 10/2005 | Ryan | |
| 6,964,661 B2 | 11/2005 | Rioux et al. | |
| 6,971,395 B2 | 12/2005 | Edwards et al. | |
| 6,974,456 B2 | 12/2005 | Edwards et al. | |
| 6,994,704 B2 | 2/2006 | Qin et al. | |
| 7,004,938 B2 | 2/2006 | Ormsby et al. | |
| 7,048,734 B1 | 5/2006 | Fleischman et al. | |
| 7,056,320 B2 | 6/2006 | Utley et al. | |
| 7,083,620 B2 | 8/2006 | Jahns et al. | |
| 7,089,063 B2 | 8/2006 | Lesh et al. | |
| 7,122,031 B2 | 10/2006 | Edwards et al. | |
| 7,125,407 B2 | 10/2006 | Edwards et al. | |
| 7,160,294 B2 | 1/2007 | Croft | |
| 7,165,551 B2 | 1/2007 | Edwards | |
| 7,167,758 B2 | 1/2007 | Baker et al. | |
| 7,179,257 B2 | 2/2007 | West et al. | |
| 7,184,827 B1 | 2/2007 | Edwards | |
| 7,252,665 B2 * | 8/2007 | Starkebaum et al. | 606/41 |
| 7,282,049 B2 | 10/2007 | Orszulak et al. | |
| 7,282,050 B2 * | 10/2007 | Starkebaum et al. | 606/41 |
| 7,288,101 B2 | 10/2007 | Deem et al. | |
| 7,293,563 B2 | 11/2007 | Utley et al. | |
| 7,326,207 B2 | 2/2008 | Edwards | |
| 7,329,254 B2 | 2/2008 | West et al. | |
| 7,416,549 B2 | 8/2008 | Young et al. | |
| 7,425,212 B1 | 9/2008 | Danek et al. | |
| 7,468,060 B2 * | 12/2008 | Utley et al. | 606/41 |
| 7,632,268 B2 * | 12/2009 | Edwards et al. | 606/41 |
| 7,680,543 B2 | 3/2010 | Azure | |
| 7,850,685 B2 | 12/2010 | Kunis et al. | |
| 2001/0007938 A1 * | 7/2001 | Long | 606/41 |
| 2001/0041887 A1 | 11/2001 | Crowley | |
| 2001/0051802 A1 | 12/2001 | Woloszko et al. | |
| 2002/0035324 A1 | 3/2002 | Sirimanne et al. | |
| 2002/0087151 A1 | 7/2002 | Mody et al. | |
| 2002/0177847 A1 | 11/2002 | Long | |
| 2002/0183739 A1 | 12/2002 | Long | |
| 2003/0069572 A1 | 4/2003 | Wellman et al. | |
| 2003/0093117 A1 | 5/2003 | Saadat | |
| 2003/0109837 A1 | 6/2003 | McBride-Sakal | |
| 2003/0153905 A1 | 8/2003 | Edwards et al. | |
| 2003/0158550 A1 | 8/2003 | Ganz et al. | |
| 2003/0181900 A1 | 9/2003 | Long | |
| 2003/0181905 A1 | 9/2003 | Long | |
| 2003/0191512 A1 | 10/2003 | Laufer et al. | |
| 2003/0216727 A1 | 11/2003 | Long | |
| 2004/0087936 A1 * | 5/2004 | Stern et al. | 606/41 |
| 2004/0089313 A1 * | 5/2004 | Utley et al. | 128/898 |
| 2004/0122452 A1 | 6/2004 | Deem et al. | |
| 2004/0147916 A1 | 7/2004 | Baker | |
| 2004/0153120 A1 | 8/2004 | Seifert et al. | |
| 2004/0172016 A1 | 9/2004 | Bek et al. | |
| 2004/0204708 A1 | 10/2004 | Edwards et al. | |
| 2004/0215180 A1 | 10/2004 | Starkebaum et al. | |
| 2004/0215235 A1 | 10/2004 | Jackson et al. | |
| 2004/0215296 A1 | 10/2004 | Ganz et al. | |
| 2004/0236316 A1 | 11/2004 | Danitz et al. | |
| 2004/0243124 A1 | 12/2004 | Im et al. | |
| 2005/0010162 A1 | 1/2005 | Utley et al. | |
| 2005/0033271 A1 | 2/2005 | Qin et al. | |
| 2005/0055038 A1 | 3/2005 | Kelleher et al. | |
| 2005/0070978 A1 | 3/2005 | Bek et al. | |
| 2005/0090817 A1 | 4/2005 | Phan | |
| 2005/0096713 A1 * | 5/2005 | Starkebaum et al. | 607/100 |
| 2005/0107829 A1 | 5/2005 | Edwards et al. | |
| 2005/0143727 A1 | 6/2005 | Koblish et al. | |
| 2005/0149013 A1 | 7/2005 | Lee | |
| 2005/0154386 A1 | 7/2005 | West et al. | |
| 2005/0159743 A1 | 7/2005 | Edwards et al. | |
| 2005/0171524 A1 | 8/2005 | Stern et al. | |
| 2005/0183732 A1 * | 8/2005 | Edwards | 128/898 |
| 2005/0187546 A1 | 8/2005 | Bek et al. | |
| 2005/0203501 A1 | 9/2005 | Aldrich et al. | |
| 2005/0215983 A1 | 9/2005 | Brock | |
| 2005/0240239 A1 | 10/2005 | Boveja et al. | |
| 2005/0245926 A1 | 11/2005 | Edwards et al. | |
| 2005/0288664 A1 | 12/2005 | Ford et al. | |
| 2006/0009758 A1 | 1/2006 | Edwards et al. | |
| 2006/0015151 A1 | 1/2006 | Aldrich | |
| 2006/0015162 A1 | 1/2006 | Edward et al. | |
| 2006/0041256 A1 | 2/2006 | Edwards et al. | |
| 2006/0069303 A1 | 3/2006 | Couvillon | |
| 2006/0086362 A1 | 4/2006 | Solomon | |
| 2006/0086363 A1 | 4/2006 | Qin et al. | |
| 2006/0095032 A1 | 5/2006 | Jackson et al. | |
| 2006/0217698 A1 | 9/2006 | Starkebaum et al. | |
| 2006/0247614 A1 | 11/2006 | Sampson et al. | |
| 2006/0259028 A1 | 11/2006 | Utley et al. | |
| 2006/0259029 A1 | 11/2006 | Utley et al. | |
| 2006/0259030 A1 | 11/2006 | Utley et al. | |
| 2006/0282071 A1 | 12/2006 | Utley et al. | |
| 2007/0016274 A1 | 1/2007 | Boveja et al. | |
| 2007/0021743 A1 | 1/2007 | Rioux et al. | |
| 2007/0066973 A1 | 3/2007 | Stern et al. | |
| 2007/0100333 A1 | 5/2007 | Jackson et al. | |
| 2007/0118104 A1 | 5/2007 | Wallace et al. | |
| 2007/0118106 A1 | 5/2007 | Utley et al. | |
| 2007/0118159 A1 | 5/2007 | Deem et al. | |
| 2007/0135809 A1 | 6/2007 | Utley et al. | |
| 2007/0142831 A1 | 6/2007 | Shadduck | |
| 2007/0167963 A1 | 7/2007 | Deem et al. | |
| 2007/0175488 A1 | 8/2007 | Cox et al. | |
| 2007/0219570 A1 | 9/2007 | Deem et al. | |
| 2007/0255296 A1 | 11/2007 | Sauer | |
| 2007/0265608 A1 | 11/2007 | Hernandez | |
| 2007/0287994 A1 | 12/2007 | Patel | |
| 2007/0288001 A1 | 12/2007 | Patel | |
| 2008/0097427 A1 | 4/2008 | Stern et al. | |
| 2008/0319350 A1 | 12/2008 | Wallace et al. | |
| 2009/0012512 A1 | 1/2009 | Utley et al. | |
| 2009/0012513 A1 | 1/2009 | Utley et al. | |

(56) References Cited

U.S. PATENT DOCUMENTS

| | | |
|---|---|---|
| 2009/0012518 A1 | 1/2009 | Utley et al. |
| 2010/0063495 A1 | 3/2010 | Utley et al. |

FOREIGN PATENT DOCUMENTS

| | | |
|---|---|---|
| EP | 0105677 | 4/1984 |
| EP | 0115420 | 8/1984 |
| EP | 0139607 | 5/1985 |
| EP | 0251745 | 1/1988 |
| EP | 0521595 A2 | 1/1993 |
| EP | 0608609 | 8/1994 |
| EP | 1323382 A1 | 7/2003 |
| EP | 0754075 B1 | 3/2006 |
| EP | 1634542 B1 | 3/2006 |
| EP | 1562506 B1 | 5/2009 |
| JP | 8-506738 | 7/1996 |
| JP | 2005503181 | 2/2005 |
| WO | WO 91/01773 | 2/1991 |
| WO | WO 91/03207 A1 | 3/1991 |
| WO | WO 92/10142 | 6/1992 |
| WO | WO 93/08755 | 5/1993 |
| WO | WO 94/07446 A1 | 4/1994 |
| WO | WO 94/10925 | 5/1994 |
| WO | WO 94/21165 | 9/1994 |
| WO | WO 94/21178 | 9/1994 |
| WO | WO 94/22366 | 10/1994 |
| WO | WO 94/26178 | 11/1994 |
| WO | WO 95/18575 | 7/1995 |
| WO | WO 95/19142 | 7/1995 |
| WO | WO 95/25472 | 9/1995 |
| WO | WO 96/00042 | 1/1996 |
| WO | WO 96/16606 | 6/1996 |
| WO | WO 96/29946 | 10/1996 |
| WO | WO 97/04702 | 2/1997 |
| WO | WO 97/06857 | 2/1997 |
| WO | WO 97/32532 | 9/1997 |
| WO | WO 97/43971 | 11/1997 |
| WO | WO 98/12999 A2 | 4/1998 |
| WO | WO 98/14238 A1 | 4/1998 |
| WO | WO 98/18393 A1 | 5/1998 |
| WO | WO 99/03413 | 1/1999 |
| WO | WO 99/35987 | 7/1999 |
| WO | WO 99/42046 | 8/1999 |
| WO | WO 99/55245 | 11/1999 |
| WO | WO 00/01313 | 1/2000 |
| WO | WO 00/59393 | 10/2000 |
| WO | WO 00/62699 A2 | 10/2000 |
| WO | WO 00/66017 A1 | 11/2000 |
| WO | WO 00/66021 | 11/2000 |
| WO | WO 00/66052 A1 | 11/2000 |
| WO | WO 00/69376 A1 | 11/2000 |
| WO | WO 01/22897 A1 | 4/2001 |
| WO | WO 01/35846 | 5/2001 |
| WO | WO 01/45550 A2 | 6/2001 |
| WO | WO 01/89440 | 11/2001 |
| WO | WO 02/096327 A2 | 12/2002 |
| WO | WO 03/070091 A1 | 8/2003 |
| WO | WO 2004/021894 A1 | 3/2004 |
| WO | WO 2004/043280 A1 | 5/2004 |
| WO | WO 2007/001981 A2 | 1/2007 |
| WO | WO 2007/061984 A2 | 5/2007 |

OTHER PUBLICATIONS

Jackson, Jerome; U.S. Appl. No. 13/181,484 entitled "Methods and systems for treatment of tissue in a body lumen," filed Jul. 12, 2011.

Utley et al.; U.S. Appl. No. 13/181,490 entitled "Precision ablating method," filed Jul. 12, 2011.

Jackson et al.; U.S. Appl. No. 13/189,793 entitled "Methods and Systems for Determining Physiologic Characteristics for Treatment of the Esophagus," filed Jul. 25, 2011.

Wallace et al; U.S. Appl. No. 11/830,251 entitled "Cleaning Devices and Methods," filed Jul. 30, 2007.

Utley et al; U.S. Appl. No. 11/830,291 entitled "Cleaning Device and Methods," filed Jul. 30, 2007.

Castell, D.O. Gastroesophageal Reflux Disease: Current Strategies for Patient Management. Arch Fam Med. 1996; 5(4):221-227.

Dallamagne et al; Laparoscopic Nissen Fundoplication: Preliminary. Surgical Laparoscopy and Endoscopy. 1991; 1(3):138-143.

Hinder et al; The Technique of Laparoscopic Nissen Fundoplication. Surgical Laparoscopy and Endoscopy. 1992; 2(3):265-272.

Kaneko et al; Physiological Laryngeal Pacemaker. Trans Am Soc. Artif Intern Organs. 1985; XXXI:293-296.

Karlstrom et al; Ectopic Jejunal Pacemakers and Enterogastric Reflux Roux Gastrectomy: Effect of Intestinal Pacing. Surgery. 1989; 106(3):486-495.

Kelly, K.A. et al; Duodenal-Gastric Reflux and Slowed Gastric Emptying by Electrical Pacing of the Canine Duodenal Pacesetter Potential. Gastroenterology. 1977; 72(3):429-433.

Mugica, et al. Direct Diaphragm Stimulation. PACE. 1987; 10:252-256.

Mugica, et al., Preliminary Test of a Muscular Diaphragm Pacing System on Human Patients. Neurostimulation: An Overview, chapter 21. 1985; 263-279.

Reynolds, J.C. Influence of Pathophysiology, Severity, and Cost on the Medical Management of Gastroesophageal Reflux Disease. Am J. Health-Syst Phar. 1996; 53(22sul3):S5-S12.

Rice et al; Endoscopic Paranasal Sinus Surgery. Chapter 5, Functional Endoscopic Paranasal Sinus Surgery, The Technique of Messerklinger. Raven Press. 1988; 75-102.

Rice et al; Endoscopic Paranasal Sinus Surgery. Chapter 6, Total Endoscopic Sphenoethmoidectomy. The Technique of Wigand. Raven Press. 1988; 103-125.

Rubino, et al.; Potential of Surgery for Curing Type 2 Diabetes Mellitus; Annals of Surgery, vol. 236; No. 5; pp. 554-559, 2002.

Rubino, et al.; Effect of Duodenal-Jejunal Exclusion in a Non-Obese Animal Model of Type 2 Diabetes: A New Perspective for an Old Disease; Annals of Surgery, vol. 240, No. 2, pp. 389-391, Aug. 2004.

Salameh et al; An Animal Model Study to Clarify and Investigate Endoscopic Tissue Coagulation by Using a New Monopolar Device. Gastrointestinal Endoscopy; 2004; 59 (1): 107-112.

Urshel, J.D. Complications of Antireflux Surgery. Am J. Surg. 1993; 166(1):68-70.

DiabetesInControl.com, "How tummy surgery cures diabetes in a matter of days," Art. No. 4859, (website accessed Jun. 6, 2007).

Drucker, The role of gut hormones in glucose homeostasis, The Journal of Clinical Investigation, vol. 117, No. 1, Jan. 2007.

Jackson et al.; U.S. Appl. No. 12/787,324 entitled "Methods and systems for determining physiologic characteristics for treatment of the esophagus," filed May 25, 2010.

Ganz et al; U.S. Appl. No. 12/259,136 entitled "System and method of treating abnormal tissue in the human esophagus," filed Oct. 27, 2008.

Utley, David S.; U.S. Appl. No. 12/270,373 entitled "System and method for ablational treatment of uterine cervical neoplasma," filed Nov. 13, 2008.

Maggs et al.; Glucose homeostasis and the gastrointestinal tract: insights into the treatment of diabetes; Diabetes, Obesity and Metabolism; pp. 1-16; 2007.

Shadduck, John H.; U.S. Appl. No. 12/751,803 entitled "Surgical instruments and techniques for treating gastro-esophageal reflux disease," filed Mar. 31, 2010.

Ungar, Bariatric surgery may eliminate need for medication in nonobese type 2 diabetes, Medscape Medical News, Art. No. 573142, 2008.

Shadduck, John; U.S. Appl. No. 12/368,943 entitled "Surgical instruments and techniques for treating gastro-esophageal reflux disease," filed Feb. 10, 2009.

Wallace et al.; U.S. Appl. No. 12/404,159 entitled "Auto-aligning ablating device and method of use," filed Mar. 13, 2009.

* cited by examiner

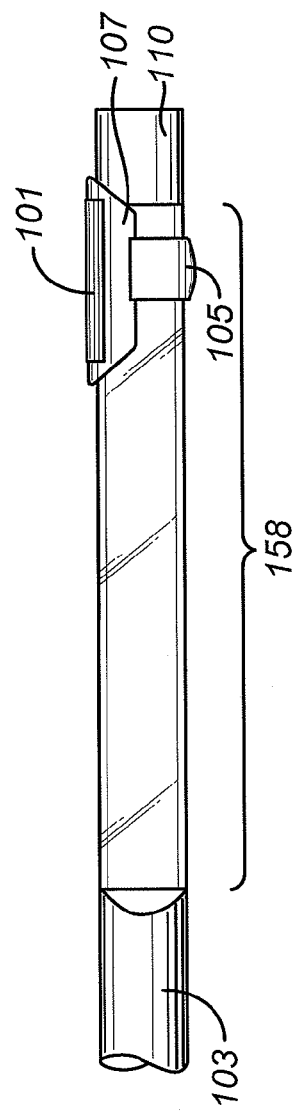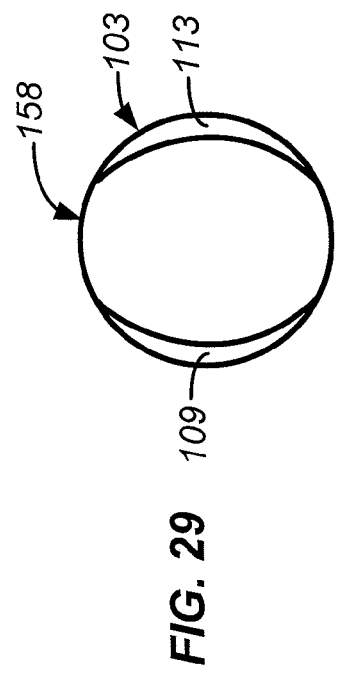

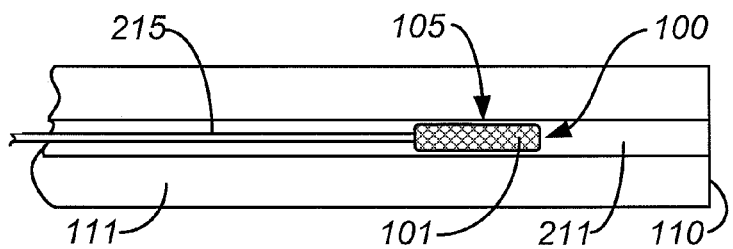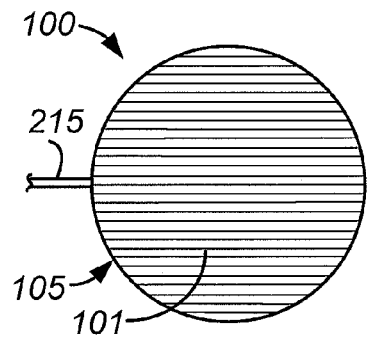
FIG. 34A
FIG. 34B
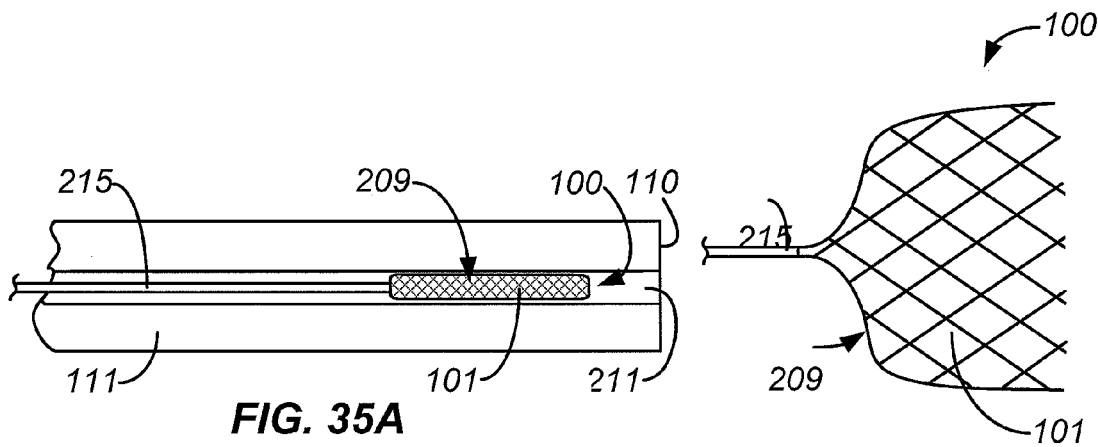
FIG. 35A
FIG. 35B
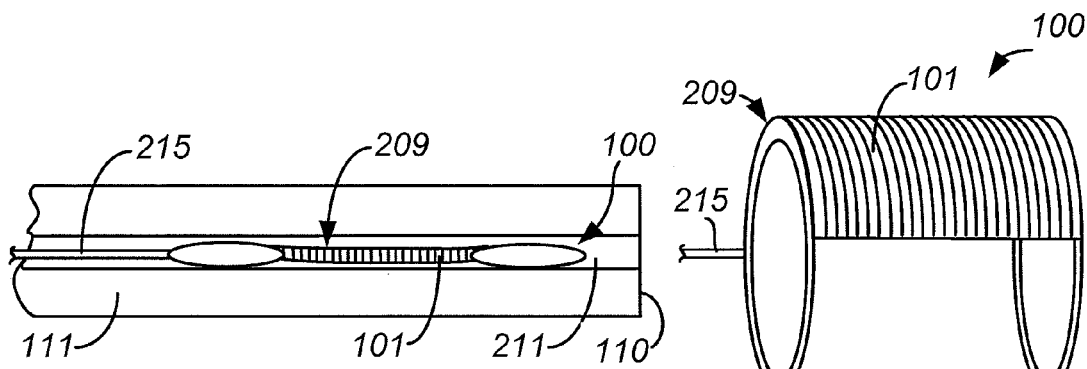
FIG. 36A
FIG. 36B

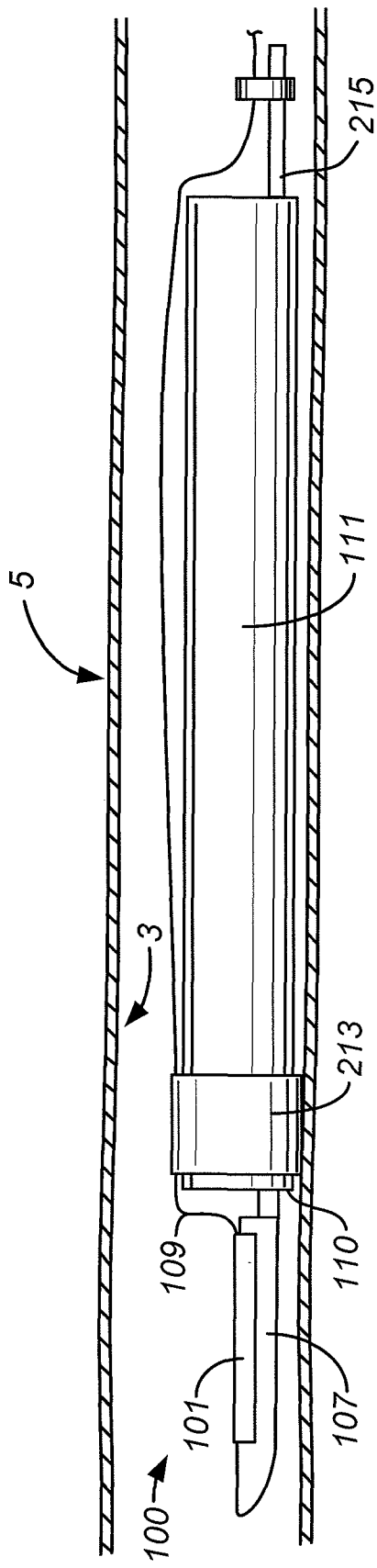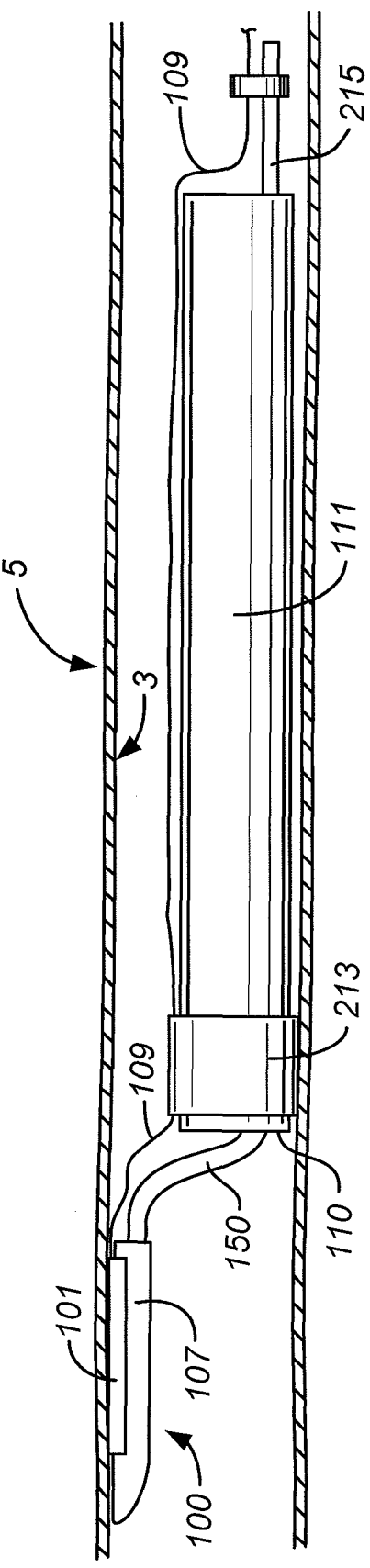

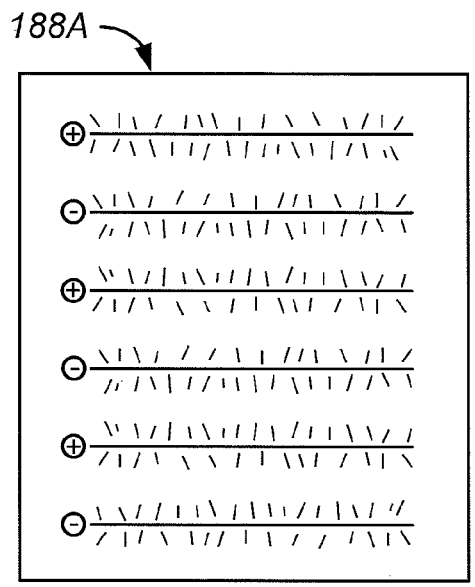
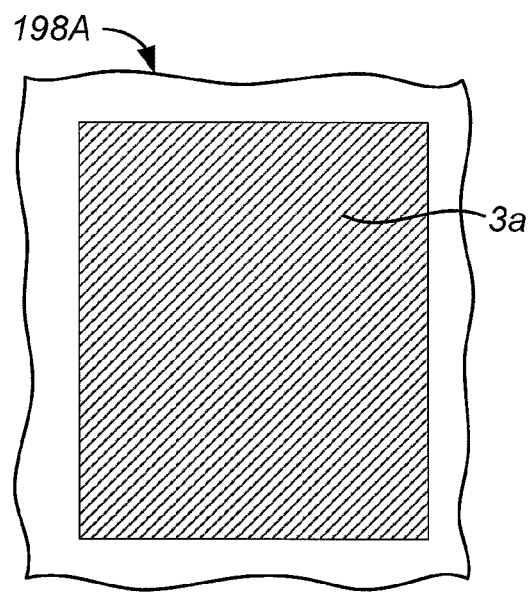
FIG. 53A                FIG. 53B
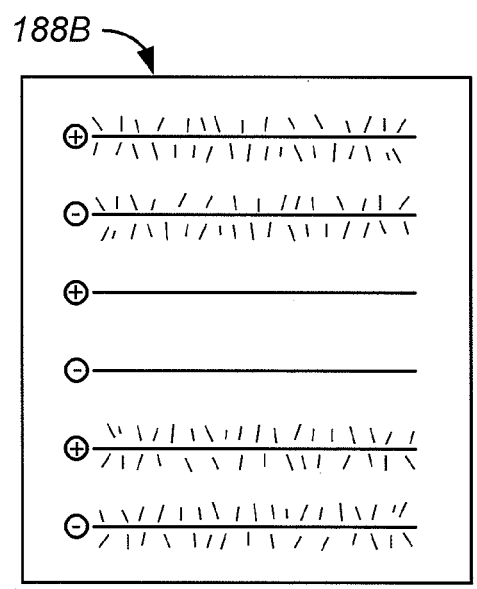
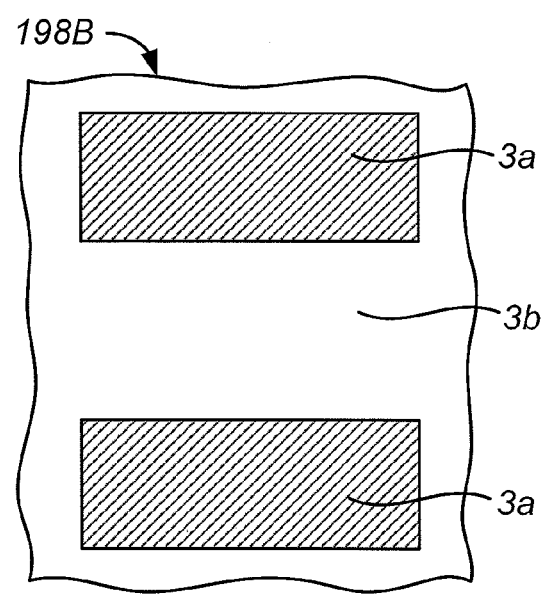
FIG. 54A                FIG. 54B

METHOD AND APPARATUS FOR GASTROINTESTINAL TRACT ABLATION FOR TREATMENT OF OBESITY

CROSS REFERENCE TO RELATED APPLICATIONS

This application claims priority to U.S. Provisional Patent Application No. 60/916,248 entitled "Method and Apparatus for Treating Obesity" by Utley, et al., as filed on May 4, 2007, to U.S. Provisional Patent Application No. 60/958,543 entitled "Non-Barrett's Mucosal Ablation and Tissue Tightening Indications Related to Obesity" by Utley, as filed on Jul. 6, 2007, and to U.S. Provisional Patent Application No. 60/958,562 entitled "Non-Barrett's Mucosal Ablation Disease Targets", as filed on Jul. 6, 2007.

This application is also related to, and incorporates in entirety commonly assigned U.S. patent application Ser. No. 10/370,645 entitled "Method of treating abnormal tissue in the human esophagus", filed on Feb. 19, 2003, and published as US 2003/0158550 on Aug. 21, 2003, and this present application is also a continuation-in-part of U.S. patent application Ser. No. 11/286,444 entitled "Precision Ablating Method", filed on Nov. 23, 2005, and published as US 2007/0118106 on May 24, 2007. Further, each of the following commonly assigned United States Patent Applications are incorporated herein by reference in its entirety: patent application Ser. No. 10/291,862 titled "Systems and Methods for Treating Obesity and Other Gastrointestinal Conditions," patent application Ser. No. 10/370,645 titled "Method of Treating Abnormal Tissue In The Human Esophagus," patent application Ser. No. 11/286,257 titled "Precision Ablating Device," patent application Ser. No. 11/275,244 titled "Auto-aligning ablating device and method of use," patent application Ser. No. 11/286,444 titled "Precision Ablating Device," patent application Ser. No. 11/420,712 titled "System for Tissue Ablation," patent application Ser. No. 11/420,714 titled "Method for Cryogenic Tissue Ablation," patent application Ser. No. 11/420,719 titled "Method for Vacuum-Assisted Tissue Ablation," patent application Ser. No. 11/420,722 titled "Method for Tissue Ablation," patent application Ser. No. 11/469,816 titled "Surgical instruments and techniques for treating gastro-esophageal reflux disease." This application further incorporates in entirety U.S. patent application Ser. No. 10/291,862, filed on Nov. 8, 2002 entitled "Systems and methods for treating obesity and other gastrointestinal conditions, and published on May 13, 2004 as US 2004/0089313, and U.S. Pat. No. 7,326,207, entitled "surgical weight control device", which issued on Feb. 5, 2008.

INCORPORATION BY REFERENCE

All publications, patents and patent applications mentioned in this specification are herein incorporated by reference to the same extent as if each individual publication, patent or patent application was specifically and individually indicated to be incorporated by reference.

FIELD OF THE INVENTION

The invention relates to medical devices and methods for the use thereof for the ablating of tissue in the gastrointestinal tract for the treatment of metabolic disease and obesity.

BACKGROUND OF THE INVENTION

Gastric bypass surgical procedures whose original intended result was to cause weight loss by virtue of a major decrease in nutrient absorption, in addition to a significant degree of success toward that end, have also resulted in the amelioration or elimination of Type 2 diabetes mellitus in 70-80% of post-operative patients. The prevalence and the extremely quick time course of this effect in reducing diabetes was not generally anticipated, nor can it be satisfactorily explained by weight loss alone.

It has been hypothesized (Rubino and Gagner, "Potential of surgery for curing type 2 diabetes mellitus", Annals of Surgery (2002) 236 (5), 554-559, Rubino and Marescaux, "Effect of duodenal-jejunal exclusion in a non-obese animal model of type 2 diabetes: a new perspective for an old disease" Annals of Surgery (2004) 240(2): 389-391) that the removal or functional compromise of endocrine and neural cells within the epithelium of the intestinal tract, the small bowel in particular, which normally respond to the passage of nutrient flow were at least partially responsible for the decrease in diabetes symptoms in these treated patients. Various hormones secreted by endocrine cells in the duodenum and jejunum are collectively known as incretins, and include gastroinhibitory peptide (GIP), glucagon-like peptide (GLP-1), and insulin-like growth factor (IGF-1). The passage or presence of nutrients in the intestine stimulate the release of these hormones which have a broadly stimulatory effect on insulin secretion by the pancreas, and on enhancing the effectiveness of insulin on its targets. This relationship makes sense in that insulin helps the body to move glucose and amino acids from the blood stream into tissues, and thus the incretins prepare the body to receive nutrients that are sensed within the intestine even before the nutrients move into the bloodstream. In the pathogenesis of diabetes, however, there is an excessive amount of insulin secreted, and in response the cells responsive to insulin become overly stimulated and compensate by becoming insulin resistant. The patient with type 2 diabetes thus has a surfeit of insulin, but physiologically acts as if there is an insulin deficit. Accordingly, insulin levels and blood glucose levels are high. Whether the initial disturbance is diabetes or an over consumption of calories independent of diabetes, the end result is similar, and most obese patients are have type 2 (non-insulin-dependent) diabetes mellitus.

Other factors may be involved in the striking anti-diabetic response to bariatric surgery, such as an increase in the levels of anti-incretin factors, which would favor the effectiveness of insulin action. Additionally, the stomach wall itself is a source of hormones such as cholecystokinin (CCK), gastrin, and ghrelin, all of which play various roles in the handling of nutrients, the activity of other hormones, particularly pancreatic hormones, and on the sensation of satiety, which has further neural and behavioral consequences. Additionally, the intestine is well innervated with chemically sensitive receptors that respond to the nutrients in the stomach and intestine, and mechanically sensitive cells that respond to the volume of material in the gut and the state of smooth muscle in the intestinal wall.

Bariatric by-pass surgeries have thus been remarkably successful in decreasing nutrient intake and nutrient absorption, and have had further beneficial effects that enhance their anti-obesity effect with what appears to be a related but separable anti-diabetic effect. Surgeries such as these, however are extremely costly for the health care system as whole, and carry substantial risk of surgical morbidity and mortality. Even advocates of the use of bariatric surgery for obesity are cautious in recommending surgery as a treatment for diabetes. Clearly, however, diabetes is a major and growing public health problem, and interventions that would bring any of the remarkable effectiveness of bypass surgery but with decreased associated costs and risks would be a highly desirable addition to the currently available treatments for metabolic conditions and diseases such as morbid obesity, metabolic syndrome, and type 2 diabetes.

SUMMARY OF THE INVENTION

Embodiments of the invention include a system and methods of using the devices to ablate tissue in the wall of luminal organs of the gastrointestinal tract of a patient pathophysiological metabolic condition toward the end of alleviating or curing that condition. The method of ablationally treating a target area in gastrointestinal tract wall includes delivering radiofrequency energy from a non-penetrating electrode pattern on an ablation structure to the tissue surface within the target area, the target area being a contiguous radial portion of the gastrointestinal tract. The method further includes controlling the delivery of radiofrequency energy into tissue in three dimensions: controlling energy delivery across the surface area of tissue within the target area, and controlling delivery into the depth of tissue within the target area such that some volume portion of the tissue is ablated and some volume portion of the tissue is not ablated. Embodiments of this type of ablation may be understood as a fractional ablation or a partial ablation within a contiguous target or treatment area, as such, the post-ablationally-treated area of tissue has a mixed pattern of affected tissue and areas of substantially unaffected tissue.

Controlling the delivery of radiofrequency energy across the surface area of tissue within the target area includes delivering sufficient radiofrequency energy to achieve ablation in one portion of the target tissue surface area to achieve ablation, while at the same time, delivering insufficient radiofrequency energy to another portion of the tissue surface area to achieve ablation. Controlling the delivery of radiofrequency energy into the depth of the tissue includes controlling the delivery of radiofrequency energy inwardly from the tissue surface such that sufficient energy to achieve ablation is delivered to some tissue layers and insufficient energy is delivered to other layers to achieve ablation.

In some embodiments of the method, controlling the fraction of the target area surface that receives sufficient radiofrequency energy to achieve ablation includes configuring the electrode pattern such that some spacing between electrodes is sufficiently close to allow conveyance of a given level of energy sufficient to ablate and other spacing between electrodes is insufficiently close to allow conveyance of that level of energy sufficient to ablate.

In other embodiments of the method, controlling the fraction of the target area surface that receives sufficient radiofrequency energy to achieve ablation includes operating the electrode pattern such that the energy delivered between some electrodes is sufficient to ablate and energy sufficient to ablate is not delivered between some electrodes. The electrodes in this pattern are typically distributed at a higher density than in embodiments, as above, where inter-electrode spacing controls the fractional distribution of ablated and non-ablated tissue.

In various embodiments, controlling the delivery of energy into inwardly from the surface of the tissue consists of ablating some portion of tissue within the epithelial layer; in other embodiments it consists of ablating some portion of tissue within the epithelial layer and the lamina propria; in other embodiments, it consists of ablating some portion of tissue within the epithelial layer, the lamina propria, and the muscularis mucosae; in other embodiments, it consists of ablating some portion of tissue within the epithelial layer, the lamina propria, the muscularis mucosae, and the submucosa; and in still other embodiments, it consists of ablating some portion of tissue within the epithelial layer, the lamina propria, the muscularis mucosae, the submucosa, and the muscularis propria. In none of the embodiments, is energy delivered through the wall to reach the level of the serosa.

In various embodiments of the method, the pathophysiological metabolic condition being addressed by the ablational treatment may include any one or more of type 2 diabetes, insulin resistance, obesity, or metabolic syndrome. These embodiments may further include restoring the pathophysiological metabolic condition of the patient toward a normal metabolic condition. Restoring these various metabolic conditions toward a more normal metabolic condition may be reflected in such indicators as decreasing absorption of nutrients, decreasing blood glucose levels, decreasing blood insulin levels, decreasing insulin resistance, decreasing body weight, or decreasing body mass index.

In various embodiments of the method, the ablation target area may includes cells that support or promote the secretion of insulin in the patient, and wherein upon receiving transmitted energy from the ablation structure are rendered at least partially dysfunctional. In some of these embodiments, the cells supporting the effect insulin are endocrine cells; in some embodiments, the cells supporting the effect of insulin are nerve cells.

In some embodiments of the method, the ablation target area includes cells that support or promote the response of the patient to insulin, and wherein upon receiving transmitted energy from the ablation structure are rendered at least partially dysfunctional. In some embodiments, supporting the response to insulin includes any of promoting the greater effectiveness of secreted insulin or decreasing the effect of agents that have an anti-insulin effect. In some embodiments, the cells supporting the effect insulin are endocrine cells. In some embodiments, the cells supporting the effect of insulin are nerve cells.

In various embodiments of the method, the ablation target area is located in the gastric antrum; in some embodiments, the target area is located in the pylorus; in some embodiments of the method, the target area is located in the small intestine, such as in the duodenum or the jejunum.

In various embodiments of the method, controlling the delivery of radiofrequency energy across the tissue surface within the ablation target area and into the depth of tissue within the target area allows achievement of a partial or fractional ablation in tissue layers of the gastrointestinal tract. Thus, in some embodiments, the ablation target area where partial ablation is created is in the epithelial layer of the gastric antrum; in some embodiments, the target area is in epithelial layer of the small intestine, such as in the duodenum or jejunum. In various embodiments of the method, partial ablation in the epithelial layer slows the rate of nutrient absorption through the epithelial layer. In other embodiments, the ablation target area where partial ablation is created includes the muscularis of the gastric antrum, where such ablation causes a slowing of gastric emptying. In other embodiments, the target area for partial ablation includes the muscularis of the pyloris, where such ablation causes a slowing of gastric emptying. And in still other embodiments, the target area for partial ablation includes the muscularis of the duodenum causing a slowing of gastric emptying.

In various embodiments of the method, the ablation has a permanent effect on the function of the target area, while in other embodiments, the ablation has a transient effect on the function of the target area. When the effect is transient, the effect may have a duration that ranges from a period of about one day to about one year. During the time when the function of the target region is transiently affected, the method may further include evaluating the patient for a beneficial therapeutic effect of the ablation. In some embodiments that are transient and a beneficial therapeutic effect is demonstrated, the method may further include repeating the ablation of the target region. In the event of a repeated ablation, the ablation may be performed as either a second transient ablation, or performed to be a permanent ablation.

In some embodiments of the method, the ablational electrode pattern is configured circumferentially through 360 degrees around the ablation structure. In other embodiments that make use of a 360 degree ablation structure, the method may include transmitting energy from the ablation structure asymmetrically through the 360 degree circumference such that ablation is focused within an arc of less that 360 degrees. In other embodiments, the electrode pattern is configured circumferentially through an arc of less than 360 degrees around the ablation structure, such arc, by way example, spanning about 90 degrees or about 180 degrees.

Some embodiments of the method may further include evaluating the target area at a point in time after delivering energy to the target area in order to determine the status of the area. In some embodiments, evaluating step occurs in close time proximity after the delivery of energy, to evaluate the immediate post-treatment status of the site. In other embodiments, the evaluating step may occur at least one day after the delivery of energy, and in fact, may occur at any length of time after the ablational procedure.

In some embodiments, the step of delivering energy is performed one or more times during an ablational procedure. In other embodiments, the ablational procedure may be performed more than once during separate treatment sessions.

In some embodiments, the method of may include deriving energy for transmitting from an energy source that is controlled by a control system; and the energy source may be a generator. By way of the control system, the method may include feedback that control the energy transmission so as to provide a controlled level of any of a specific power, power density, energy, energy density, circuit impedance, or tissue temperature.

In addition to the various method steps summarized above, the method may further include advancing an ablation structure into the alimentary canal, the non-penetrating electrode pattern on the structure, the structure supported on an instrument, positioning the ablation structure adjacent to the target area; and moving the ablation structure toward the surface of the target area to make therapeutic contact on the target area prior to delivering energy. In the context of these method steps, the moving step may include any of inflating a balloon member, expanding a deflection member, moving a deflection member, or expanding an expandable member. The method may also further including a position-locking step following the moving step, in order to secure a therapeutic contact. In one example, the position-locking step may include developing suction between the structure and the ablation site. Prior to the positioning step, the method may still further include an evaluating step in order to determine the status of the target area.

Embodiments of the method further include evaluating the target area prior to the positioning step, in order to determine the status of the target area. Also, when multiple target areas are being treated, the method may include the positioning, moving, and transmitting energy steps to a first target area, and the further include the positioning, moving, and transmitting energy steps to another target area without removing the ablation structure from the patient.

Embodiments of the invention include an ablation system with an electrode pattern that has a plurality of electrodes; a longitudinal support member supporting the electrode pattern; a generator coupled to the plurality of electrodes; and a computer controller in communication with the generator. The controller has programming to direct the generator to deliver energy to the plurality of electrodes, and the programming includes the ability to direct delivery of energy to a subset of the electrodes. The electrodes of the pattern are configured such that, when receiving energy from the generator and in therapeutic contact with a tissue target area, they ablate a portion of tissue in the target area and leave a portion of tissue in the target area non-ablated. In some embodiments, the electrode pattern forms a fully circumferential surface orthogonal to its longitudinal axis, the pattern sized for contacting tissue in a target area within the gastrointestinal tract. In other embodiments, the electrode pattern forms a partially circumferential surface orthogonal to its longitudinal axis, the pattern sized for contacting tissue in a target area within the gastrointestinal tract. The partially-circumferential surface may have any arc of less than 360, but particular embodiments form an arc of about 180 degrees, and some particular embodiments form an arc of about 90 degrees.

In some embodiments of the system, the ablational energy elements, such as electrodes, are distributed into a pattern such that when the programming directs the generator to deliver energy to all the ablational energy elements, the pattern of energy-transmitting elements, when therapeutically contacted to a target tissue area, ablates a portion of tissue within the target area and does not ablate another portion of tissue within the target area. These embodiments typically have electrodes distributed in a relatively dispersed or low-density pattern, as it is the spacing between the electrodes that determines the conveyance or non-conveyance of energy between the electrodes. In other embodiments, the programming directs the generator to deliver energy to a subset of electrode elements that form a pattern which, when therapeutically contacted to a target tissue area, ablates a portion of tissue within the target area and does not ablate another portion of tissue within the target area. These embodiments typically have electrodes distributed in a relatively dense pattern, and the partial activation of a subset or subsets of the dense pattern then approximates or is functionally analogous to the less dense physical pattern, as above, wherein the programming directs delivery of energy to all electrodes.

The portion of the tissue that is ablated by the electrode pattern, whether by the full set of electrodes, or by a subset of electrodes, is rendered at least partially dysfunctional, and that portion of the tissue which is not ablated retains its functionality. In embodiments where nutrient-absorbing epithelial cells are included in the target area, the nutrient-absorbing cells that are ablated are compromised in their ability to absorb nutrients, and the nutrient-absorbing cells that are not ablated retain their nutrient-absorbing functionality. In embodiments where endocrine cells are included in the target area, the endocrine cells that are ablated are compromised in their ability to secrete hormones, and the endocrine cells that are not ablated retain their secrete hormone. In embodiments where nerve cells are included in the target area, the nerve cells that are ablated are compromised in their in synaptic functionality, and the nerve cells that are not ablated retain their synaptic functionality.

BRIEF DESCRIPTION OF THE DRAWINGS

FIG. 1A shows an ablative device within the pylorus. FIG. 1B shows an ablative device within the duodenum. FIG. 1C shows and ablative device within the jejunum.

FIG. 2A shows an ablative device within the gastric antrum. FIG. 2B shows an ablative device within the pylorus. FIG. 2C shows an ablative device within the duodenum.

FIG. 27 is a view of the device wherein an elongated sheath feature is optically transmissive.

FIG. 28 is an enlarged view of the optically transmissive feature of the device.

FIG. 29 is a cross sectional view of the optically transmissive sheath feature of the device shown in FIGS. 27 and 28.

FIG. 34A is a cross sectional view of the device positioned within an endoscope internal working channel wherein an inflatable member feature is in an unexpanded position.

FIG. 34B is a view of the device shown in FIG. 34A wherein the inflatable member feature is in an expanded position.

FIG. 35A is a cross sectional view of the device positioned within an endoscope internal working channel wherein an expandable member feature is in an unexpanded position.

FIG. 35B is a view of the device shown in FIG. 35A wherein the expandable member feature is in an expanded position.

FIG. 36A is a cross sectional view of the device positioned within an endoscope internal working channel wherein an alternative expandable member feature is in an unexpanded position.

FIG. 36B is a view of the device shown in FIG. 36A wherein the expandable member feature is in an expanded position.

FIG. 38 is an illustration of the ablation device of the invention including an alternative deflection member positioned within the lumen of an organ of the gastrointestinal tract in a non-deflected position.

FIG. 39 is an illustration of the device shown in FIG. 38 wherein the deflection member is in a deflected position.

FIGS. 53A and 53B show an electrode array with a striped pattern of alternating positive and negative electrodes operating in a non-fractional manner and the ablation patterns on tissue that can be made from such an operating pattern.

FIGS. 54A and 54B show an electrode array with a striped pattern of alternating positive and negative electrodes operating in a fractional manner and the ablation patterns on tissue that can be made from such an operating pattern.

DETAILED DESCRIPTION OF THE INVENTION

Figure 1A:
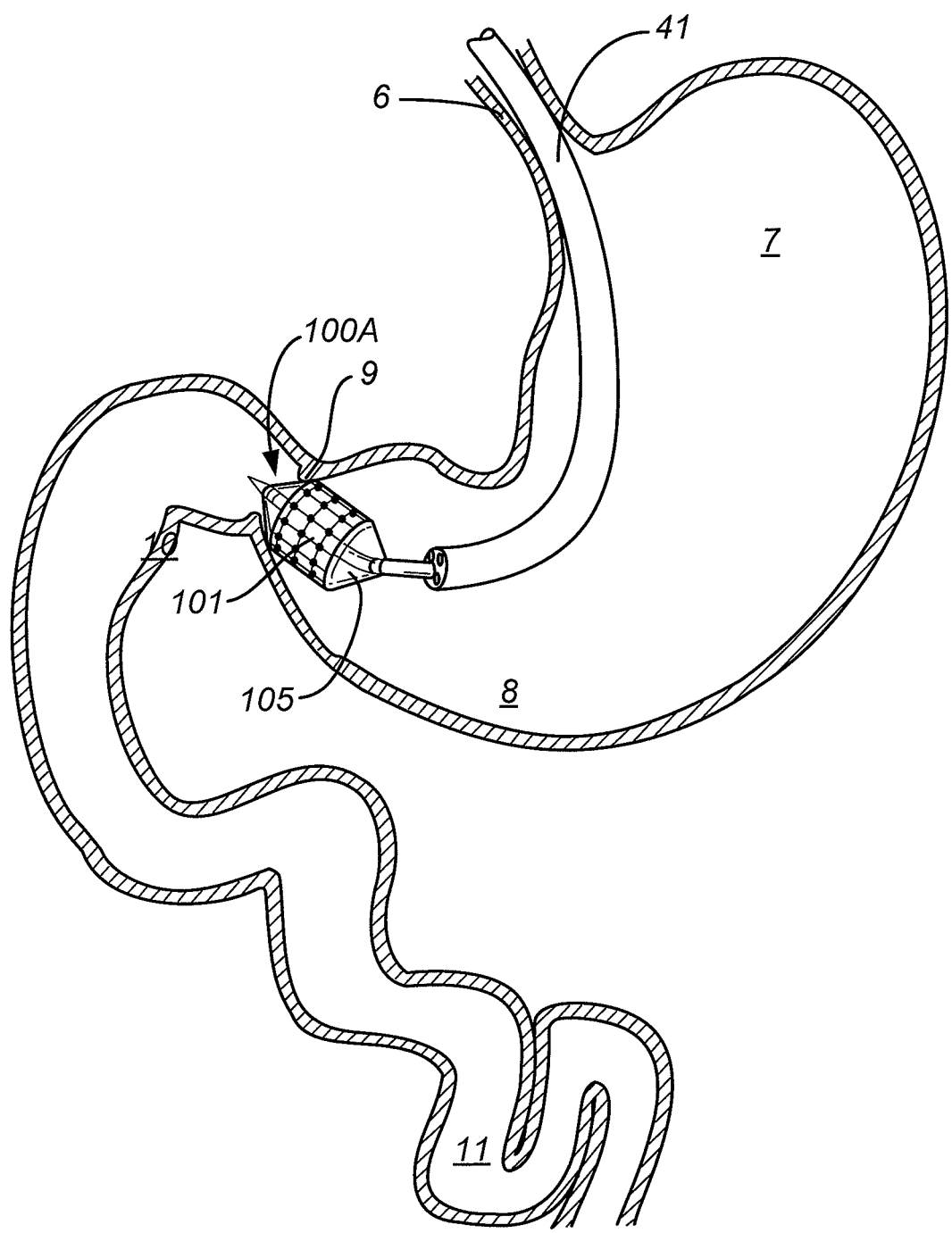
FIGS. 1A-1C provide views of an embodiment of an ablative device with a fully circumferential operating radius in situ, in the alimentary tract.

Ablation in the Gastrointestinal Tract as Treatment for Metabolic Disease

Metabolic conditions such as obesity, diabetes mellitus type 2, and metabolic syndrome tissue can be treated with an ablative technique applied to portions of the wall of the gastrointestinal tract that has a controlled depth of ablation and does not injure the deeper layers of the organ. Ablation technology represents a therapeutic alternative that has been shown to be simple, safe, and effective in treating diseases confined to the epithelial tissue such as Barrett's esophagus and squamous dysplasia of the esophagus, and such therapy thus holds promise as an epithelial layer-based treatment (and in some embodiments, a deeper layer treatment) for metabolic conditions as well. The inventors have made the inventive realization that the success of bariatric surgery, such as Roux-en-Y gastric by-pass operations may provide a rational basis for an ablational approach to an anti-obesity or anti-diabetic therapy. Although not bound by theory, for purpose of understanding the invention, the hypothesis is provided that at least some of the effectiveness that bariatric by-pass surgery has shown is due to a decrease or elimination of hormonal or neural signal(s) that normally would emanate from the stomach, pylorus, duodenum, or jejunum upon exposure to nutrient passage through the gastrointestinal tract. By analogy, therefore, a functional compromise as a result of a well-controlled ablation of one or more of the same organs, even in the presence of nutrient passage, could result in a similar absence of hormonal or neural signals, and by such same absence, obesity, diabetes, and/or metabolic syndrome may be ameliorated or cured.

Determination of an appropriate site for ablational treatment, as well as the amount of ablational energy to be applied during such treatment, follows from the total amount of clinical information that a clinician can gather on a particular patient. Appropriate information to be evaluated may include, for example, the age of the patient, laboratory data on levels of metabolic hormones such as, merely by way of example, any of insulin, glucagon, glucagon-like peptides, insulin-like growth factors, and ghrelin, as well as data on blood glucose levels and glucose tolerance tests. In some embodiments, a preliminary endoscopic examination of the alimentary canal may be appropriate so that any patient-specific features may be mapped out, as well as an evaluation of the general dimensions of the patient's alimentary canal. Such information may be obtained by direct visual observation by endoscopic approaches with optional use of mucosal in-situ staining agents, and may further be accomplished by other diagnostic methods, including non-invasive penetrative imaging approaches such as narrow band imaging from an endoscope. In one aspect, evaluation of a site includes identifying the locale of the site, including its dimensions. In another aspect, evaluation of target tissue includes identifying a multiplicity of sites, if there is more than one site, and further identifying their locale and their respective dimensions. In still another aspect, evaluating target sites may include identifying or grading any pathology within the gastrointestinal tract, particularly any area overlapping or near the areas to be targeted for ablation.

Once target sites for ablation have been identified, target tissue may be treated with embodiments of an inventive ablational device and associated methods as described herein. Evaluation of the status of target tissue sites for ablation, particularly by visualization approaches, may also be advantageously implemented as part of an ablational therapy, as for example, in close concert with the ablation, either immediately before the application of ablational energy (such as radiant energy), and/or immediately thereafter. Further, the treatment site can be evaluated by any diagnostic or visual method at some clinically appropriate time after the ablation treatment, as for example a few days, several weeks, or several few months, or at anytime when clinically indicated following ablational therapy. Any follow-up evaluation that shows either that the therapy was unsatisfactorily complete, or that there is a recovery in the population of cells targeted for ablation, a repetition of the ablational therapy may be indicated.

As described in detail herein, ablational devices have an ablational structure arrayed with energy-transmitting elements such as electrodes. In some embodiments, depending on the type of ablative energy being used in the therapy, the devices may be mounted on, or supported by any appropriate instrument that allows movement of the ablational surface to the local of a target site. Such instruments are adapted in form and dimension to be appropriate for reaching the target tissue site, and may include simple catheters adapted for the purpose; some embodiments of the insertive instrument include endoscopes which in addition to their supportive role, also provide a visualization capability. In some embodiments of the method, an endoscope separate from the supportive instrument may participate in the ablational procedure by providing visual information.

Exemplary embodiments of the inventive device as described herein typically make use of electrodes to transmit radiofrequency energy, but this form of energy transmission is non-limiting, as other forms of energy, and other forms of energy-transmission hardware are included as embodiments of the invention. Ablational energy, as provided by embodiments of the invention, may include, by way of example, microwave energy emanating from an antenna, light energy emanating from photonic elements, thermal energy transmitted conductively from heated ablational structure surfaces or as conveyed directly to tissue by heated gas or liquid, or a heat-sink draw of energy, as provided by cryonic cooling of ablational structure surfaces, or as applied by direct cold gas or fluid contact with tissue.

Embodiments of the ablational device include variations, two of which will be elaborated on below, with regard to the circumferential expanse of the ablational surface to be treated. These and other variation may provide particular advantages depending on the nature, extent, locale, and dimensions of the one or more targeted tissue sites on the wall the alimentary canal. One embodiment of the invention includes a device with an ablational surface that is fully circumferential, i.e., encompassing a radius of 360 degrees, such that a full radial zone within a luminal organ is subject to ablation. Within that zone, ablation may be implemented to a varying degree, depending on the energy output and the pattern of the ablational elements (such as electrodes), but with substantial uniformity within the zone of ablation. This embodiment may be particularly appropriate for treating widespread or diffuse sites within the gastrointestinal tract organ. In another embodiment of the device, the ablational surface of the inventive device is partially circumferential, such that it engages a fraction of the full internal perimeter or circumference of a luminal organ. The fractional portion of the circumference ablated on the inner surface of a luminal organ depends on the size of the luminal organ being treated (radius, diameter, or circumference) and on the dimensions of the ablational surface, as detailed further below. With regard to treating target sites that are small and discrete, the smaller or more discrete ablational surface provided by this latter embodiment may be advantageous.

This type of operation of a circumferential subset of ablation energy elements around a circumferential distribution of elements through 360 degrees is related to the fractional operation of an electrode array, as described below in the section titled "Electrode patterns and control of ablation patterns across the surface area of tissue", where subsets of an array of ablational elements within a relative dense pattern are activated.

Ablation of gastrointestinal tract wall cells may be performed by devices with ablational surface areas that vary in terms of the radial fraction of a luminal surface they ablate in a single transmission of energy, and absolute terms of dimension. Some embodiments of the invention, as mentioned above described in detail below, provide a fully radial surface, with electrodes circumferentially arrayed, that substantially meets the inner surface of a luminal organ, and ablates through that full range of 360 degrees. In FIGS. 1A-1C and 2A-2D, an ablation device of one of two types, 100A (with an ablational surface of 360 degrees) or 100B (with an ablational surface of less than 360 degrees, such as the approximate 90 degree embodiment shown) is supported on an ablation catheter 41. The ablation device (100A or 100B) includes an ablation structure 101. In an embodiment where the ablation is RF-based, the ablation device typically includes an array of electrodes depicted in further detail in other figures, and an inflation member or balloon 105.

Figure 1B:
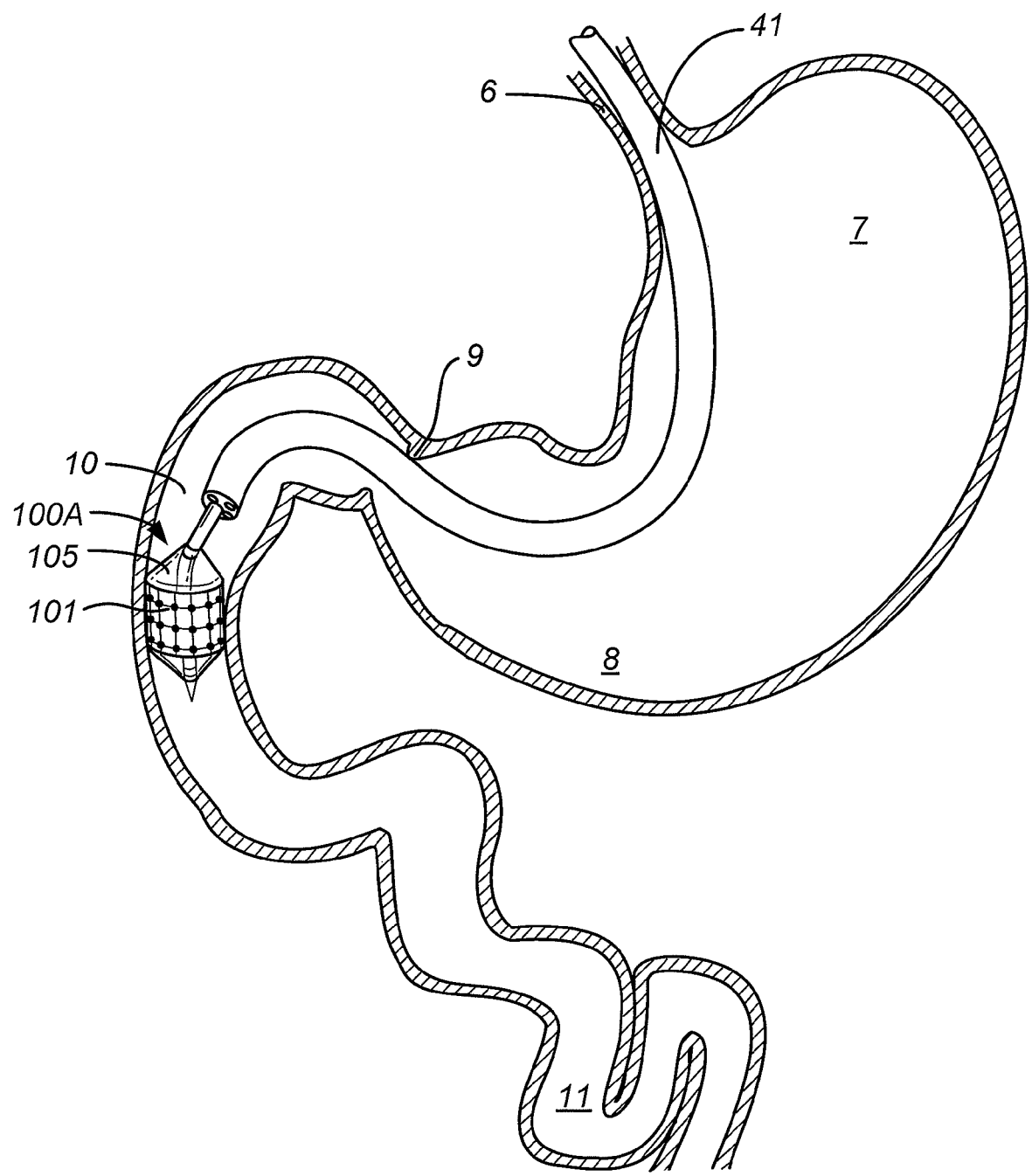
Figure 1C:
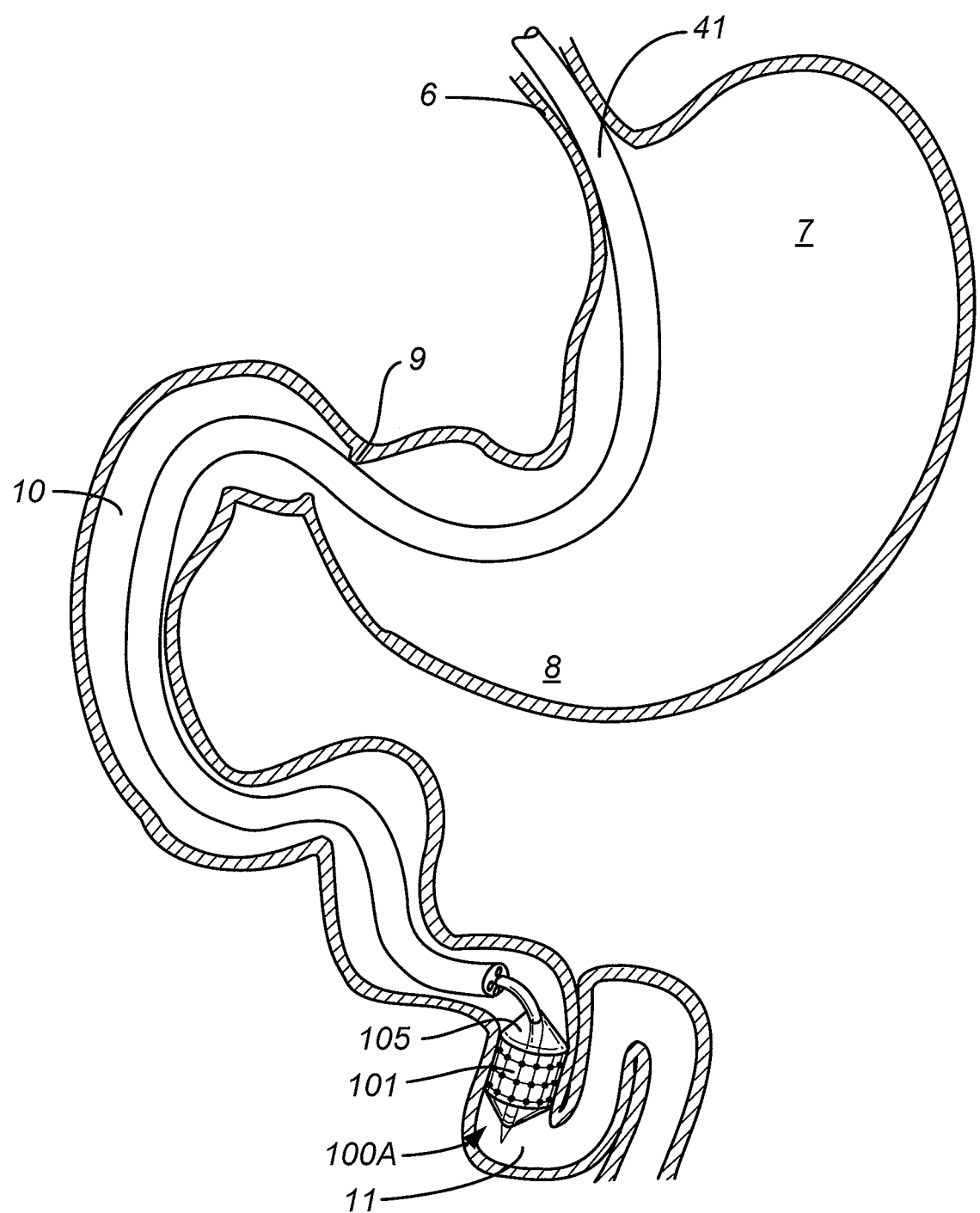

FIGS. 1A-1C provide views of an embodiment of an ablative device with a fully circumferential operating region in situ, in the alimentary tract. The ablative device is supported on the distal end of an elongated shaft 41 of an instrument, has been inserted into the alimentary tract by an oral or nasal entry route, and has been moved into the proximity of an area targeted for treatment. FIG. 1A shows an ablative device having entered the gastrointestinal tract orally, having entered the stomach 7 through the esophagus 6, and now within the pylorus 9. FIG. 1B shows an ablative device within the duodenum 10. FIG. 1C shows and ablative device within the jejunum 11. Some of these embodiments with electrodes arrayed on an 360 degree ablational surface have the ability to selectively activate electrodes, such that energy is delivered across an arc of 360 degrees of the ablational surface, as for example, about 180 degrees, about 90 degrees, about 45 degrees, about 30 degrees, about 10 degrees, or about 5 degrees. Embodiments of these devices also vary in length, along a longitudinal axis. By appropriate sizing in terms of width (or arc) and length along the longitudinal axis, the ablational surface may be sized appropriately for target areas within the gastrointestinal tract.

Figure 2A:
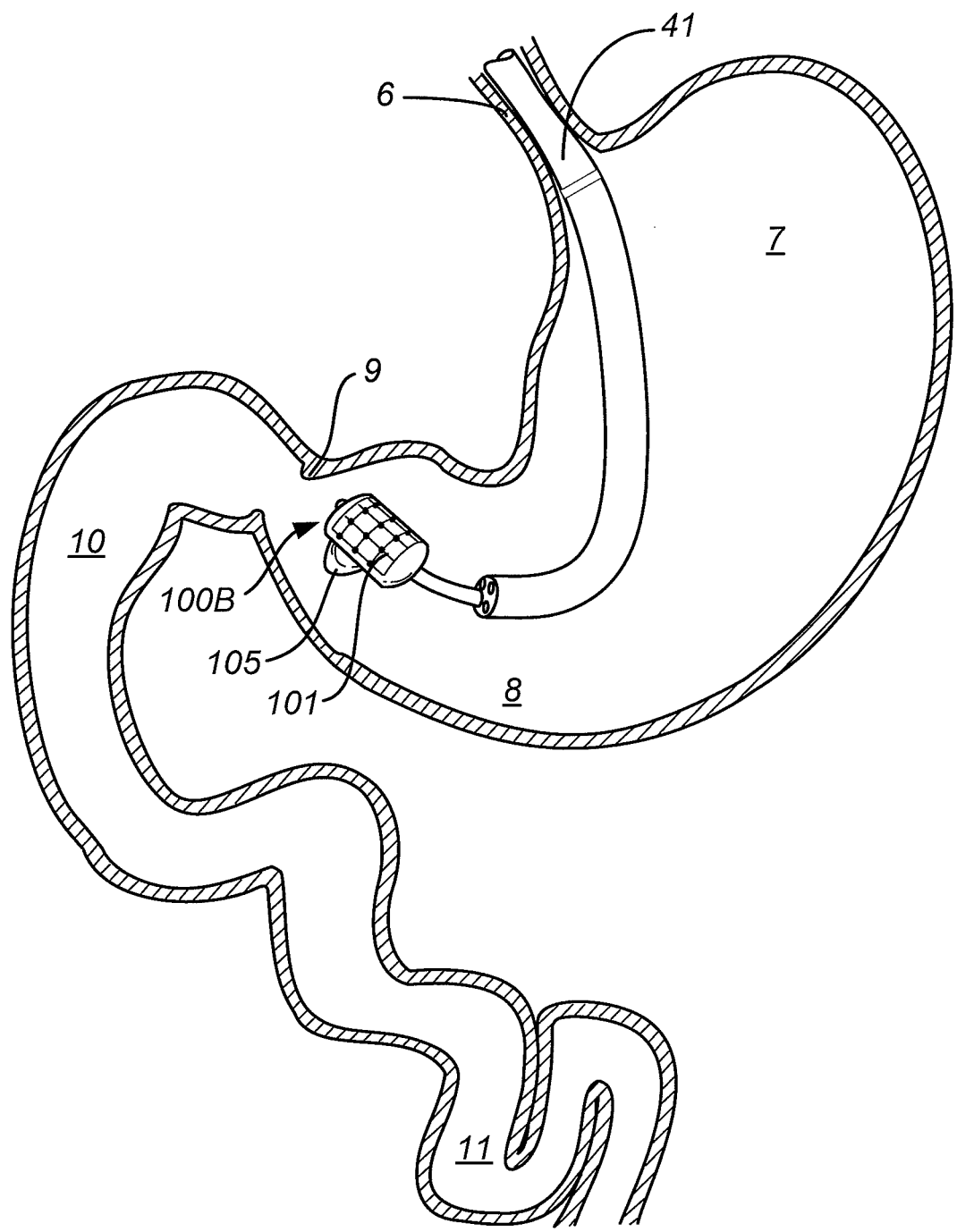
FIGS. 2A-2C provide views of an embodiment of an ablative device with a partially circumferential operating radius in situ, in an alimentary tract.
Figure 2B:
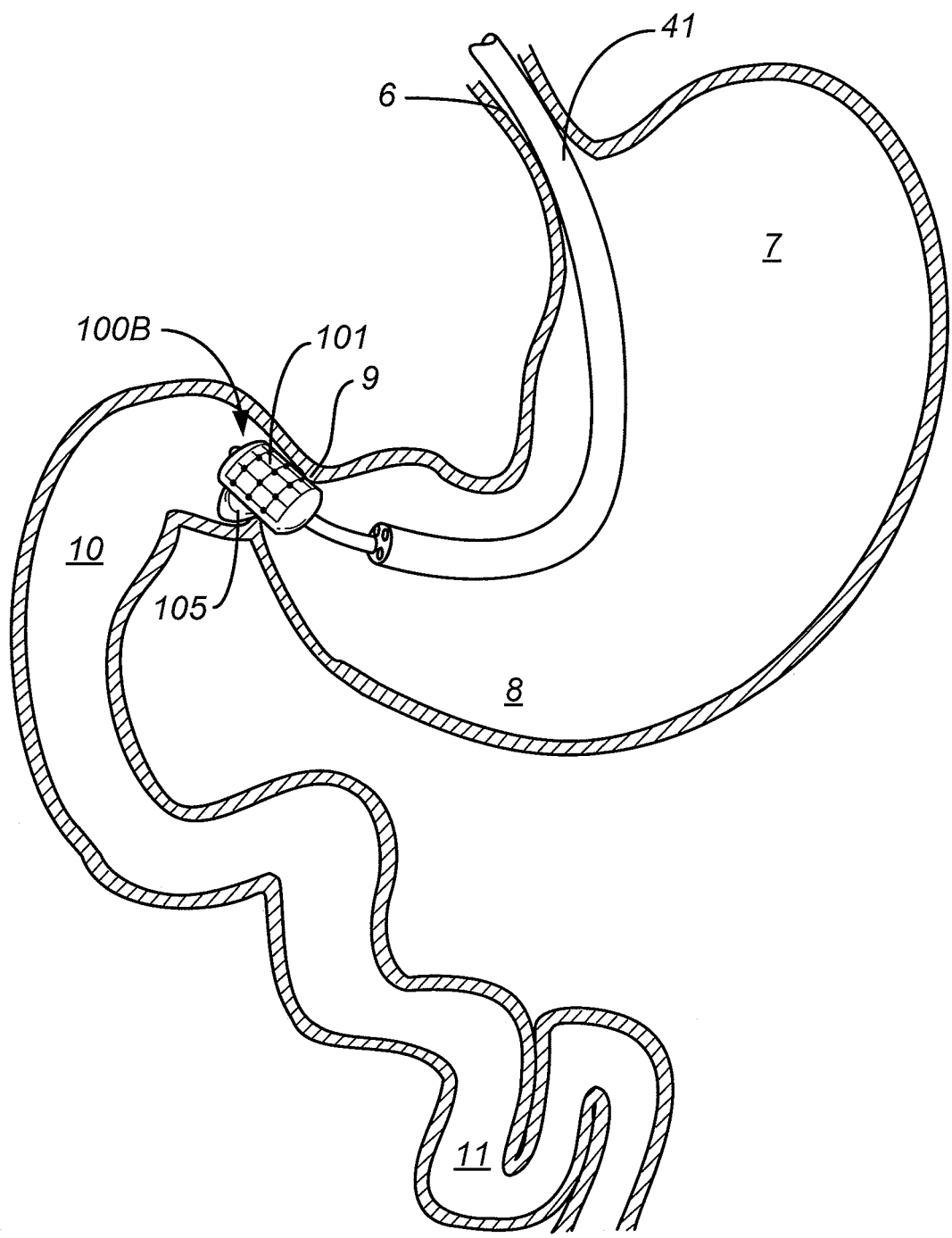
Figure 2C:
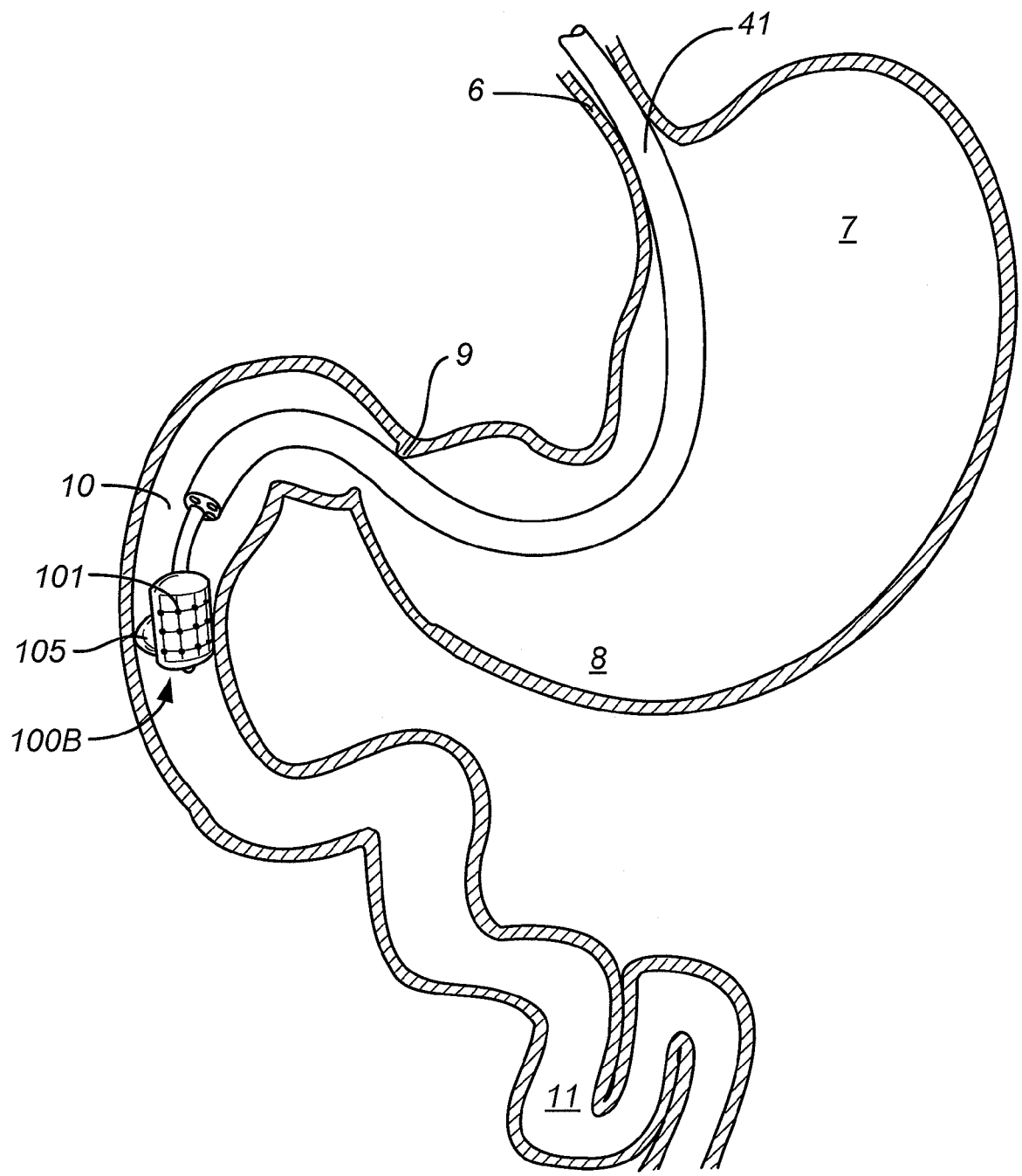
Figure 2D:
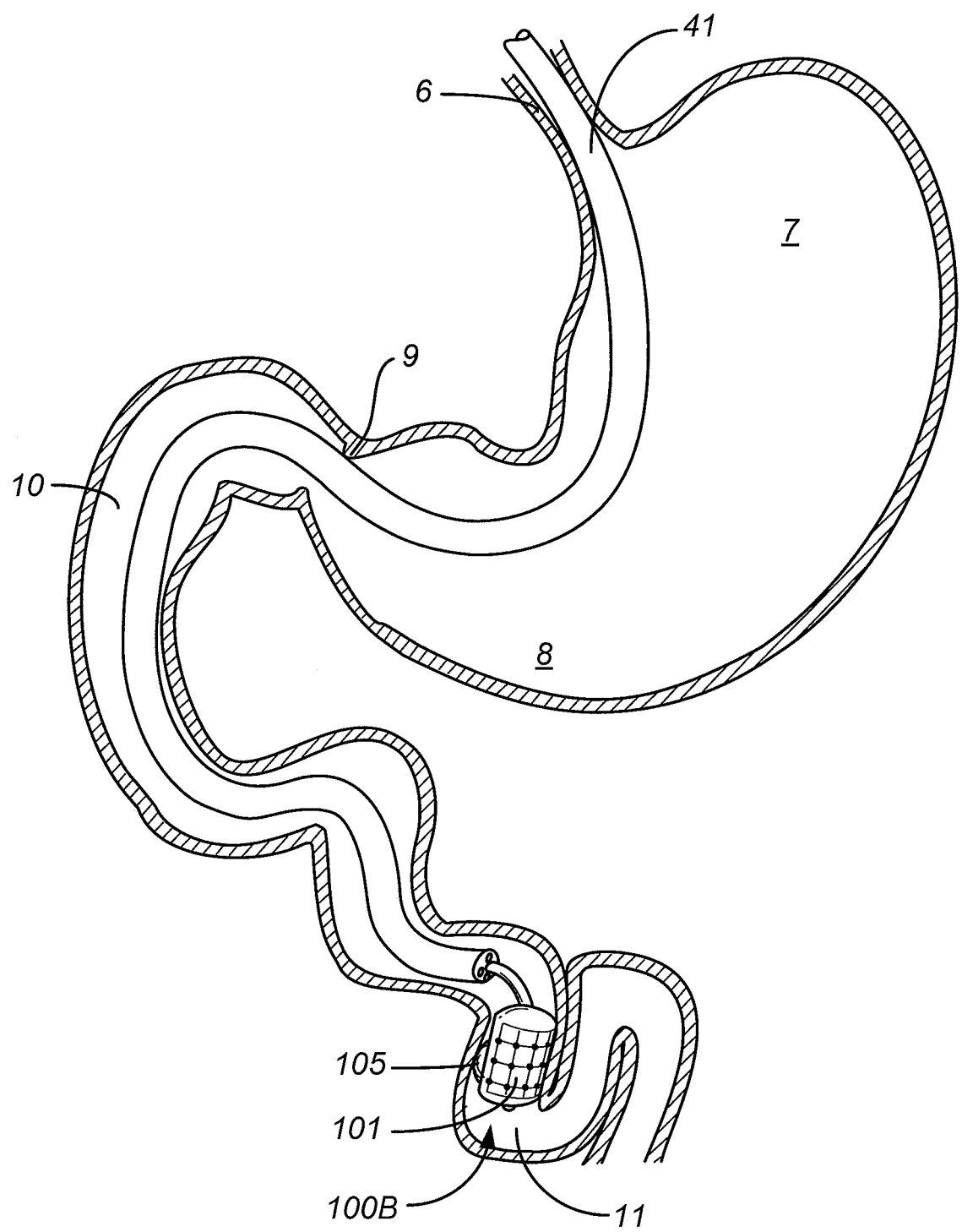
FIG. 2D shows and ablative device within the jejunum.

Other embodiments of the invention provide an ablative surface with an electrode array that addresses a fractional aspect of the inner radius of a luminal organ in any single transmission of energy. These embodiments, as mentioned above, will be described in further detail below, in a section that follows after the description of the 360-degree circumferential embodiment. The ablative device is supported on the distal end of an elongated shaft 41 of an instrument, has been inserted into the alimentary tract by the oral route, and has been moved into the proximity of an area targeted for treatment. FIG. 2A-2C provide views of an embodiment of an ablative device with a partially circumferential operating radius in situ, in an alimentary tract. FIG. 2A shows an ablative device within the gastric antrum 8. FIG. 2B shows an ablative device within the pylorus 9. FIG. 2C shows an ablative device within the duodenum 10. FIG. 2D shows and ablative device within the jejunum 11. The radial portion of a lumen that can be ablationally treated in any single transmission of radiant energy depends on the width of the electrode-covered ablational surface of the embodiment of the device, and the width or diameter of the luminal organ where the treatment site is located. The width of embodiments of the ablational surface, in absolute terms, is described in detail below. The arc of a curved treatment area can be anything less than 360 degrees, however it is typically less than 180 degrees, and more particularly may include a smaller radial expanse such as a arcs of about 5 degrees, about 10 degrees, about 15 degrees, about 30 degrees, about 45 degrees, about 60 degrees, and about 90 degrees.

Figure 3:
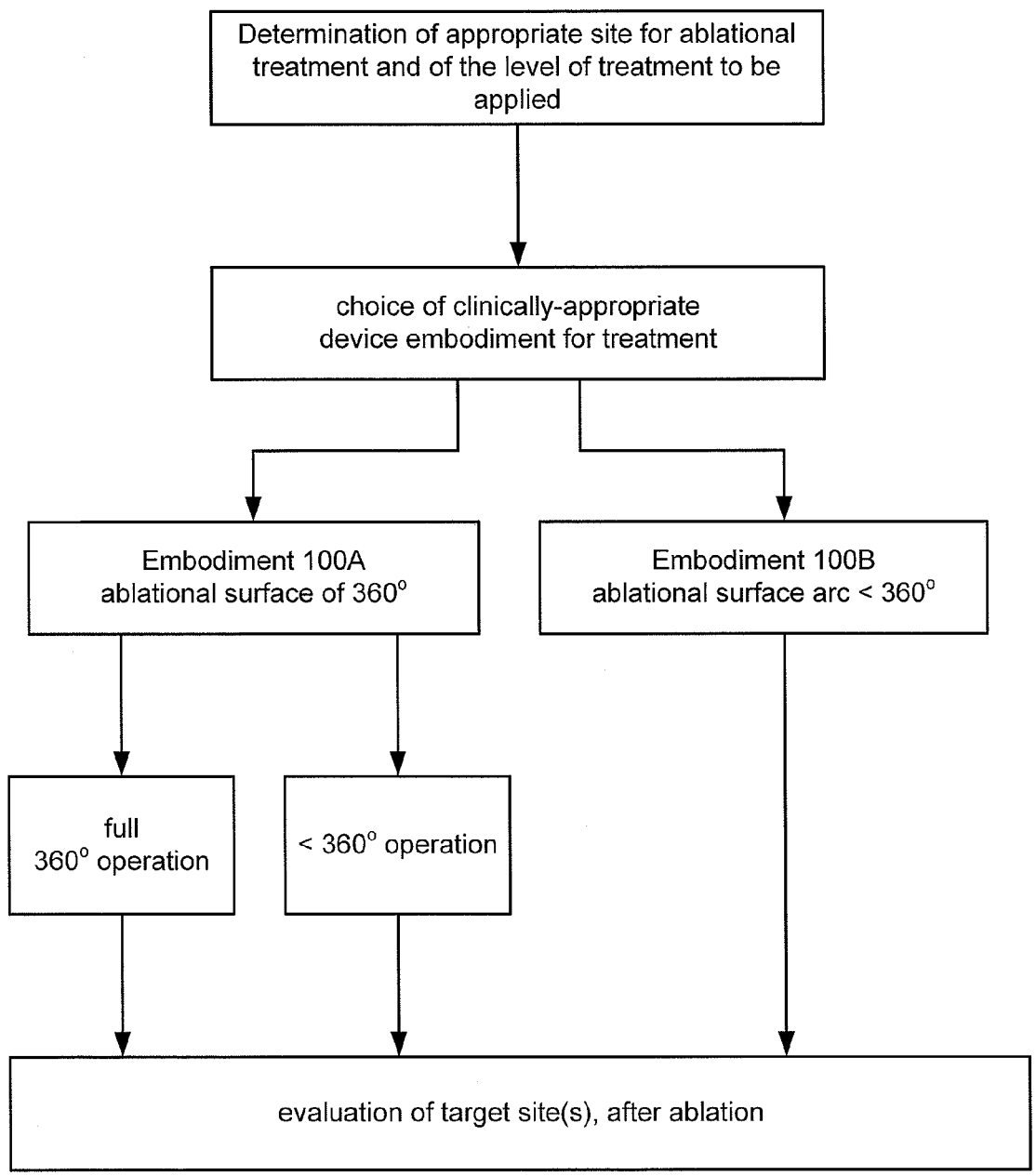
FIG. 3 is a flow diagram depicting an overview of the method, wherein an appropriate site for ablational intervention for the treatment of a metabolic condition such as obesity, diabetes or metabolic syndrome is determined, the level of ablational therapy is determined, and at least preliminary information is gained regarding localization, and clinical judgment is exercised as to which embodiment of the invention is preferable.
Figure 4:
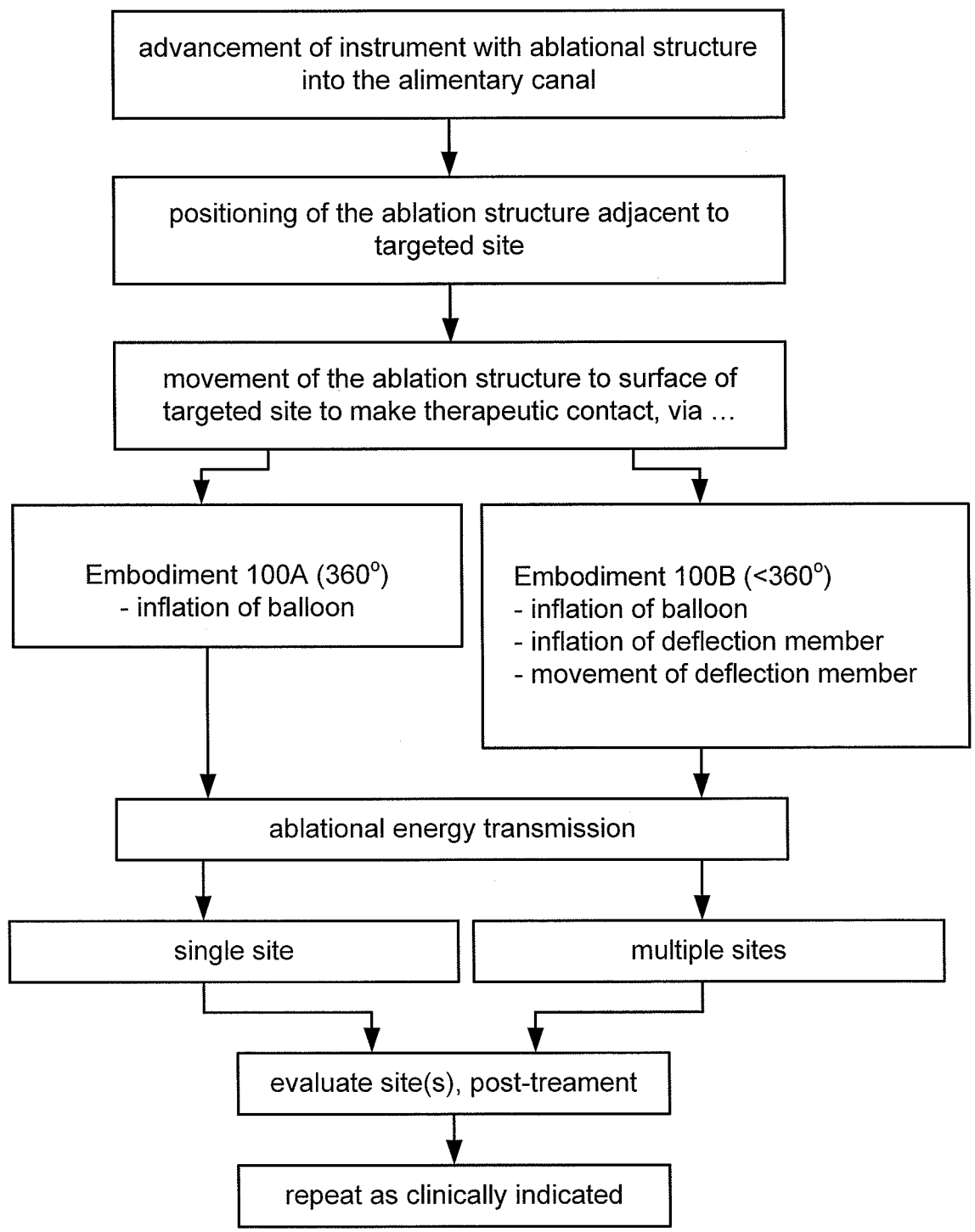
FIG. 4 is a flow diagram depicting the method after the site of ablation of a portion of the gastrointestinal tract has been localized and a choice has been made regarding the preferred ablational device. The method includes an evaluation of the site, including particulars of location, stage, determination of the number of sites, and the dimensions. The method continues with insertion of the instrument and its movement to the locale of the ablational target tissue, the more refined movement of the ablational structure that create a therapeutically effective contact, the emission of ablational radiation and then post-treatment evaluation.

FIGS. 3 and 4 together provide flow diagram depictions of embodiments of the method for ablating tissue in the wall of the alimentary canal or gastrointestinal tract. The diagrams represent common aspects of the embodiments of the method, as delivered by two embodiments of the device, one which has a 360 degree circumferential ablation structure, and one which has an ablation structure comprising an arc of less than 360 degrees.

FIG. 3 is a flow diagram depicting an overview of the method with a focus on patient evaluation and determination of a clinically appropriate site within the alimentary canal for ablational treatment. In another step, a responsible clinician makes an informed choice with regard to the appropriate embodiment with which to treat the patient, i.e., either the device with the 360 electrode array 100A, or the device 100B with the electrodes arrayed in an arc of less than 360 degrees. In the event that the device 100A is chosen for use, another treatment choice may be made between operating the electrodes throughout the 360 degree circumference, or whether to operate a radial subset of the electrode array. In another step, a clinician further considers and makes a determination as to the protocol for ablation, considering the amount of energy to be delivered, the energy density, the duration of time over which energy is to be delivered. These considerations take into the account the surface area to be ablated, the depth of tissue which is to be treated, and the features of the electrode array, whether, for example, it is to be a fractional electrode, and which pattern may be desirable. Regardless of the device chosen, another preliminary step to operating the method may include a closer evaluation of the target tissue site(s) within the alimentary canal. Evaluation of the site may include the performance of any visualization or diagnostic method that provides a detailed census of the number of discrete target tissue sites, their dimensions, their precise locations, and/or their clinical status, whether apparently normal or abnormal. This step is shown following the choice of instrument, but may occur simply in conjunction with diagnosis, or at any point after diagnosis and general localization of the target tissue. In any case, an evaluating step is typically performed prior to ablation, as outlined in the operational steps of the method, as shown in the flow diagram of FIG. 4.

FIG. 4 is a flow diagram depicting the method after the target site within the gastrointestinal tract has been localized and a choice has been made regarding the preferred ablational device. The method includes an evaluation of the site, including particulars of location, stage, determination of the number of sites, and the dimensions, as described above, and using approaches detailed in the references provided in the background, and/or by using whatever further approaches may be known by those practiced in the art. The method continues with insertion of the instrument and the movement of the ablational structure to the locale of the target tissue to be ablated. Subsequently, more refined movements of the ablational structure may be performed that create a therapeutically effective contact between the ablational structure and the target tissue site. In the event that the 360 degree embodiment of the device 100A is chosen, therapeutically effective contact may be made by inflating a balloon underlying the electrode array. In the event that the embodiment chosen is 100B, the device with an electrode surface spanning an arc of less than 360 degrees, movements that bring the ablational surface into therapeutically effective contact may include any of inflation of a balloon, inflation of a deflection member, and/or movement of a deflection member, all of which are described further below.

After therapeutically-effective contact is made, by either device embodiment 100A or 100B, and by whatever type of movement was that was taken, a subsequent step includes the emission of ablational energy from the device. Variations of ablational energy emission may include ablating a single site as well as moving the instrument to a second or to subsequent sites that were identified during the evaluation step. Following the ablational event, a subsequent step may include an evaluation of the treated target site; alternatively evaluation of the consequences of ablation may include the gathering of clinical data and observation of the patient. In the event that an endoscope is included in the procedure, either as the instrument supporting the ablational structure, or as a separate instrument, such evaluation may occur immediately or very soon after ablation, during the procedure, when instruments are already in place. In other embodiments of the invention, the treated site may be evaluated at any clinically appropriate time after the procedure, as for example the following day, or the following week, or many months thereafter. In the event that any of these evaluations show an ablation that was only partially complete, or show an undesired repopulation of targeted cells, the method appropriately includes a repetition of the steps just described and schematically depicted in FIG. 4.

In addition to observation by direct visual approaches, or other diagnostic approaches of site of ablation per se, evaluation of the consequences of ablation may include the gathering of a complete spectrum of clinical and metabolic data from the patient. Such information includes any test that delivers information relevant to the metabolic status of the patient such as the information gathered when determining the appropriateness of ablational intervention, as was made in the first step of FIG. 3.

Some embodiments of the inventive method include ablation interventions that are intended to be mild or partial in nature, and thereby transient. The wall of the gastrointestinal tract is a robust and dynamic biological surface, the cells of the gut are typically fast growing and capable of growing and repopulating areas that are compromised. Embodiments of ablational therapeutic methods as described herein are new and may be expected to be tailored to the particulars of the patient. Thus, some embodiments of the method include treatments that are intended to be transient with transient effects. The transient period, per embodiments of the invention represent a time period during which the metabolic effects of the therapy may be evaluated by diagnostic testing and clinical observations. Based on such observations and clinical data, the ablation may be discontinued (if results are poor, or not-beneficial), or repeated if the results are beneficial. Repeated therapies may be tailored to be more durable. Further, based on results, the ablation parameters may be adjusted, per clinical judgment made by the medical practitioner, or held constant, or ablation may be performed at other sites.

Evaluating the Success of Ablational Treatment for Obesity, Metabolic Syndrome, or Diabetes Restoring the metabolic condition of the patient with a pathophysiological metabolic condition such as obesity, metabolic syndrome, or diabetes toward normal may include any one or more of decreasing absorption of nutrients, decreasing blood glucose levels, decreasing blood insulin levels, decreasing insulin resistance, decreasing body weight, or decreasing body mass index.

Obese patients have a body mass index (BMI) of 30 kg/m2 or more. A statistically significant and reproducible reduction in BMI compared to levels prior to treatment per embodiments of this invention of any magnitude would be considered an indication of therapeutic benefit. Generally, non-obese patients have a BMI that is less than 30 kg/m2.

Fasting blood glucose levels of diabetic patients are typically greater than 125 mg/dL. A statistically significant and reproducible reduction in fasting glucose compared to levels prior to treatment per embodiments of this invention to of any magnitude would be considered an indication of therapeutic benefit. Non-diabetic patients typically have fasting glucose levels of less than 125 mg/dL, for example ranging from about 70 mg/dL to 110 mg/dL.

When patients undergo an oral glucose tolerance test, they drink a standard amount of a glucose solution and their blood is typically drawn five times over a period of 3 hours. Diabetic patients typically have a blood glucose level in the range of 180 mg/dL or higher. Patients with an impaired glucose tolerance have a blood glucose level greater than 140 mg/dL. A normal, non-diabetic patient has a blood glucose level less than or equal to 110 mg/dL. A reproducible reduction in the blood glucose level at 2 hours following an oral glucose test compared to levels prior to treatment per embodiments of this invention of any magnitude would be considered an indication of therapeutic benefit.

Hemoglobin A1C (glycosylated hemoglobin) levels are used as an approach to evaluating blood glucose levels integrated over time. Diabetic patients typically have hemoglobin A1C values 7% and higher, for example up 11% or 12%. Normal patients have values less than about 6%. Any reduction in hemoglobin A1C values after treatment that are statistically significant and reproducible would be considered an indication of therapeutic benefit.

High levels of serum insulin and the pathophysiological condition of insulin resistance are closely linked and occur in a state known as metabolic syndrome as well in diabetes. Insulin levels of greater than 60 pmol/L are generally considered evidence of insulin resistance. Any reduction in serum insulin levels that are significant and repeatable compared to insulin levels prior to treatment per embodiments of this invention would be considered an indication of therapeutic benefit. The gold standard for measuring insulin resistance is performed by a method known as the "hyperinsulinemic euglycemic clamp". This method is generally used in research studies, and not typically performed for routine clinical diagnostic purposes. Other methods such as the "modified insulin suppression test", the "homeostatic model assessment" (HOMA) and the "Quantitative Insulin Sensitivity Check Index" (QUICKI) are more commonly employed. All of these methods test the efficacy of insulin in reducing the level of glucose that has been infused into the patient. Any reduction in the level of insulin resistance, as measured these methods or similar methods, that is significant and reproducible in a patient after ablational therapy as provided by embodiments of the invention may be considered an indication of therapeutic benefit.

Device and Method for 360 Degree Circumferential Ablation

Methods for accomplishing ablation of targeted cells within the gastrointestinal tract according to this invention include the emission of radiant energy at conventional levels to accomplish ablation of epithelial and with or without deeper levels of tissue injury, more particularly to remove or functionally compromise cells that are involved in the sensation of satiety or the regulation of metabolic hormones such as insulin. In one embodiment, as shown in FIGS. 1A-1C, an elongated flexible shaft 41 is provided for insertion into the body in any of various ways selected by a medical care provider. The shaft may be placed endoscopically, e.g. passing through the mouth and esophagus and then further into the gastrointestinal tract, or it may be placed surgically, or by any other suitable approach. In this embodiment, radiant energy distribution elements or electrodes on an ablation structure 101 are provided at a distal end of the flexible shaft 41 to provide appropriate energy for ablation as desired. In typical embodiments described in this section, the radiant energy distribution elements are configured circumferentially around 360 degrees. Alternatively to using emission of RF energy from the ablation structure, alternative energy sources can be used with the ablation structure to achieve tissue ablation and may not require electrodes. Such energy sources include: ultraviolet light, microwave energy, ultrasound energy, thermal energy transmitted from a heated fluid medium, thermal energy transmitted from heated element(s), heated gas such as steam heating the ablation structure or directly heating the tissue through steam-tissue contact, light energy either collimated or non-collimated, cryogenic energy transmitted by cooled fluid or gas in or about the ablation structure or directly cooling the tissue through cryo fluid/gas-tissue contact. Embodiments of the system and method that make use of these aforementioned forms of ablational energy include modifications such that structures, control systems, power supply systems, and all other ancillary supportive systems and methods are appropriate for the type of ablational energy being delivered.

In one embodiment the flexible shaft comprises a coaxial cable surrounded by an electrical insulation layer and comprises a radiant energy distribution elements located at its distal end. In one form of the invention, a positioning and distending device around the distal end of the instrument is of sufficient size to contact and expand the walls of the gastrointestinal tract lumen or organ in which it is placed (e.g. the gastric antrum, the pylorus, the duodenum, or jejunum) both in the front of the energy distribution elements as well as on the sides of the energy distribution elements. For example, the distal head of the instrument can be supported at a controlled distance from the wall of the gastrointestinal tract lumen or organ by an expandable balloon or inflation member 105A, such that a therapeutically-effective contact is made between the ablation structure and the target site so as to allow regulation and control the amount of energy transferred to the target tissue within the lumen when energy is applied through the electrodes. The balloon is preferably bonded to a portion of the flexible shaft at a point spaced from the distal head elements.

Another embodiment comprises using the distending or expandable balloon member as the vehicle to deliver the ablation energy. One feature of this embodiment includes means by which the energy is transferred from the distal head portion of the invention to the membrane comprising the balloon member. For example, one type of energy distribution that may be appropriate and is incorporated herein in its entirety is shown in U.S. Pat. No. 5,713,942, in which an expandable balloon is connected to a power source that provides radio frequency power having the desired characteristics to selectively heat the target tissue to a desired temperature. The balloon 105 of the current invention may be constructed of an electroconductive elastomer such as a mixture of polymer, elastomer, and electroconductive particles, or it may comprise a nonextensable bladder having a shape and a size in its fully expanded form which will extend in an appropriate way to the tissue to be contacted. In another embodiment, an electroconductive member may be formed from an electroconductive elastomer wherein an electroconductive material such as copper is deposited onto a surface and an electrode pattern is etched into the material and then the electroconductive member is attached to the outer surface of the balloon member. In one embodiment, the electroconductive member, e.g. the balloon member 105, has a configuration expandable in the shape to conform to the dimensions of the expanded (not collapsed) inner lumen of the human lower gastrointestinal tract. In addition, such electroconductive member may consist of a plurality of electrode segments arrayed on an ablation structure 101 having one or more thermistor elements associated with each electrode segment by which the temperature from each of a plurality of segments is monitored and controlled by feedback arrangement. In another embodiment, it is possible that the electroconductive member may have means for permitting transmission of microwave energy to the ablation site. In yet another embodiment, the distending or expandable balloon member may have means for carrying or transmitting a heatable fluid within one or more portions of the member so that the thermal energy of the heatable fluid may be used as the ablation energy source.

A preferred device, such as that shown in FIGS. 1A-1C, includes steerable and directional control means, a probe sensor for accurately sensing depth of cautery, and appropriate alternate embodiments so that in the event of a desire not to place the electroconductive elements within the membrane forming the expandable balloon member it is still possible to utilize the balloon member for placement and location control while maintaining the energy discharge means at a location within the volume of the expanded balloon member, such as at a distal energy distribution head of conventional design.

In one embodiment, the system disclosed herein may be utilized as a procedural method of treating metabolic diseases or conditions such as obesity, diabetes mellitus type 2, or metabolic syndrome. This method includes determination of the appropriate target sites for ablation within the gastrointestinal tract in order to ameliorate or eliminate symptoms of metabolic disease, as well as the appropriate treatment device, and the parameters of the ablational energy to be distributed at the target site. After determining that the portion or portions of the gastrointestinal tract wall having this tissue that is targeted either for full or partial ablation, the patient is prepared for a procedure in a manner appropriate according to the embodiment of the device to be utilized. Then, the practitioner inserts, in one embodiment, via endoscopic access and control, the ablation device shown and discussed herein through the mouth of the patient. Further positioning of portions of the device occurs as proper location and visualization identifies the ablation site in the gastrointestinal tract. Selection and activation of the appropriate quadrant(s) or portion(s)/segment(s) on the ablation catheter member is performed by the physician, including appropriate power settings according to the depth of cautery desired. Additional settings may be necessary as further ablation is required at different locations and/or at different depths within the patient's gastrointestinal tract. Following the ablation, appropriate follow-up procedures as are known in the field are accomplished with the patient during and after removal of the device from the gastrointestinal tract. The ablation treatment with ultraviolet light may also be accompanied by improved sensitizer agents, such as hematoporphyrin derivatives such as Photofrine™ porfimer sodium, registered trademark of Johnson & Johnson Corporation, New Brunswick, N.J.

In yet another method of the invention, the practitioner may first determine the length of the portion of the gastrointestinal tract requiring ablation and then may choose an ablation catheter from a plurality of ablation catheters of the invention, each catheter having a different length of the electrode member associated with the balloon member. For example, if the practitioner determines that 1 centimeter of the gastrointestinal tract surface required ablation, an ablation catheter having 1 centimeter of the electrode member can be chosen for use in the ablation. The length of the electrode member associated with the balloon member can vary in length from 1 to 10 cm.

In yet another embodiment, a plurality of ablation catheters wherein the radiant energy distribution elements are associated with the balloon member can be provided wherein the diameter of the balloon member when expanded varies from 12 mm to 40 mm. In this method, the practitioner will choose an ablation catheter having a diameter when expanded which will cause the gastrointestinal tract to stretch and the mucosal layer to thin out, thus, reducing or occluding blood flow at the site of the ablation. It is believed that by reducing the blood flow in the area of ablation, the heat generated by the radiant energy is less easily dispersed to other areas of the target tissue thus focusing the energy to the ablation site.

One approach a practitioner may use to determine the appropriate diameter ablation catheter to use with a particular patient is to use in a first step a highly compliant balloon connected to a pressure sensing mechanism. The balloon may be inserted into a luminal organ within the gastrointestinal tract and positioned at the desired site of the ablation and inflated until an appropriate pressure reading is obtained. The diameter of the inflated balloon may be determined and an ablation device of the invention having a balloon member capable of expanding to that diameter chosen for use in the treatment. In the method of this invention, it is desirable to expand the expandable electroconductive member such as a balloon sufficiently to occlude the vasculature of the submucosa, including the arterial, capillary or venular vessels. The pressure to be exerted to do so should therefore be greater than the pressure exerted by such vessels.

Figure 5:
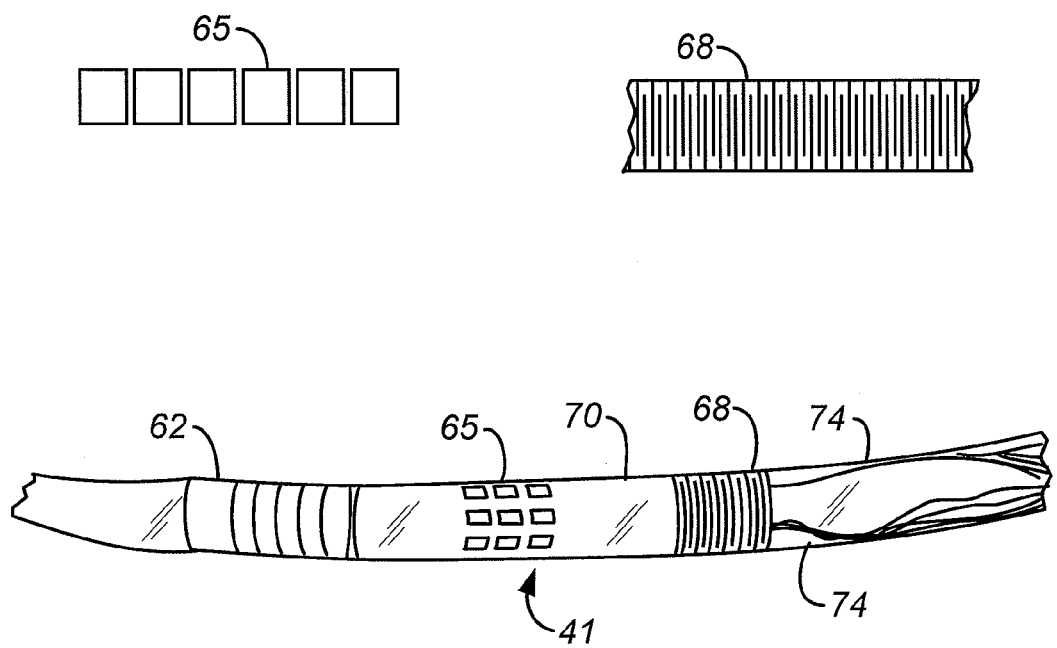
FIG. 5 is a view of an embodiment of an ablative device with a fully circumferential operating radius.
Figure 6:
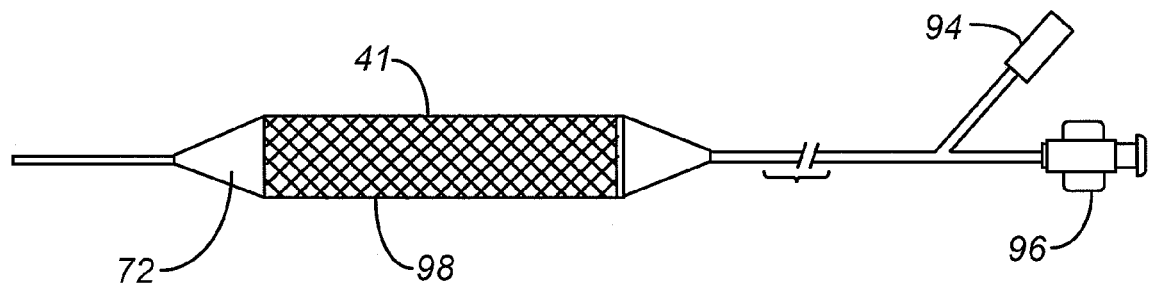
FIG. 6 is a view of an embodiment of an ablative device with a fully circumferential operating radius, with a balloon member in an expanded configuration.
Figure 7A:
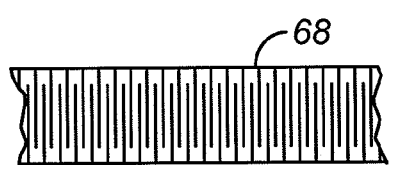
FIGS. 7A-7C show the electrode patterns of the device of FIG. 5.
Figure 7B:
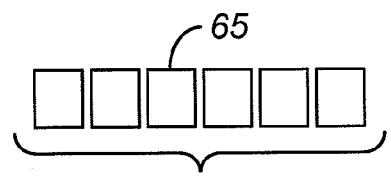
Figure 7C:
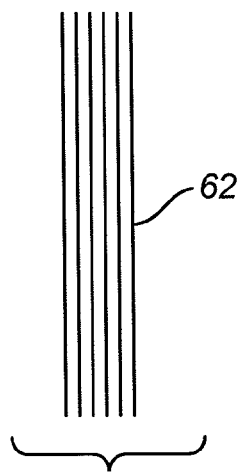
Figure 8A:
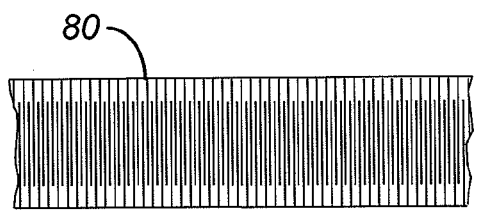
FIGS. 8A-8D show electrode patterns that may be used with embodiments of the ablative device with a fully circumferential operating radius.
Figure 8B:
Figure 8C:
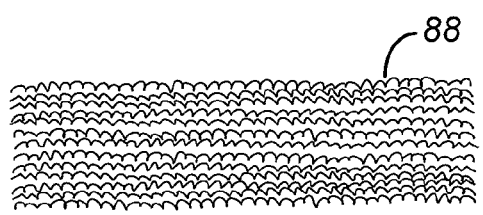
Figure 8D:
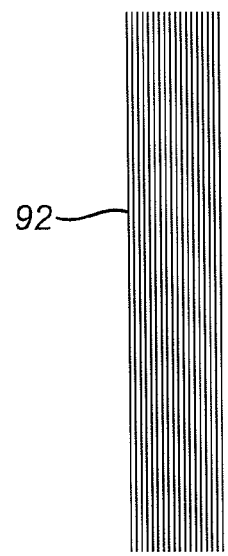

Electrode Patterns and Control of Ablation Patterns Across the Surface Area of Tissue Some aspects of embodiments of the ablational device and methods of use will now be described with particular attention to the electrode patterns present on the ablation structure. The device used is shown schematically in FIGS. 5-7. As shown in FIG. 6, the elongated flexible shaft 41 is connected to a multi-pin electrical connector 94 which is connected to the power source and includes a male luer connector 96 for attachment to a fluid source useful in expanding the expandable member. The elongated flexible shaft has an electrode 98 wrapped around the circumference. The expandable member of the device shown in FIGS. 5 and 6 further includes three different electrode patterns, the patterns of which are represented in greater detail in FIGS. 7A-7C. Typically, only one electrode pattern is used in a device of this invention, although more than one may be included. In this particular device, the elongated flexible shaft 41 comprises six bipolar rings 62 with about 2 mm separation at one end of the shaft (one electrode pattern), adjacent to the bipolar rings is a section of six monopolar bands or rectangles 65 with about 1 mm separation (a second electrode pattern), and another pattern of bipolar axial interlaced finger electrodes 68 is positioned at the other end of the shaft (a third electrode pattern). In this device, a null space 70 is positioned between the last of the monopolar bands and the bipolar axial electrodes. The catheter used in the study was prepared using a polyimide flat sheet of about 1 mil (0.001") thickness coated with copper. The desired electrode patterns were then etched into the copper.

The electrode patterns of the invention may vary; other possible electrode patterns are shown in FIGS. 8A-8D as 80, 84, 88, and 92, respectively. Pattern 80 is a pattern of bipolar axial interlaced finger electrodes with about 0.3 mm separation. Pattern 84 includes monopolar bands with 0.3 mm separation. Pattern 88 is that of electrodes in a pattern of undulating electrodes with about 0.25 mm separation. Pattern 92 includes bipolar rings with about 0.3 mm separation. In this case the electrodes are attached to the outside surface of an esophageal dilation balloon 72 having a diameter of about 18 mm. The device may be adapted to use radio frequency by attaching wires 74 as shown in FIG. 5 to the electrodes to connect them to the power source.

The preceding electrode array configurations are described in the context of an ablation structure with a full 360 degree ablation surface, but such patterns or variants thereof may also be adapted for ablation structures that provide energy delivery across a surface that is less than completely circumferential, in structures, for example, that ablate over any portion of a circumference that is less than 360 degrees, or for example structures that ablate around a radius of about 90 degrees, or about 180 degrees.

Embodiments of the ablation system provided herein are generally characterized as having an electrode pattern that is substantially flat on the surface of an ablation support structure and which is non-penetrating of the tissue that it ablates. The electrode pattern forms a contiguous treatment area that comprises some substantial radial aspect of a luminal organ; this area is distinguished from ablational patterns left by electrical filaments, filament sprays, or single wires. In some embodiments of the invention the radial portion may be fully circumferential; the radial portion of a luminal organ that is ablated by embodiments of the invention is function of the combination of (1) the circumference of the organ, which can be large in the case of stomach, and small when in the case of the pylorus or a region in the small intestine, and (2) the dimensions of the electrode pattern. Thus, at the high end, as noted, the radial expanse of a treatment area may be as large as 360 degrees, and as small as about 5 to 10 degrees, as could be the case in a treatment area within the stomach.

Embodiments of the ablational system and method provided are also characterized by being non-penetrating. Ablational radiofrequency energy is delivered from the flat electrode pattern as it makes therapeutic contact with the tissue surface of a treatment area, as described elsewhere in this application; and from this point of surface contact, energy is directly inwardly to underlying tissue layers.

Embodiments of the ablational system and method provided herein are further characterized by the electrode pattern being configured such that only a portion of the tissue surface receives sufficient radiofrequency energy to achieve ablation and another portion of the surfaces receives insufficient energy to achieve ablation. The system and method are further configured to control the delivery of radiofrequency energy inwardly from the tissue surface such that depth of tissue layers to which energy sufficient for ablation is delivered is controlled.

Controlling the fraction of the tissue surface target area that is ablated comes about by having some fraction of the tissue ablated, at least to some degree, and having some fraction of the surface within the target area emerge from the treatment substantially free of ablation. The ability to control the ratio of ablated and non-ablated surface provides substantial benefit to the treatment. The ablational target areas in this method, after all, are not cancerous, in which case their complete ablation may be desired, and in fact the target areas may not be abnormal in any sense. The ablational treatment, per embodiments of this invention, is directed not necessarily toward correcting any defect of the target tissue, but rather toward a larger therapeutic end, where, in fact, that end is served by creation of a modulated dampening of the normal function of the target area. It is not likely, for example, when treating a metabolic condition such as obesity or diabetes, that it is desirable to render a complete ablation, it is far more likely that what is desired is a modulated approach, where a varying degree of dysfunction can be provided, without substantially damaging the organ, or a particular layer of the organ. Stated in another way, it is generally desirable for the health of the organ within which the target area is located, and for the health of the individual as a whole, that some degree of normal functioning remain after ablation.

By way of an illustrative example as to what is desirable and being provided by the invention, the organ in which the ablation target area is located can be appreciated as a population of particular target cells within the tissue of the target area, which can function, based on their health, at a functional capacity at some low threshold of 20%, for example, when in poor condition, and at 100%, when in optimal condition. The object of the ablational treatment provided herein, within this example by analogy is not to render the full population of cells to be dysfunctional and operating at 50% capacity. The object of the invention is to have some fraction of the cells within the population, post-ablational treatment, to remain fully functional, operating at about 100% capacity, and to have some remaining fraction operating at a range of lower capacity.

Controlling the fraction of the tissue surface target area that is ablated, per embodiments of the invention, is provided by various exemplary approaches: for example, by (1) the physical configuration of electrode pattern spacing in a comparatively non-dense electrode pattern, and by (2) the fractional operation of a comparatively dense electrode array, in a billboard-like manner. Generally, creating a fractional ablation by physical configuration of the electrode pattern includes configuring the electrode pattern such that some of the spacing between electrodes is sufficiently close that the conveyance of a given level of energy between the electrodes sufficient to ablate tissue is allowed, and other spacing between electrodes is not sufficiently close enough to allow conveyance of the level of energy sufficient to ablate. Embodiments of exemplary electrode patterns that illustrate this approach to creating fractional ablation are described below, and depicted in FIGS. 48-50. The creation of an ablation pattern by activating a subset of electrodes represents an operation of the inventive system and method which is similar to the described above, wherein an ablational structure with a fully circumferential pattern of electrodes can be operated in a manner such that only a radial fraction of the electrodes are operated.

The ablation system of the invention includes an electrode pattern with a plurality of electrodes and a longitudinal support member supporting the electrode pattern, as described in numerous embodiments herein. Energy is delivered to the electrodes from a generator, and the operation of the generator is controlled by a computer controller in communication with the generator, the computer controller controlling the operating parameters of the electrodes. The computer controller has the capability of directing the generator to deliver energy to all the electrodes or to a subset of the electrodes. The controller further has the ability to control the timing of energy delivery such that electrodes may be activated simultaneously, or in subsets, non-simultaneously. Further, as described elsewhere, the electrodes may be operated in a monopolar mode, in a bipolar mode, or in a multiplexing mode. These various operating approaches, particularly by way of activating subsets of electrodes within patterns, allow the formation of patterns that, when the pattern is in therapeutic contact with a target surface, can ablate a portion of tissue in the target area, and leave a portion of the tissue in the target area non-ablated.

Generally, creating a fractional ablation by an operational approach with a comparatively dense electrode array includes operating the electrode pattern such that the energy delivered between some of the electrodes is sufficient to ablate, whereas energy sufficient to ablate is not delivered between some of the electrodes. Embodiments of exemplary electrode patterns that illustrate this approach to creating fractional ablation are described below, and depicted in FIGS. 51-54.

Another aspect of controlling the fraction of tissue ablation, per embodiments of the invention, relates to controlling the depth of ablation into tissue layers within the target area. Energy is delivered inwardly from the surface, thus with modulated increases in energy delivery, the level of ablation can be controlled such that, for example, the ablated tissue may consist only of tissue in the epithelial layer, or it may consist of tissue in the epithelial layer and the lamina propria layers, or it may consist of tissue in the epithelial, lamina propria and muscularis mucosal layers, or it may consist of tissue in the epithelial, lamina propria, muscularis mucosa, and submucosal layers, or it may consist of tissue in the epithelial layer, the lamina propria, the muscularis mucosae, the submucosa, and the muscularis propria layers. In no instance is ablational energy delivered to the serosal layer of the gastrointestinal tract.

Figure 48A:
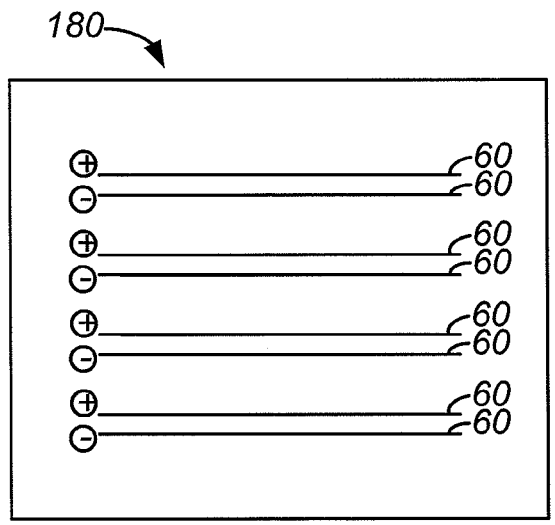
FIGS. 48A-48D show an electrode array with a striped pattern for a fractional ablation and the ablation patterns on tissue that can be made from such a pattern.
Figure 48B:
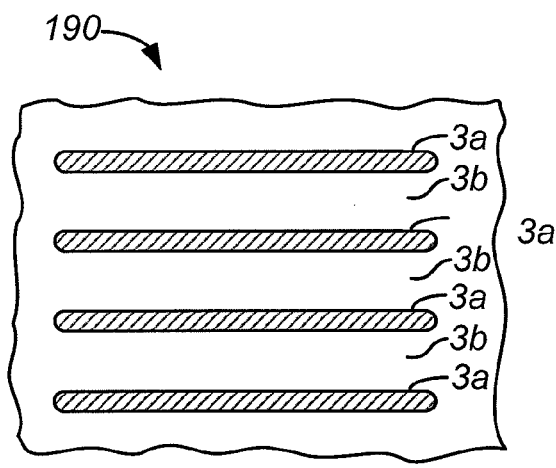
Figure 48C:
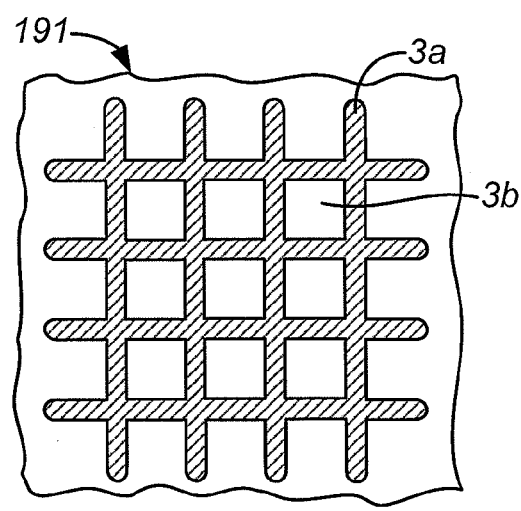
Figure 48D:
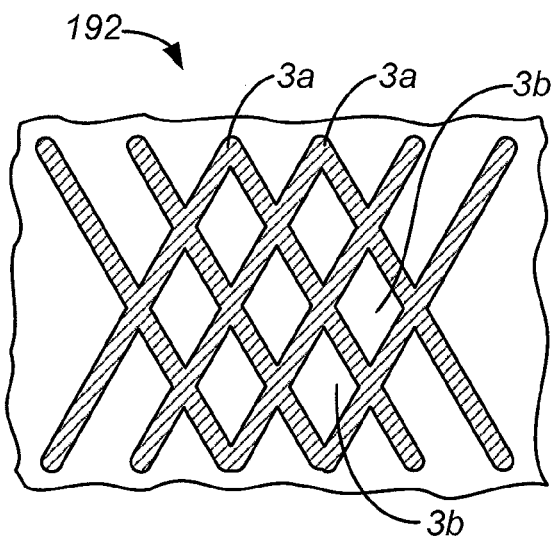
Figure 49A:
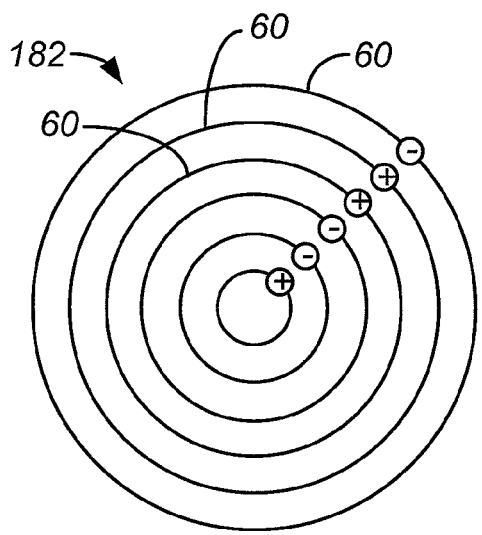
FIGS. 49A and 49B show an electrode array with a concentric-circle pattern for a fractional ablation and the ablation patterns on tissue that can be made from such a pattern.
Figure 50A:
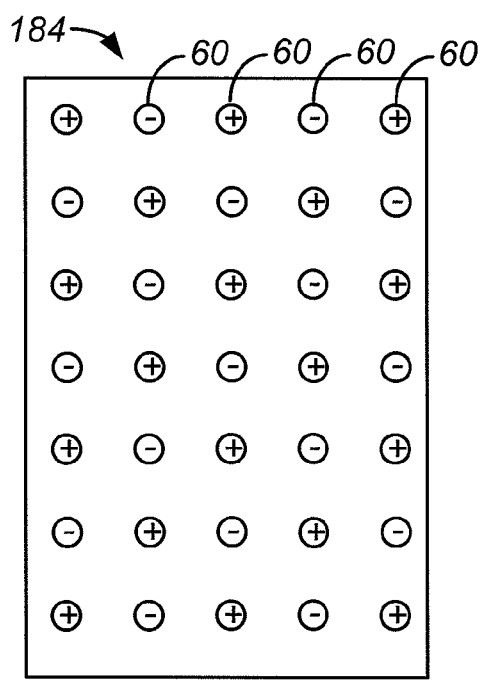
FIGS. 50A and 50B show an electrode array with a checkerboard pattern for a fractional ablation and the ablation patterns on tissue that can be made from such a pattern.

Embodiments of the invention include RF electrode array patterns that ablate a fraction of tissue within a given single ablational area, exemplary fractional arrays are shown in FIGS. 48A, 49A, and 50A. These fractional ablation electrode arrays may be applied, as above, to above to ablational structures that address a fully circumferential target area, or a structure that addresses any portion of a full circumference such as 90 degree radial surface, or a 180 degree radial surface. FIG. 48A shows a pattern 180 of linear electrodes 60 aligned in parallel as stripes on a support surface. The electrodes are spaced apart sufficiently such that when pressed against tissue in therapeutic contact, the burn left by distribution of energy through the electrodes results in a striped pattern 190 on the target tissue as seen in FIG. 48B corresponding to the electrode pattern, with there being stripes of burned or ablated tissue 3*a* that alternate with stripes of unburned, or substantially unaffected tissue 3*b*. In some embodiments of the method, particularly in ablation structures that address a target area of less than 360 radial degrees, such as a target surface that is about 180 degrees, or more particularly about 90 degrees of the inner circumference of a lumen, the ablation may be repeated with the ablational structure positioned at a different angle. FIG. 48C, for example, depicts a tissue burn pattern 191 created by a first ablational event followed by a second ablational event after the ablational structure is laterally rotated by about 90 degrees. FIG. 48D, for another example, depicts a tissue burn pattern 192 created by a first ablational event followed by a second ablational event after the ablational structure is laterally rotated by about 45 degrees.

The effect of an ability to ablate a tissue surface in this manner adds another level of fine control over tissue ablation, beyond such parameters as total energy distributed, and depth of tissue ablation. The level of control provided by fractional ablation, and especially when coupled with repeat ablational events as described above in FIGS. 48C and 48D, is to modulate the surface area-distributed fraction of tissue that is ablated to whatever degree the local maximal ablation level may be. The fractional ablation provided by such fractional electrode pattern may be particularly advantageous when the effects of ablation are not intended to be absolute or complete, but instead a functional compromise of tissue, or of cells within the tissue is desired. In some therapeutic examples, thus, a desirable result could be a partial reduction in overall function of a target area, rather than a total loss of overall function. Another example where such fractional ablation may be desirable is in the case where ablation is intended to be temporary or transient. In a fractional ablation of a target area in the wall of a gastrointestinal lumen, for example, a desirable result may be the transient compromise of tissue during which time the effect of such compromise may be evaluated.

In an ablation pattern that includes a burned area 3*a* and an unburned area 3*b*, it can be understood that cells from the unburned area could give rise to cells that would migrate or repopulate the denuded area within the burned area 3*b*.

Figure 49B:
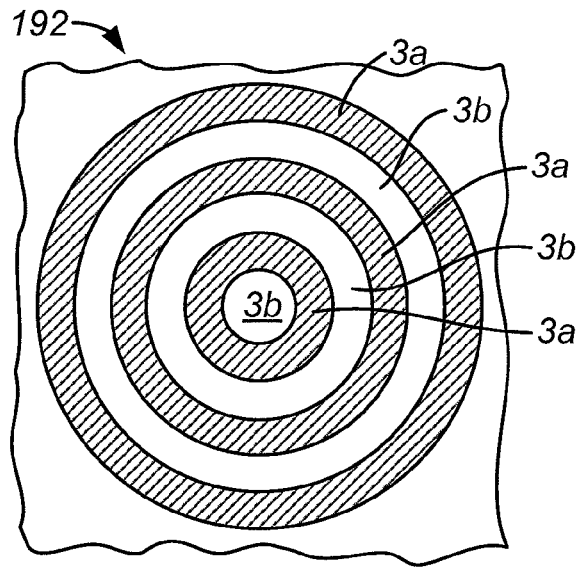
Figure 50B:
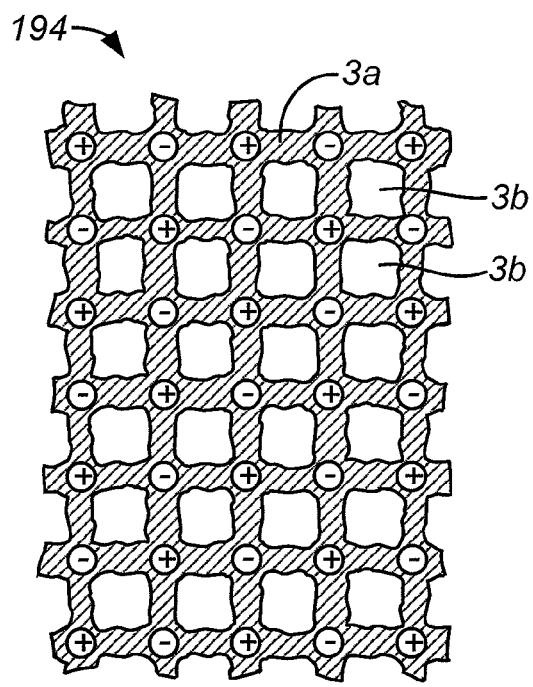

FIGS. 49A and 50A depict other examples of a fractionally-ablating electrode pattern on an ablation structure, and FIGS. 49B and 50B show the respective fractional burn patterns on tissue that have been treated with these electrode patterns. In FIG. 49A a pattern of concentric circles 182 is formed by wire electrodes that (from the center and moving outward) form a +−−++− pattern. When activated, the tissue between +− electrodes is burned, and the tissue between ++ electrode pairs or −− electrode pairs is not burned. Thus, the concentric pattern 192 of FIG. 49B is formed. Embodiments of fractionally-ablating electrode patterns such as those in FIG. 49A need not include perfect circles, and the circles (imperfect circles or ovals) need not be perfectly concentric around a common center.

Similarly, FIG. 50A shows a checkerboard pattern 184 of + and − electrodes which when activated create a burn pattern 194 as seen in FIG. 50B. Tissue that lies between adjacent + and − electrodes is burned, while tissue that lies between adjacent ++ electrodes or −− electrode pairs remains unburned. FIG. 50B includes a representation of the location of the + and − electrodes from the ablation structure in order to clarify the relative positions of areas that are burned 3*a* and the areas that remain substantially unburned 3*b*.

Embodiments of the invention include RF electrode array patterns that ablate a fraction of tissue within a given single ablational area by virtue of operational approaches, whereby some electrodes of a pattern are activated, and some are not, during an ablational event visited upon a target area. Exemplary fractional arrays are shown in FIGS. 51A, 52A, 53A and 54A. These fractional ablation electrode arrays may be applied, as above, to ablational structures that address a fully circumferential target area, or a structure that addresses any portion of a full circumference such as, by way of example, a 90 degree radial surface, or a 180 degree radial surface.

Figure 51A:
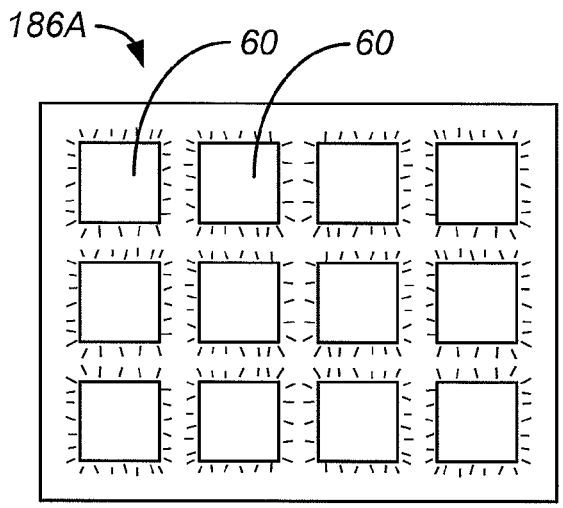
FIGS. 51A and 51B show an electrode array with a checkerboard pattern operating in a non-fractional manner and the ablation pattern on tissue that is made from such an operating pattern.
Figure 51B:
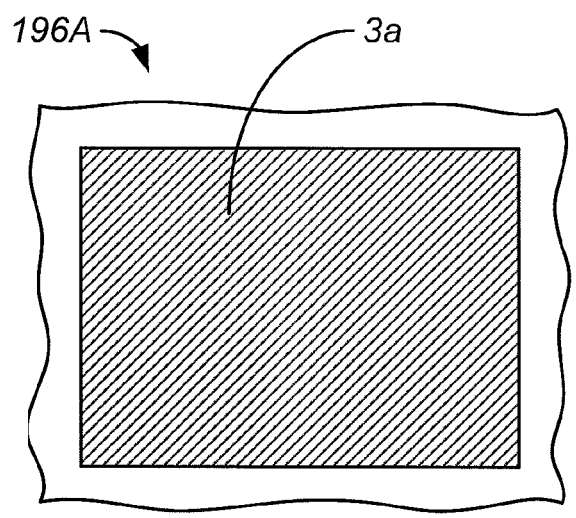
Figure 52A:
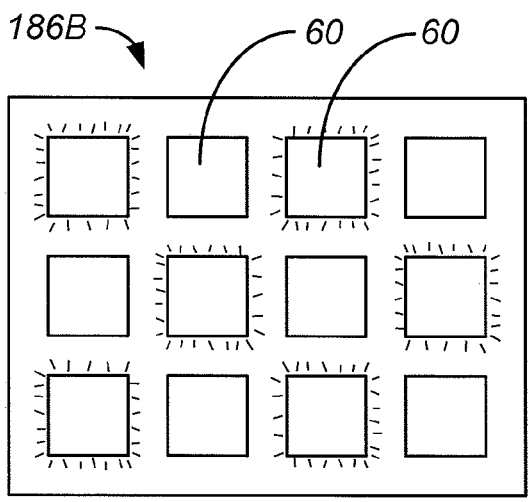
FIGS. 52A and 52B show an electrode array with a checkerboard pattern operating in a fractional manner and the ablation pattern on tissue that is made from such an operating pattern.
Figure 52B:
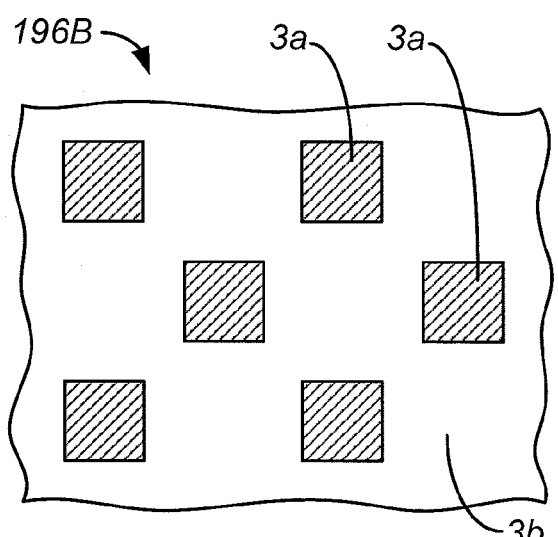

FIG. 51A shows a checkerboard electrode pattern during an ablational event during which all electrode squares of the operational pattern 186A are operating, as depicted by the sparkle lines surrounding each electrode. Operating the electrode pattern 186A in this manner produces an ablation pattern 196A, as seen in FIG. 51B, wherein the entire surface of tissue within the treatment area is ablated tissue 3*a*. FIG. 52A, on the other hand, shows a checkerboard electrode pattern during an ablational event during which only every-other electrode square of the operational pattern 186A is operating, as depicted by the sparkle lines surrounding each activated electrode. Operating the electrode pattern 186B in this manner produces an ablation pattern 196B, as seen in FIG. 52B, wherein a checkerboard fractionally ablated pattern with a dispersed pattern of ablated squares 3*a* of tissue 3*a* alternate with square areas of tissue 3*b* that are not ablated.

FIG. 53A shows a striped linear electrode pattern of alternating + and − electrodes during an ablational event during which all electrode squares of the operational pattern 188A are operating, as depicted by the sparkle lines surrounding each linear electrode. Operating the electrode pattern in this manner 188A produces an ablation pattern 198A, as seen in FIG. 53B, wherein the entire surface of tissue within the treatment area is ablated tissue 3*a*.

FIG. 54A, on the other hand, shows a striped linear electrode pattern 188B of alternating + and − electrodes during an ablational event during which alternate pairs of the linear electrode pairs are operating, as depicted by the sparkle lines surrounding the activated linear electrodes. Operating the electrode pattern in this manner 188B produces an ablation pattern 198A, as seen in FIG. 54B, wherein stripes of ablated tissue 3a within the treatment area alternate stripes of non-ablated tissue 3b.

Figure 55:
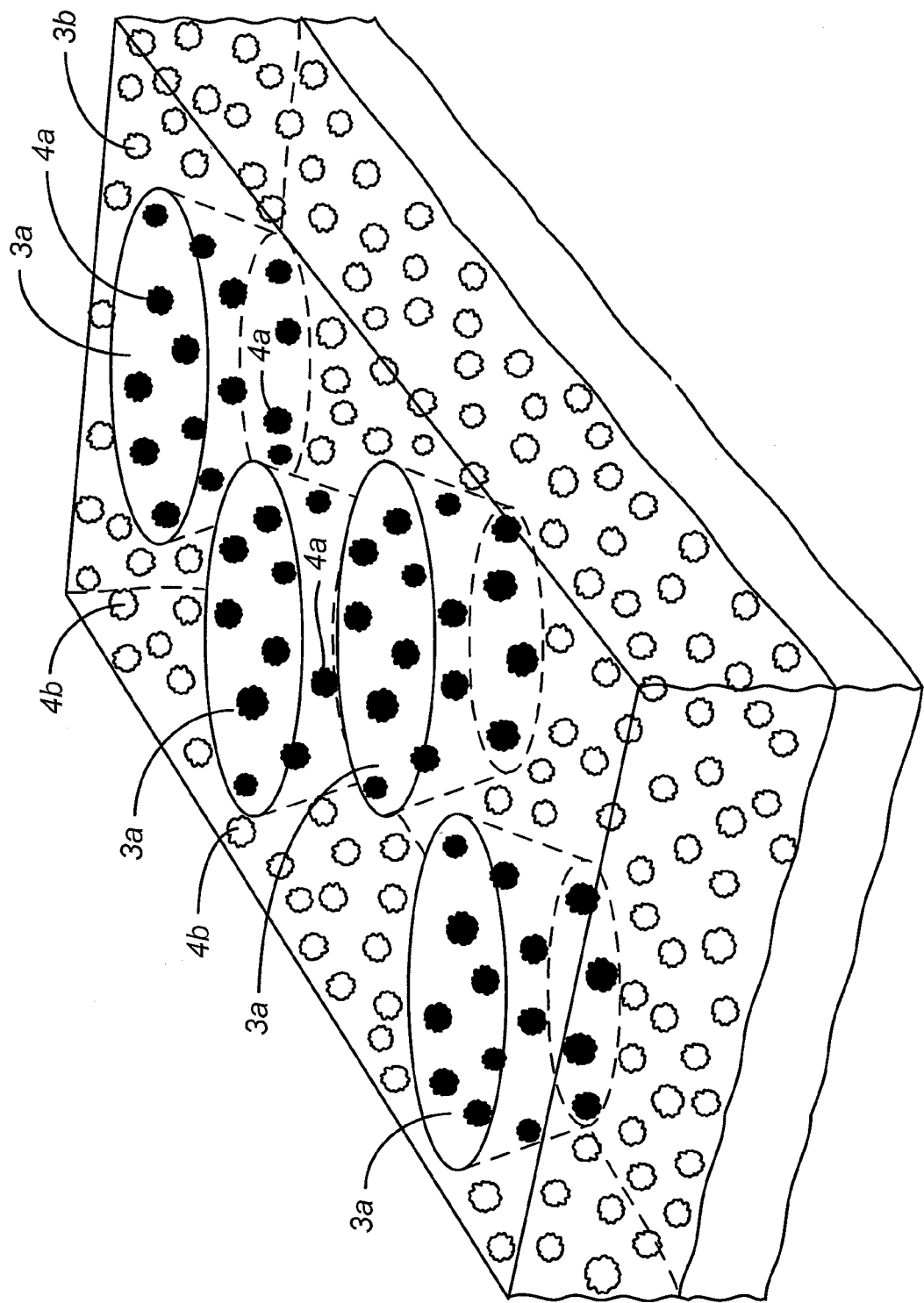
FIG. 55 shows a schematic rendering of a three dimensional view of a target region of a radial portion of a gastrointestinal wall after it has been ablationally treated.

FIG. 55 is a schematic rendering of a three dimensional view of a target region of a radial portion of a gastrointestinal wall after it has been ablationally treated, per embodiments of the invention. Ablated regions 3a are rendered as conical regions distributed through the target area within a larger sea of non-ablated tissue 3b. The conical regions 3a are of approximately the same depth, because of the control exerted over the depth of the ablation area, as described herein. The conical regions are of approximately the same width or diameter, and distributed evenly throughout the tissue, because of the control over ablational surface area, as described herein. In this particular example, the therapeutic target is actually a particular type of cell 4b (open irregular spheres), for example, a nerve cell, or endocrine secretory cell; and these cells are distributed throughout the target area. The post-ablation therapeutic target cells 4a (dark irregular spheres) are those which happened to be included within the conical regions 3a that were ablated. The post-ablation cells 4a may be rendered dysfunctional to varying degree, they may be completely dysfunctional, they may be, merely by way of illustrative example, on the average, 50% functional by some measure, and there functionality may vary over a particular range. It should be particularly appreciated however, per embodiments of the invention, that the cells 4b, those not included in the ablated tissue cones, are fully functional.

Controlling the Ablation in Terms of the Tissue Depth of the Ablation Effect In addition to controlling the surface area distribution of ablation, as may be accomplished by the use of fractional ablation electrodes as described above, or as controlled by the surface area of electrode dimensions, ablation can be controlled with regard to the depth of the ablation below the level of the tissue surface where the ablative structure makes therapeutic contact with the tissue. The energy delivery parameters appropriate for delivering ablation that is controlled with regard to depth in tissue may be determined experimentally. By way of example, an experimental set of exercises was performed on normal immature swine in order to understand the relationship between the electrical parameters of electrode activation and the resultant level of ablation in esophageal tissue. The data are shown in detail in U.S. application Ser. No. 10/370,645 of Ganz et al., filed on Feb. 19, 2003, and in the publication on Aug. 21, 2003, of that application, US 2003/0158550 A1, particularly in Tables 1-4 of that application. By an approach such as this, appropriate parameters for ablation of other tissues in the gastrointestinal tract may be determined. Such parameters as applied by ablational electrode patterns on an ablational structure with a 360 degree operating surface that is directed to esophageal tissue, by way of example, include 300 W delivered within 300 msec, with a tightly spaced with tightly spaced bi-polar electrode array (less than 250 microns). Ablation depth related to the energy density delivered with 8-12 J/cm2 results in complete removal of the epithelium. Such parameters as applied by electrode patterns on an ablation structure with an operating radial surface of about 90 degrees includes multiple narrow band electrodes spaced 250 microns wide, where the generator delivers very high power energy density at 40 W/cms to the tissue in an energy dosage of 12-15 J/cm2. In general, depth variances can be achieved via time of ablation, dosage, number of energy applications, and electrode spacing.

Figure 25:
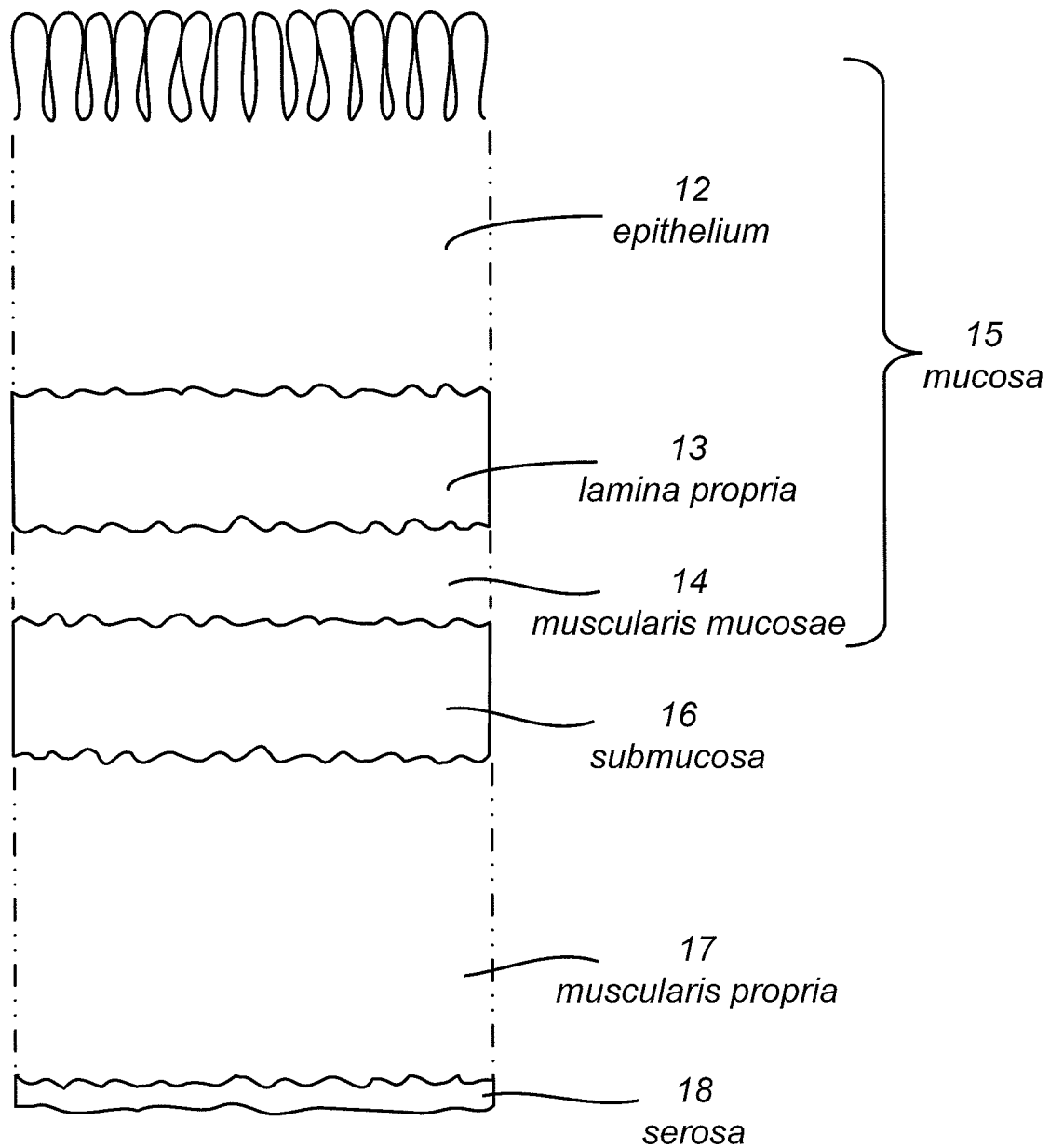
FIG. 25 is a schematic of view of a section through the wall of a representative organ of the gastrointestinal tract, including such organs as the stomach, pylorus, duodenum, and jejunum.

FIG. 25 provides a schematic representation of the histology of the gastrointestinal wall as it is found in various luminal organs such as the esophagus, stomach, pylorus, duodenum, and jejunum. The relative presence and depth and composition of the layers depicted in FIG. 25 vary from organ to organ, but the basic organization is similar. The layers of the gastrointestinal wall will be described in their order from the innermost to the outermost layer facing the gastrointestinal lumen; and as seen FIG. 25 and in terms of the direction from which an ablational structure would approach the tissue. The innermost layer can be referred to as the surface (epithelium), and succeeding layers can be understood as being below or beneath the "upper" layers. The innermost layer of a gastrointestinal tract organ, which is in direct contact with the nutrients and processed nutrients as they move through the gut is a layer of epithelium 12. This layer secretes mucous which protects the lumen from abrasion and against the corrosive effect of an acidic environment. Beneath the epithelium is a layer known as the lamina propria 13, and beneath that, a layer known as the muscularis mucosae 14. The epithelium 12, the lamina propria 13, and the muscularis mucosae 14 collectively constitute the mucosa 15.

Below the mucosal layer 15 is a layer known as the submucosa 16, which forms a discrete boundary between the muscosal layer 15 above, and the muscularis propria 17 below. The muscularis propria 17 includes various distinct layers of smooth muscle that enwrap the organ, in various orientations, including oblique, circular, and the longitudinal layers. Enwrapping the muscularis propria 17 is the serosa 18, which marks the outer boundary of the organ.

The entirety of the gastrointestinal tract wall is highly vascular and innervated. The mucosal layer is particular rich in glands and cells that secrete contents into the lumen and secrete hormones into the bloodstream. The nerves in this region are sensitive to the chemical composition of the nutrient flow, as it passes by, and their synaptic signals convey information to other organs that are involved in nutrient processing, such as the pancreas, and to the central nervous system, where information is integrated and regulates appetite and satiety. Nerve cells, proprioreceptors, in the muscularis propria sense the physical state of the wall, whether it is contracted or extended, and motor neurons in the musculature control the tension and general motility of the organ. All of these cells, including vasculature, exocrine cells, endocrine cell, and nerve cells are potential targets for ablation when ablational energy is directed toward the region in which they reside. As a result of receiving energy, cells may be killed or scarred to an extent that they are no longer functional, or they may be partially damaged, leaving some level of function. Additionally, it should be understood that these cells all exist in populations, and a partial ablation may manifest in a statistical distribution of damage, in which some cells of the population are eliminated or damaged beyond redemption, and some cells may remain substantially unaffected, and fully functional. In such partial or fractional ablation events, it can be understood that the remnant level of function following therapeutic ablation may include a range of function and dysfunction. It can also be appreciated that by such partial ablations, in some cases, damage may be transient. Recovery from transient damage may occur by any one or more of several broad mechanisms. For example, in some cases, individual cells may be damaged by the ablational energy, but in time they can recover their function. In other cases, cell populations can recover by regrowing or repopulating. For example, if a fraction of a population is eliminated, the local environment may encourage the division of surviving cells, or of resident stem cells to multiply, and have the population recover to its pre-ablational state. In still other instances, cells may migrate into damaged areas, and contribute to functional recovery by their presence. Further, as a result of ablation, a receptor or cell may be covered up by new tissue involved in the healing process rendering the receptor or cell either more or less sensitive and responsive. Still further, the tissue around the receptor or cell may heal after ablation in a manner that renders the receptor or cell either more or less sensitive and responsive.

As provided by embodiments of the invention, the ablation applied to gastrointestinal wall tissue may be depth-controlled, such that only the epithelium 12, or only a portion of the mucosal layer is ablated, leaving the deeper layers substantially unaffected. In other embodiments, the ablated tissue may commence at the epithelium yet extend deeper into the submucosa and possibly the muscularis propria, as necessary to achieve the desired therapeutic effect.

Device and Method for Partially-Circumferential Ablation

Figure 24:
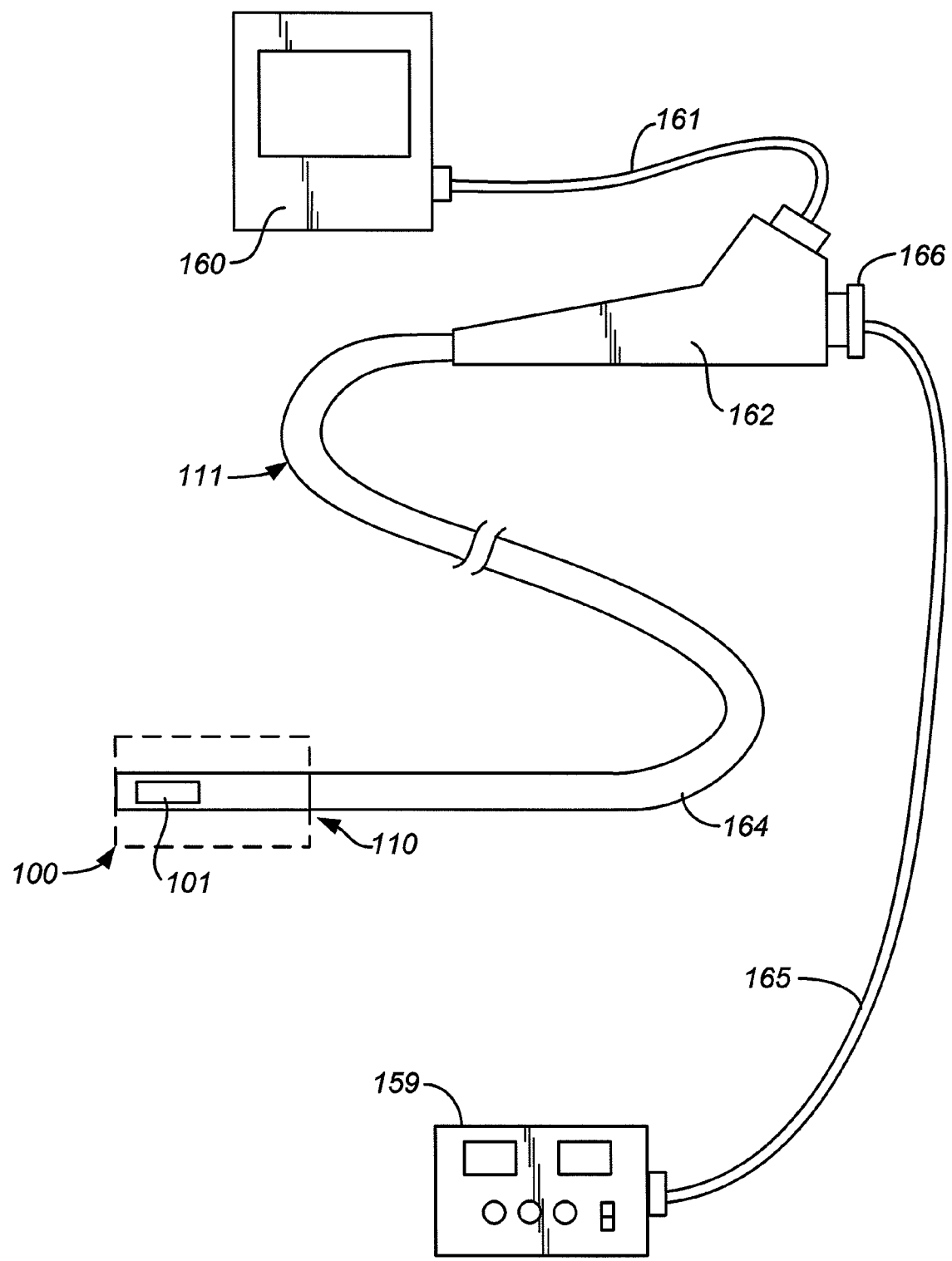
FIG. 24 is an illustration of the ablation device of the invention combined with an endoscope system.

One embodiment of a method of ablating tissue in the gastrointestinal tract includes the use of an ablation device with an ablation structure supported by conventional endoscopes 111, as illustrated in FIG. 24. As described herein, more particularly, the tissue targeted for ablation by embodiments of an ablation device and methods therefore is on the wall of the gastrointestinal tract in the lumen of an organ such as the stomach, pylorus, duodenum, or jejunum. An example of one commercially available conventional endoscope 111 is the Olympus "gastrovideoscope" model number GIF-Q160. While the specific construction of particular commercially available endoscopes may vary, as shown in FIG. 24, most endoscopes include a shaft 164 having a steerable distal end 110 and a hub or handle 162 which includes a visual channel 161 for connecting to a video screen 160 and a port 166 providing access to an inner working channel within the shaft 164. Dials, levers, or other mechanisms (not shown) will usually be provided on the handle 162 to allow an operator to selectively steer the distal end 110 of the endoscope 111 as is well known in the endoscopic arts. In accordance with the present invention, an ablation device, including an ablation structure is advanced into the gastrointestinal tract while supported at the distal end of an endoscope. The ablation structure is deflectable toward a tissue surface and the ablation structure is activated to ablate the tissue surface. Within the gastrointestinal tract, variously sized tissue surface sites can selectively be ablated using the device. As will be further described, the ablational structure of embodiments described in this section do not circumscribe a full 360 degrees, but rather circumscribe a fraction of 360 degrees, as will be described further below.

In general, in one aspect a method of ablating tissue in the gastrointestinal tract is provided. The method includes advancing an ablation structure into the gastrointestinal tract while supporting the ablation structure with an endoscope. In some embodiments, advancing the structure into the gastrointestinal may be sufficient to place the ablational structure of the device into close enough proximity in order to achieve therapeutic contact. In other embodiments, a subsequent step may be undertaken in order to achieve an appropriate level of therapeutic contact. This optional step will be generally be understood as moving the ablation structure toward the target site. The method thus may further include moving at least part of the ablation structure with respect to the endoscope and toward a tissue surface; and activating the ablation structure to ablate the tissue surface. Moving at least part of the ablation structure with respect to the endoscope can include, but is not limited to movement toward, away from or along the endoscope. Moving the ablational structure toward a target tissue surface may be performed by structures in ways particular to the structure. For example, the structure can be moved by inflating a balloon member, expanding a deflection member, or moving a deflection member. The function of such movement is to establish a therapeutically effective contact between the ablational structure and the target site. A therapeutically effective contact includes the contact being substantial and uniform such that the highly controlled electrical parameters of radiant emission from the electrode result in similarly highly controlled tissue ablation. Some embodiments of the invention further include structure and method for locking or securing such a therapeutically effective contact once established. Thus, some embodiments include a position locking step that, for example, uses suction to secure the connection between the ablation structure and the tissue site.

Figure 9:
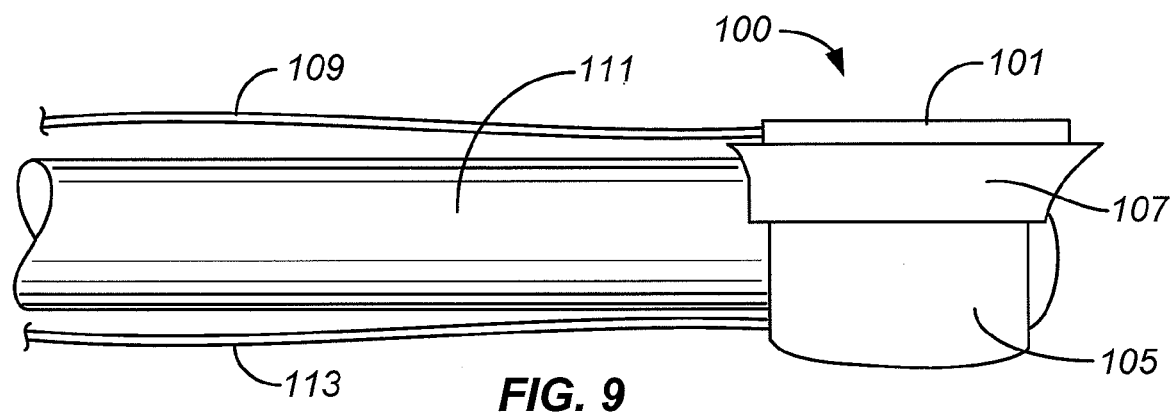
FIG. 9 is a view of the ablation device of the invention with a partially circumferential operating radius.
Figure 10:
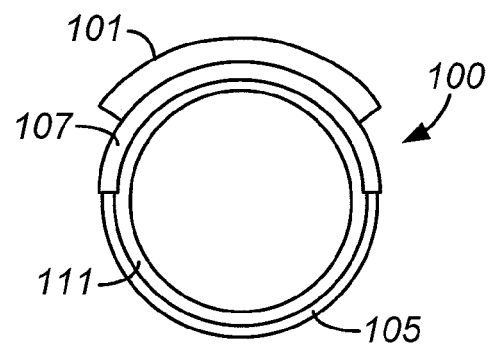
FIG. 10 is an end view of the ablation device of the invention.
Figure 11:
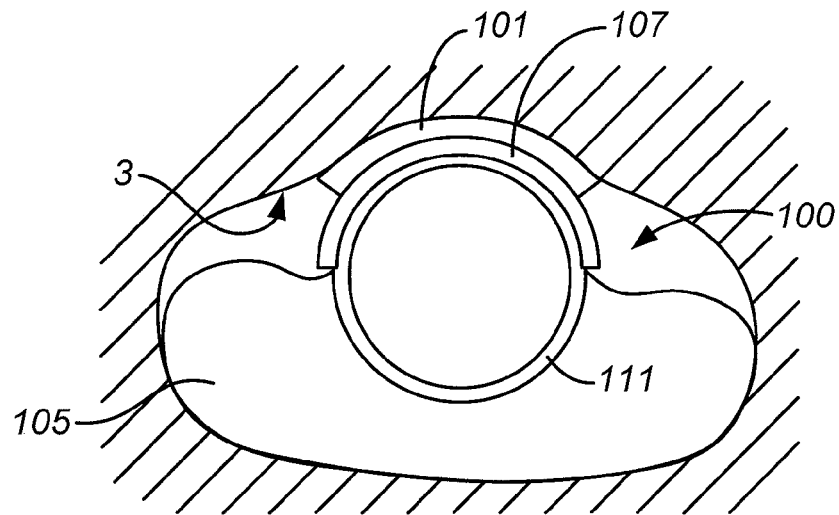
FIG. 11 is an end view of the device in an expanded configuration.

As shown in FIGS. 9, 10, 11, and 26, in one aspect a method of ablating tissue in the esophagus includes an ablation device 100 for ablating a tissue surface 3, wherein the device 100 includes an ablating structure, for example, an ablation structure 101 supported by an endoscope 111. The method includes ablating tissue in the wall of a luminal organ of the gastrointestinal tract by the steps of (1) advancing the ablation structure 101 into the luminal organ; (2) deflecting the ablation structure 101 toward a tissue surface 3; and (3) activating the ablation structure to ablate the tissue surface 3. As shown in FIG. 9, the device 100 can additionally include a housing 107, electrical connections 109, an inflation line 113 and an inflation member or balloon 105.

The ablation structure 101, in one embodiment is an electrode structure configured and arranged to deliver energy comprising radiofrequency energy to the mucosal layer of the wall of the organ of the gastrointestinal tract. It is envisioned that such an ablation structure 101 can include a plurality of electrodes. For example, two or more electrodes may be part of an ablation structure. The energy may be delivered at appropriate levels to accomplish ablation of mucosal or submucosal level tissue, or alternatively to cause therapeutic injury to these tissues, while substantially preserving muscularis tissue. The term "ablation" as used herein generally refers to thermal damage to the tissue causing any of loss of function that is characteristic of the tissue, or tissue necrosis. Thermal damage can be achieved through heating tissue or cooling tissue (i.e. freezing). In some embodiments ablation is designed to be a partial ablation. In other embodiments. Advantageously, in some embodiments, healing is more rapid and stricture formation in the tissues is minimized when such a completely ablational approach is used.

Although radiofrequency energy, as provided by embodiments of the invention, is one particular form of energy for ablation, other embodiments may utilize other energy forms including, for example, microwave energy, or photonic or radiant sources such as infrared or ultraviolet light, the latter possibly in combination with improved sensitizing agents. Photonic sources can include semiconductor emitters, lasers, and other such sources. Light energy may be either collimated or non-collimated. Other embodiments of this invention may utilize heatable fluids, or, alternatively, a cooling medium, including such non-limiting examples as liquid nitrogen, Freon™, non-CFC refrigerants, or $CO_2$ as an ablation energy medium. For ablations using hot or cold fluids or gases, the ablation system may include an apparatus to circulate the heating/cool medium from outside the patient to the heating/cooling balloon or other element and then back outside the patient again. Mechanisms for circulating media in cryosurgical probes are well known in the ablation arts. For example, and incorporated by reference herein, suitable circulating mechanisms are disclosed in U.S. Pat. No. 6,182,666 to Dobak; U.S. Pat. No. 6,193,644 to Dobak; U.S. Pat. No. 6,237,355 to Li; and U.S. Pat. No. 6,572,610 to Kovalcheck.

In a particular embodiment, the energy delivered to the wall of a luminal organ of the gastrointestinal tract comprises radiofrequency energy that can be delivered from the energy delivery device 100. Radiofrequency energy can be delivered in a number of ways. Typically, the radiofrequency energy will be delivered in a bipolar fashion from a bipolar array of electrodes positioned on the ablation structure 101, in some cases on an expandable structure, such as a balloon, frame, cage, or the like, which can expand and deploy the electrodes directly against or immediately adjacent to the mucosal tissue so as to establish a controlled level of therapeutic contact between the electrodes and the target tissue (e.g., through direct contact or through a dielectric membrane or other layer). Alternatively, the electrode structure may include a monopolar electrode structure energized by a radiofrequency power supply in combination with a return electrode typically positioned on the patient's skin, for example, on the small of the back. In any case, the radiofrequency energy is typically delivered at a high energy flux over a very short period of time in order to injure or ablate only the mucosal or submucosal levels of tissue without substantially heating or otherwise damaging the muscularis tissue. In embodiments where the ablation structure includes a plurality of electrodes, one or more of the electrodes can be bipolar or monopolar, and some embodiments include combinations of bipolar and monopolar electrodes.

The ablation structure 101 can be arranged and configured in any of a number ways with regard to shape and size. Typically, the array has an area in the range from about 0.5 $cm^2$ to about 9.0 $cm^2$. Typical shapes would include rectangular, circular or oval. In one embodiment, the ablation structure 101 has an area of about 2.5 $cm^2$. In another embodiment, the ablation structure 101 has an area of about 4 $cm^2$ and dimensions of about 2 cm. by 2 cm.

The housing 107 of the ablation device 100 is arranged and configured to support the ablation structure 101. The housing 107 can be made of any suitable material for withstanding the high energy flux produced by the ablation structure 101. As shown in FIGS. 9-14, 17, 18, 21, and 22, in one embodiment, the housing 107 is sandwiched between the ablation structure 101 and an endoscope 111 when the ablation device 100 is supported by an endoscope 111. One end of the ablation structure 101 can be further away from the endoscope than the other end to improve ease of contact with the targeted tissue (not shown). For example, to ensure the proximal end of the ablation structure 101 makes contact with the targeted tissue, the proximal end of the electrode may be supported by a tapered housing member 107.

The electrical connections 109 of the ablation device connect the ablation structure 101 to a power source. The electrical connections 109 can include a single wire or plurality of wires as needed to provide controlled energy delivery through the ablation structure 101. In one embodiment, the electrical connections 109 include low electrical loss wires such as litz wire.

The inflation line 113 is arranged and configured to transport an expansion medium, typically a suitable fluid or gas, to and from the inflation member. In one embodiment, the inflation line is a flexible tube. The inflation line 113 can be made of polymer or co-polymers, such as the non-limiting examples of polyimide, polyurethane, polyethylene terephthalate (PET), or polyamides (nylon). The inflation member 105 is designed to deflect the ablation device 100 in relation to a target tissue surface 3. The inflation member 105 can be reversibly expanded to an increased profile.

Figure 31:
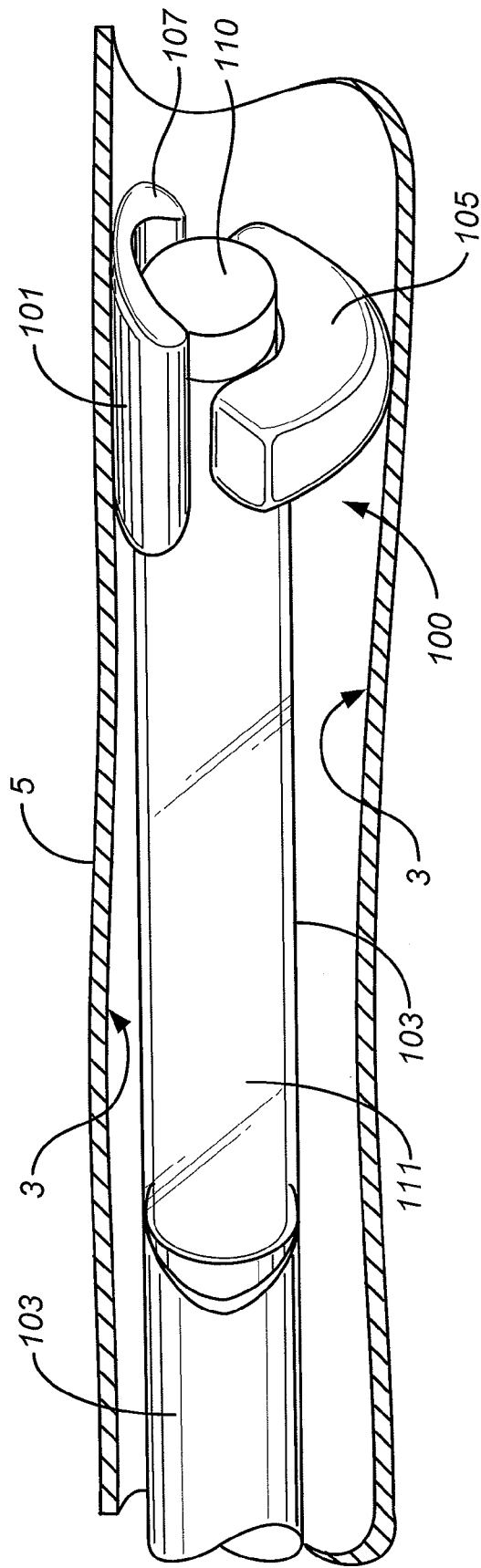
FIG. 31 is an illustration of the ablation device of FIG. 30 positioned within an esophagus.
Figure 42:
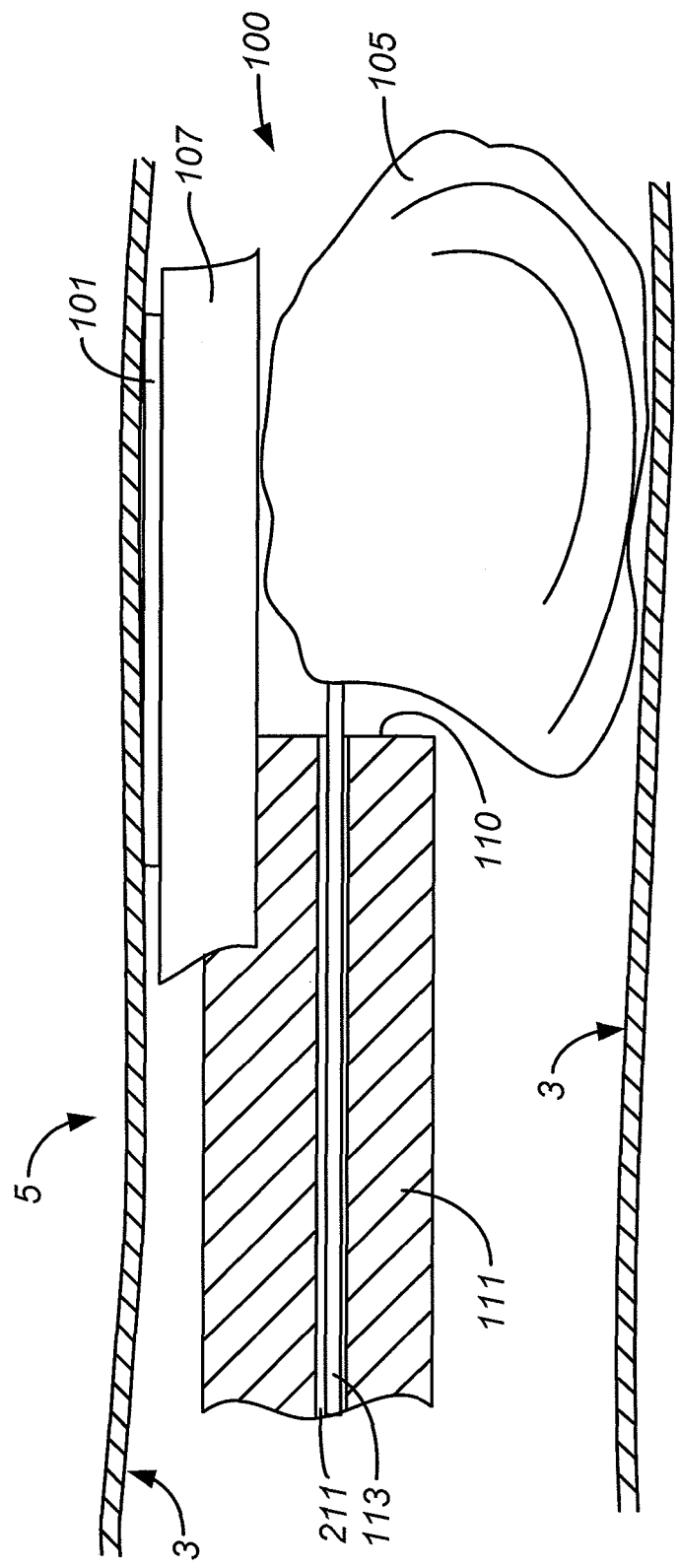
FIG. 42 is an illustration showing a cross sectional view of the ablation device of the invention positioned within the lumen of an organ of the gastrointestinal tract.
Figure 44:
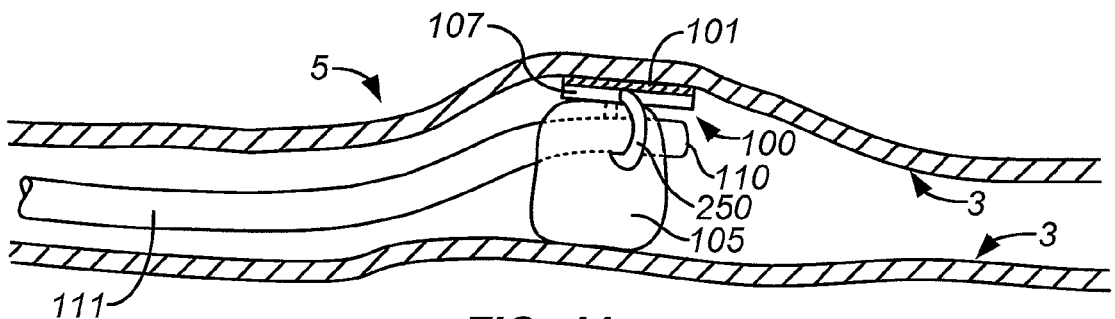
FIG. 44 is an illustration of the ablation device of the invention positioned within an esophagus showing a rotational feature combined with an inflation member in an expanded configuration.

In one embodiment, the inflation member 105 additionally serves as an attachment site for support of the ablation device 100 by an endoscope 111. As shown in FIGS. 9-14, 17, 18, 21 and 22, the inflation member 105 can be deployed from a low profile configuration or arrangement (see FIGS. 10, and 20) to an increased profile configuration or arrangement (see FIGS. 11-14, 17-19) using the expansion medium. In preparation for ablation, when the inflation member 105 is sufficiently inflated, deflection of the ablation device 100 in relation to a tissue surface 3 can be achieved. As shown in FIGS. 11, 31, 42, and 44, in one embodiment, deflection of the ablation device 100 results in a therapeutic level of contact, i.e., a substantially direct, uniform, and sustainable contact between the ablation structure 101 of the device 100 and the target tissue surface 3. For example, as shown in FIGS. 31, 42, and 44, when the inflation member 105 is sufficiently inflated, the resulting expanded profile of the inflation member 105, which contacts the tissue surface 3, results in contact by deflection between the tissue surface 3 of the inner wall of a luminal organ gastrointestinal tract 5 and the ablation structure 100. In these embodiments, suction can be applied in combination with the inflation member 105 to achieve contact between the ablation structure 101 and the tissue surface 3. Suction can be achieved through the endoscope 111 or through the ablation device 100 to aid in collapsing the targeted tissue surface 3 around the ablation structure 101.

In various embodiments, the inflation member 105 may be compliant, non-compliant or semi-compliant. The inflation member 105 can be made of a thin, flexible, bladder made of a material such as a polymer, as by way of non-limiting examples, polyimide, polyurethane, or polyethylene terephthalate (PET). In one embodiment, the inflation member is a balloon. Inflation of the inflation member 105 can be achieved through the inflation line 113 using, for example, controlled delivery of fluid or gas expansion medium. The expansion medium can include a compressible gaseous medium such as air. The expansion medium may alternatively comprise an incompressible fluid medium, such as water or a saline solution.

Figure 12:
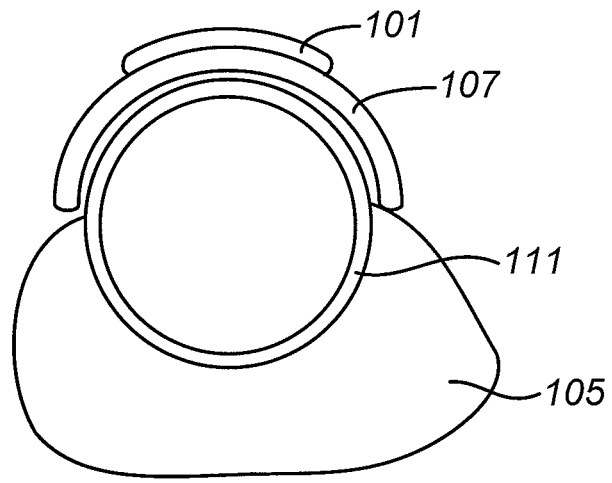
FIGS. 12, 13, and 14 are end views of the device in alternative expanded configurations.
Figure 13:
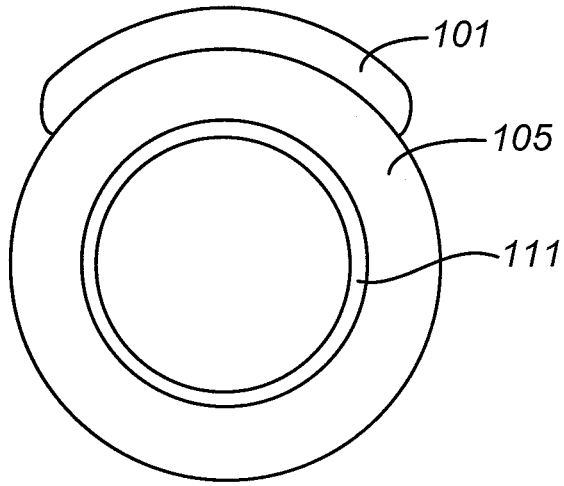
Figure 14:
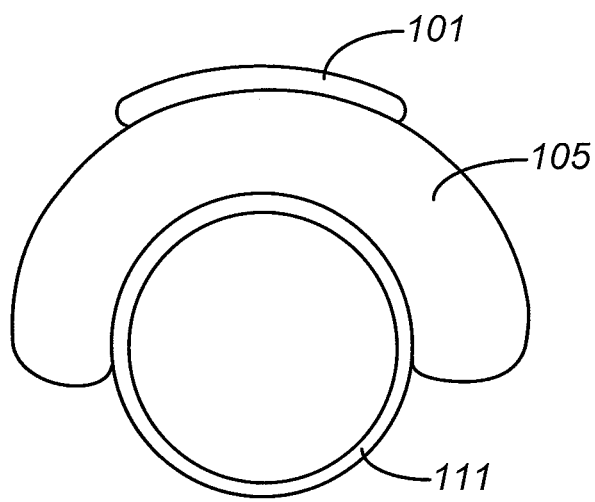

As shown in FIGS. 12, 13, and 14, the inflation member 105 can be configured and arranged in a variety of ways to facilitate deflection of the ablation device 100 in relation to a tissue surface 3. For example, as shown in FIG. 12, the inflation member 105 can be eccentrically positioned in relation to the supporting endoscope 111 as well as the housing 107 and the ablation structure 101. Alternatively, as shown in FIG. 13, the inflation member 105 can be positioned concentrically in relation to the supporting endoscope 111 and the ablation structure 101 can be attached to the inflation member 105 distally from the endoscope 111. In another embodiment, as shown in FIG. 12, the inflation member 105 can be positioned between the supporting endoscope 111 and the ablation structure 101. The ablation structure 101 shown in FIGS. 12-14 can cover a range of circumferential span of the endoscope 111 spanning, for example, from about 5 to 360 degrees when inflation member 105 is deployed.

One method of ablating tissue in a luminal organ of the gastrointestinal tract can include a first step of advancing an ablation structure 101, into the gastrointestinal tract. In a second step, the ablation structure 101 is supported with an endoscope 111 within the gastrointestinal tract. In a third step, the ablation structure 101 is deflected toward a tissue surface 3. In a fourth step, energy can be applied to the ablation structure 101 to ablate the tissue surface 3.

In another method, the step of advancing an endoscope-supported ablation structure 101 can include advancing the endoscope 111 into a luminal organ of the gastrointestinal tract and advancing the ablation structure 101 over the endoscope 111. For example, the endoscope 111 can be positioned relative to an ablation target tissue surface 3 after which the ablation structure 101 can be advanced over the outside of the endoscope 111 for ablating the target tissue surface 3.

In a further method, the step of supporting the ablation structure 101 with an endoscope 111 includes inserting the endoscope 111 into the ablation structure 101 (see for example, FIGS. 2A-2D). In a related method, the ablation structure 101 is supported by a sheath 103 (see FIGS. 26-28, 30, 31, 32 and 37) and the step of inserting the endoscope 111 into the ablation structure 101 includes inserting the endoscope 111 into the sheath 103. In a further related method, the step of inserting the endoscope 111 into the sheath 103 includes creating an opening in the sheath 103 (not shown).

In a particular method, a distal portion of a sheath 103 having a smaller outer diameter than a proximal portion of the sheath 103, is adapted to be expanded when an endoscope 111 is inserted into it.

In another method, the step of advancing the ablation structure 101 into the esophagus includes advancing the ablation structure 101 through a channel of the endoscope 111 from either the endoscopes proximal or distal end (as discussed below for FIGS. 34A, 35A and 36A). In yet another method, the step of supporting the ablation structure 101 comprises supporting the ablation structure 101 with a channel of the endoscope (see as discussed below for FIGS. 34A, 35A, 36A, 37-39). In a further method, a deflection structure or deflection member 150 is advanced through a channel of the endoscope 111 and the step of deflecting the ablation structure 101 toward a tissue surface 3 includes deflecting the ablation structure 101 with the deflection structure or deflection member 150 (see as discussed below for FIGS. 34A, 34B, 35A, 35B, 36A, 36B, 37-39).

As illustrated in FIGS. 34A, 35A, and 36A, variously adapted and configured ablation structures 101 can fit within and be conveyed through an endoscope internal working channel 211. In each case, the ablation structure 101 and accompanying deflection mechanism can be conveyed through the internal working channel 211 in a dimensionally compacted first configuration that is capable of expansion to a second radially expanded configuration upon exiting the distal end 110 of the endoscope 111 (For example, see FIGS. 34A, 34B, 35A, 35B, 36A, and 36B).

As shown in FIG. 34B, in one embodiment, the deflection mechanism is an inflation member 105, to which the ablation structure 101 can be integrated within or mounted/attached to, for example by etching, mounting or bonding. The inflation member 105 can be, for example, a compliant, non-compliant or semi-compliant balloon.

As shown in FIGS. 35B and 35B, in another embodiment, the deflection mechanism is an expandable member 209 that can expand to a second desired arrangement and configuration. As shown in FIG. 35B, the expandable member 209, can be an expandable stent, frame or cage device, to which an ablation structure 101 is mounted or integrated. For example, where the expandable member 209 is a wire cage, the wires can be a component of a bipolar circuit to provide the ablation structure 101 feature. Alternatively, the cage can have a flexible electrode circuit bonded or can be attached to an outer or inner surface of the cage to provide an ablation structure 101 that is an electrode. As shown in FIG. 36B, the expandable member 209, can be a folded or rolled series of hoops including or having an attached ablation structure 101 that expands upon exiting the endoscope distal end 110.

Figure 37:
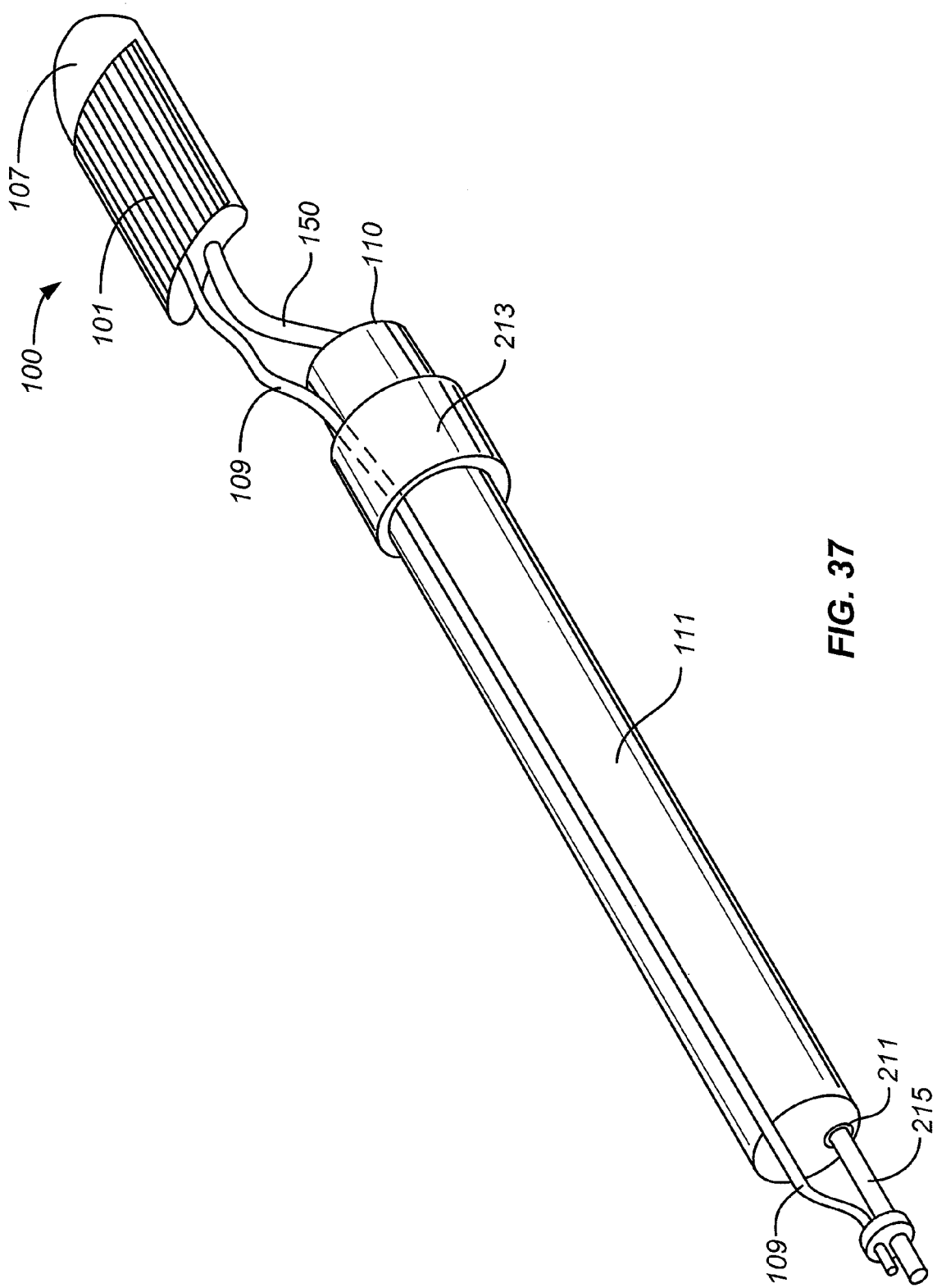
FIG. 37 is a view of the ablation device of the invention including an alternative deflection member.

As further illustrated in FIGS. 37-39, the ablation structure 101 can be supported with a channel of the endoscope 111. In one embodiment as shown in FIGS. 37-39, an ablation device 100 includes a deflection member 150 that supports an attached housing 107 and ablation structure 101. As shown in FIG. 39, the endoscope 111 includes an internal working channel 211 suitable for advancing or retreating the deflection member 150 which is connected to an internal coupling mechanism 215 of the ablation device 100. FIGS. 37 and 39 both show a deflection member 150 including a bent region of the deflection member 150 in a deployed position, wherein the deflection member 150 bent region is positioned external to the endoscope distal end 110. FIG. 38 shows the deflection member 150 in an undeployed position, wherein the deflection member 150 bent region is positioned internal to the endoscope 111. The ablation structure 101 is thus supported with a channel of the endoscope 111 (the internal working channel 211 of the endoscope 111) by way of the deflection member 150 and the connected internal coupling mechanism 215 of the ablation device 100.

In addition, when the deflection member 150 is advanced or moved proximally or distally within the endoscope internal working channel 211, the deflection member 150 is accordingly advanced through a channel of the endoscope 111. In another implementation, as shown in FIG. 42, wherein the deflection mechanism is an inflatable member 105 (shown in a deployed configuration) coupled to an inflation line 113, the inflation line 113 can be disposed within the endoscope internal working channel 211. In yet another implementation, both the inflatable member 105 (in an undeployed configuration) and inflation line 113 can be advanced within the internal working channel 211 either proximally or distally in relation to the endoscope 111. Conductive wires 109 can pass through the working channel (not shown) or outside as shown in FIG. 37.

Figure 41:
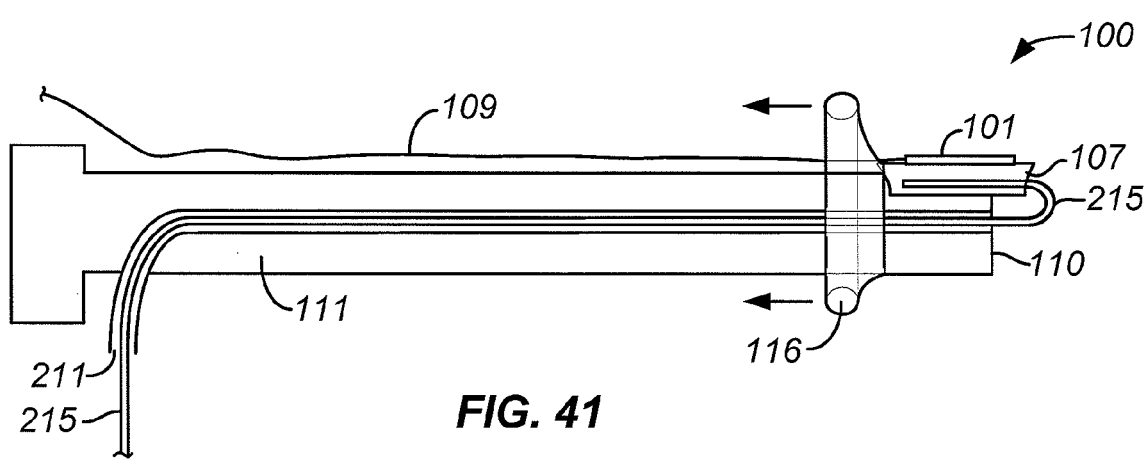
FIG. 41 is a cross sectional view of the ablation device of the invention showing an alternative internal coupling mechanism and a rolled sheath feature.

As shown in FIG. 41, in another implementation the endoscope 111 includes an internal working channel 211 suitable for supporting the ablation housing 107 and ablation structure 101 which are connected to an internal coupling mechanism 215 of the ablation device 100. As such, the connected ablation structure 101 is supported within a channel of the endoscope 111. Additionally as shown in FIG. 41, the housing 107 and ablation structure 101 can further be supported by an external region of the endoscope 111, wherein the internal coupling mechanism 215 is adapted and configured to position the housing 107 in contact with the external region of the endoscope 111. The internal coupling mechanism 215 can be cannulated (not shown) to facilitate use of the working channel to aspirate and flow in fluids or air.

In another ablation method, an additional step includes moving the ablation structure 101 with respect to the endoscope 111 within a luminal organ of the gastrointestinal tract. As illustrated in FIGS. 27, 28, 30, 32, and 47, and as discussed below, a sheath 103 of the ablation device 100 to which the ablation structure 101 is attached can enable moving the ablation structure 101 with respect to the endoscope 111. Further, as illustrated in FIGS. 34A, 35A, 36A, 37, 38, 39, and 41, and discussed above, an internal working channel 211 of the endoscope 111 through which at least a part of the ablation device 100 is disposed can enable moving the ablations structure 101 with respect to the endoscope 111.

Referring to FIGS. 11, 31, 42, and 44, in yet another method, the step of deflecting the ablation structure 101 toward a tissue surface 3 includes inflating an inflation member 105 of the ablation device 100 within a luminal organ of the gastrointestinal tract. The inflation member 105 can be arranged and configured to be reversibly inflatable. The inflation member 105 can be inserted along with the ablation structure 101 into an alimentary tract in a collapsed configuration and expanded upon localization at a pre-selected treatment area. In one implementation, the inflation member 105 is a balloon. For example, in FIGS. 11, 31, 42, and 44 it is shown how deflecting the ablation structure 101 toward a tissue surface 3 is achieved when the inflation member 105 is inflated or deployed. As illustrated in FIGS. 11, 31, 42, and 44, upon sufficient inflation, the inflation member 105 contacts a tissue surface 3 consequently deflecting the ablation structure 101 which contacts an opposing tissue surface 3.

Figure 19A:
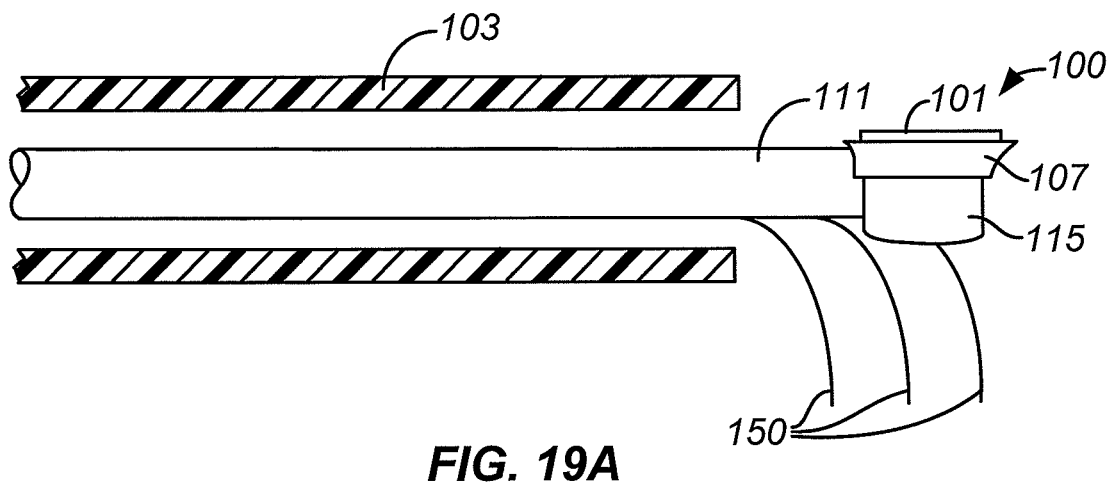
FIG. 19A is a view of the ablation device of the invention showing a deflection member feature.
Figure 19B:
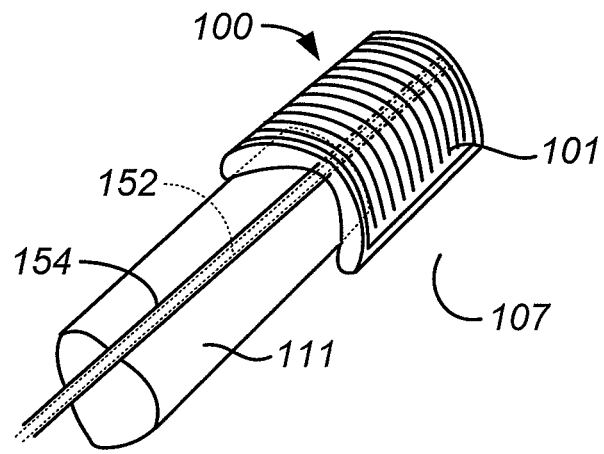
FIG. 19B is a view of the ablation device of the invention showing an alternative deflection member wherein the device is in an expanded configuration.

As shown in FIGS. 19B, 20, 35, 36 and discussed above, in a further method, the step of deflecting the ablation structure 101 includes expanding a deflection structure or deflection member 150. In one implementation, as shown in FIG. 19A the ablation device 100 includes a sheath 103, wherein the sheath 103 is arranged and configured to receive the deflection member 150, the endoscope 111 and ablation structure 101 internally to the sheath 103. In one implementation, the deflection member 150 is a shape memory alloy, for example, Nitinol. The flexible extensions of the deflection member 150 in this embodiment can be coupled to the endoscope, an elastomeric sheath 115 of the ablation device 100 (shown in FIG. 19A) or any part of the device 100, including the ablation housing 107.

As shown in FIGS. 34, 35, 36, 37, 38, and 39, and discussed above, in a further method, the step of deflecting the ablation structure 101 includes moving a deflection structure or deflection member 150.

Figure 23:
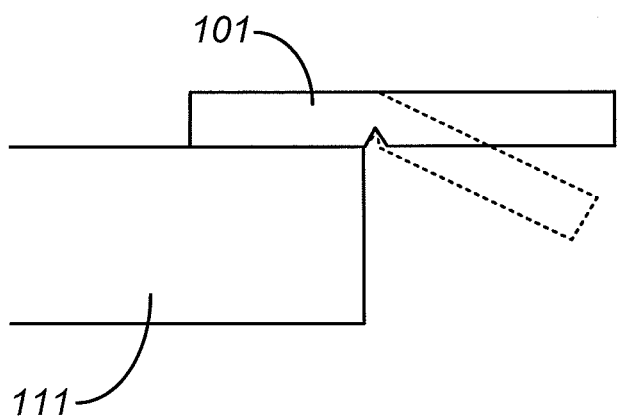
FIG. 23 is a view of the ablation device of the invention showing an ablation structure feature.

Briefly, in each case moving the deflection 150 is used to change the deflection member 150 from a non-deployed to a deployed configuration. As shown in FIG. 23, in one embodiment, deflecting the ablation structure 101 includes a flexing point in the ablation structure 101, wherein the ablation structure 101 can deflect in response to, for example, resistance met in contacting a tissue surface 3.

As shown in FIGS. 43, 44, and 45A-45C and as discussed in further detail below, in another method, the step of deflecting the ablation structure 101 includes rotating, pivoting, turning or spinning the ablation structure 101 with respect to the endoscope 111 along their respective and parallel longitudinal axes. Deflection of the ablation structure 101 with respect to the endoscope 111 can occur in combination with the endoscope 111 distal end 110 deflecting with respect to a target site on the wall of an luminal organ of the gastrointestinal tract or without. Also, the ablation structure 101 can deflect in combination with an inflation member 105 used to achieve apposition of the ablation device 100 to the tissue. In some embodiments, the step of deflecting the ablation structure 101 may additionally include any combination of the above disclosed deflecting steps.

Figure 46A:
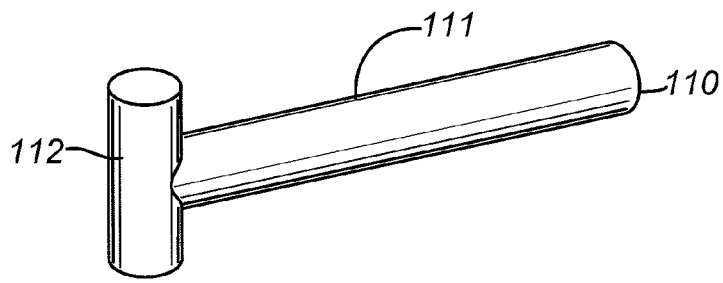
FIG. 46A is a view of an endoscope.
Figure 46B:
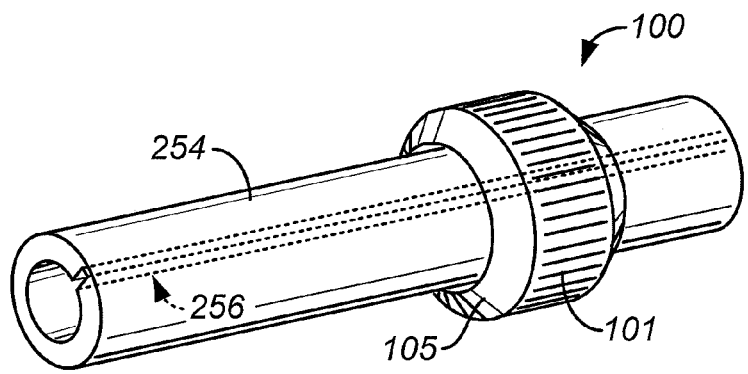
FIG. 46B is a view of the ablation device of the invention including a catheter feature.
Figure 47:
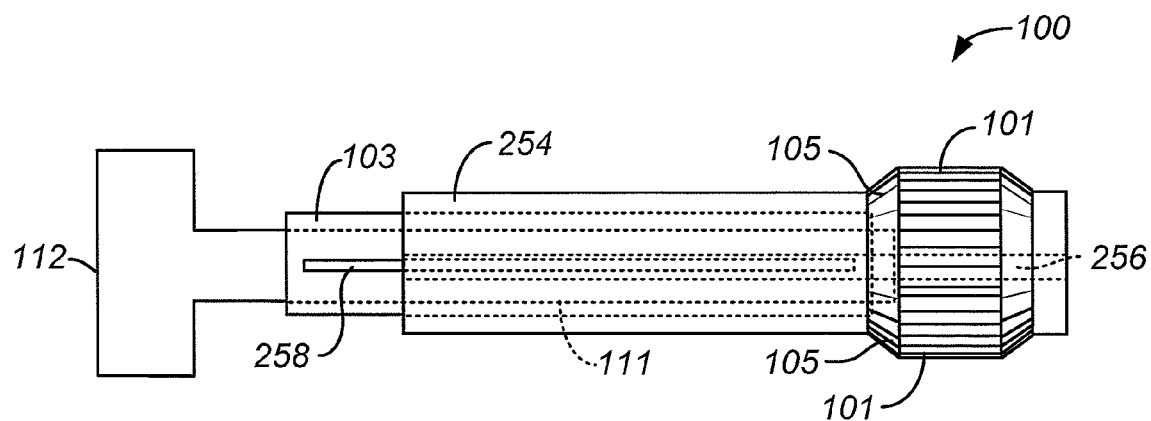
FIG. 47 is a view of the ablation device of the invention including the features shown in FIGS. 46A-46C in an assembly.

As shown in FIGS. 19, 20, 21, 22, 34A, 34B, 35A, 35B, 36A, 36B, 46B, and 47, in another ablation method, an additional step includes moving the ablation structure 101 from a first configuration to a second radially expanded configuration. The details regarding radial expansion of the ablation structure 101 shown in FIGS. 19, 20, 21, and 22 are described below, while the details for FIGS. 34A, 34B, 35A, 35B, 36A, and 36B are described above. Additionally, as shown in FIGS. 46B and 47 the ablation structure 101 can be arranged in a first configuration wherein the ablation structure 101 is coupled directly or alternatively through an housing 107 (not shown) to an inflation member 105B attached to a catheter 254. In an undeployed configuration as shown in FIGS. 46B and 47, the non-inflated inflation member 105 and ablation structure 101 have a relatively low profile in relation to the endoscope 111. When deployed, the inflation member 105 moves the ablation structure 101 to a second radially expanded configuration (not shown).

Figure 15:
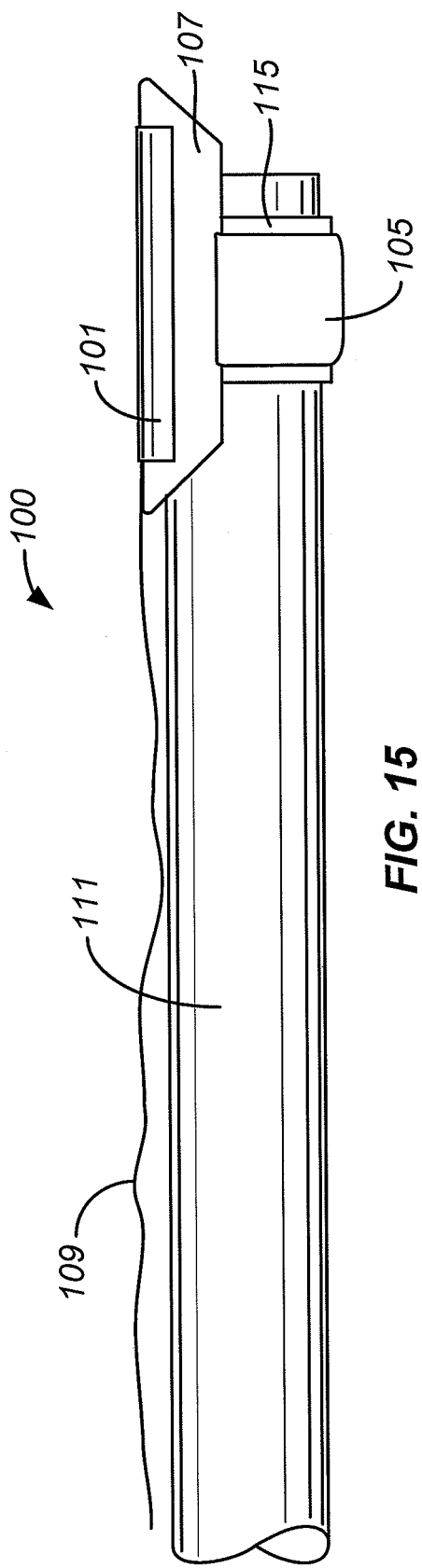
FIG. 15 is a view of the ablation device of the invention in an unexpanded configuration.
Figure 16:
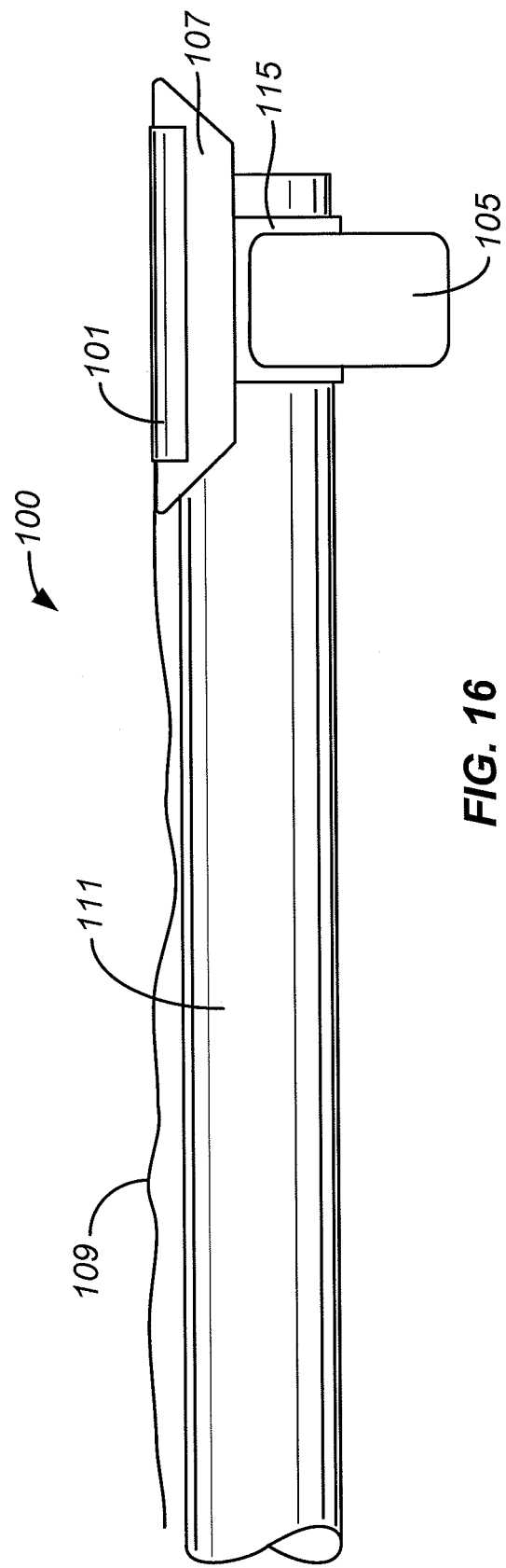
FIG. 16 is a view of the ablation device of the invention in an expanded configuration.
Figure 17:
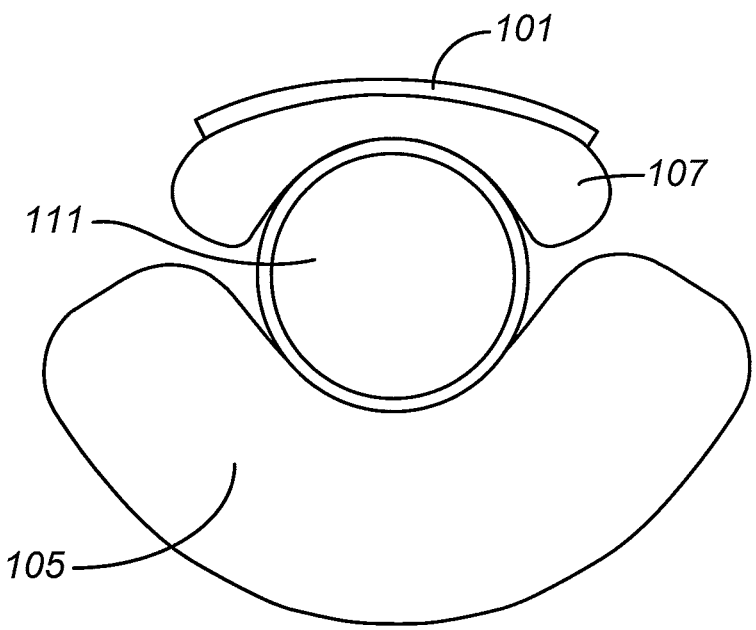
FIGS. 17 and 18 are end views of the device in an expanded configuration.
Figure 18:
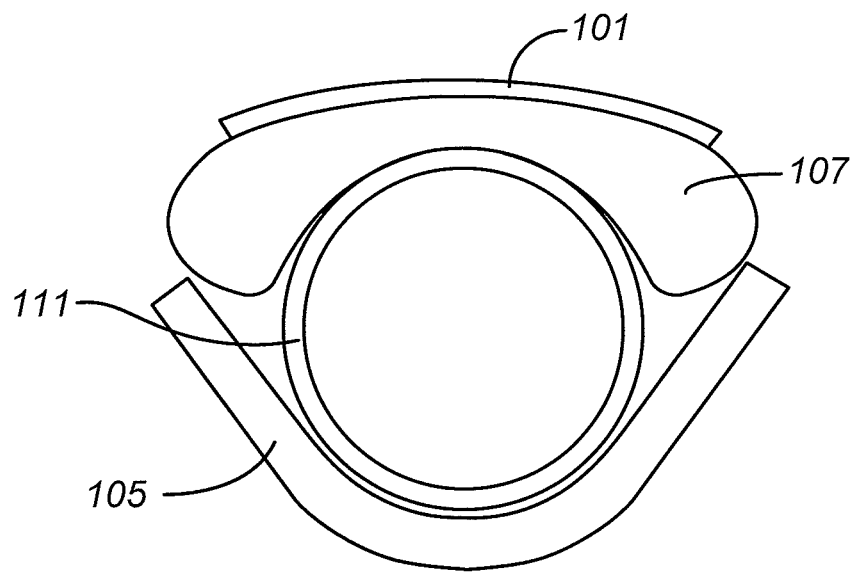

As shown in FIGS. 15, 16, 40, 43, 44, 45A-45C, 46B, and 47, in a further method, an additional step includes attaching the ablation structure 101 to the endoscope 111. As shown in FIGS. 15 and 16, attachment of the ablation structure 101 to the endoscope 111 can also be by way of an elastomeric sheath 115 The elastomeric sheath 115 can removably hold the ablation structure 101 in a desired position on the endoscope 111. The elastomeric sheath 115 can be arranged and configured to fit over the endoscope distal end 110. As shown in FIGS. 15 and 16, the inflation member 105B can be attached to the elastomeric sheath 115 or alternatively the inflation member 105B can also act as the "elastomeric sheath" (not shown).

In another method, the step of attaching the ablation structure 101 to the endoscope 111 includes attaching the ablation structure 101 to an outside surface of the endoscope. Alternatively, the attaching step can include, for example, attaching to an inside surface, an outside or inside feature of the endoscope, or any combinations of the above. Lubricants such as water, IPA, jelly, or oil may be use to aid attachment and removal of the ablation device from the endoscope.

As shown in FIG. 41, in a further method, the step of attaching the ablation structure 101 to the endoscope 111, includes an ablation structure 101 having an attached rolled sheath 116, wherein attaching the ablation structure 101 to the endoscope 111 includes unrolling the sheath 116 over an outside surface of the endoscope 111. The rolled sheath 116 can additionally cover the electrical connections 109 of the ablation device 100 along a length of the endoscope 111 (see FIG. 41). In a related method, the ablation structure 101 is attached to the endoscope 111 by an attaching step including unrolling the rolled sheath 116 over an outside surface of the endoscope 111 and part of the ablation structure 101.

Figure 40:
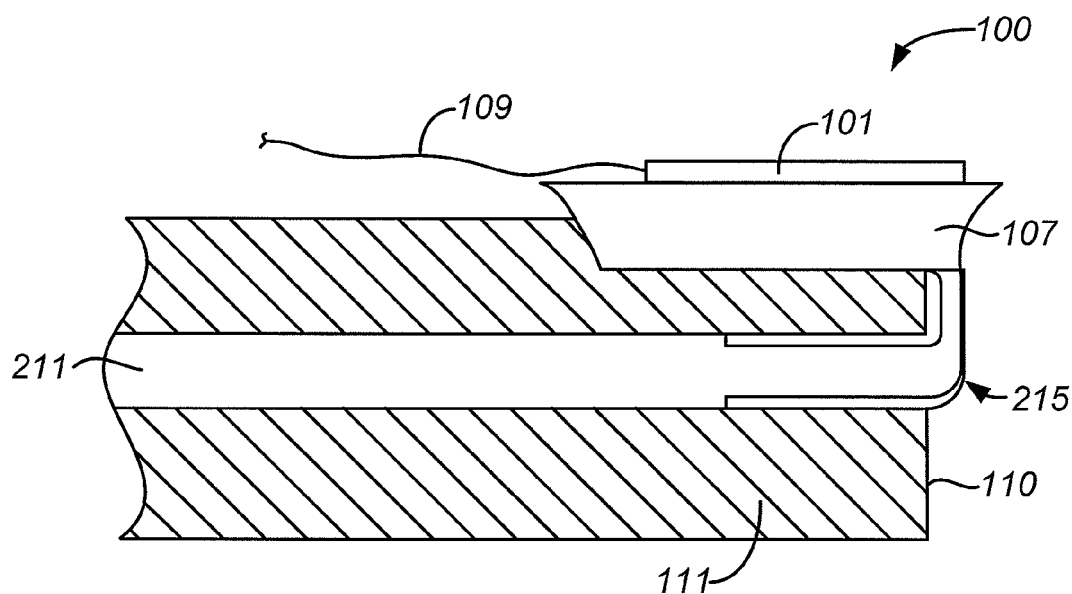
FIG. 40 is a cross sectional view of the ablation device of the invention showing an internal coupling mechanism feature.

In another method, as shown in FIG. 40, the step of attaching the ablation structure 101 to the endoscope 111 includes attaching the ablation structure 101 to a channel of the endoscope. As shown in FIG. 40, in one implementation, the housing 107 and ablation structure 101 are coupled to an internal coupling mechanism 215 that can be positioned within an internal working channel 211 of the endoscope 111. The internal coupling mechanism 215 in FIG. 40 is shown as attached to the internal working channel 211 at the endoscope distal end 110. In this embodiment, the housing 107 and ablation structure 101 are shown in alignment with and coupled to an outside surface of the endoscope 111 near the distal end 110.

In one method of ablating tissue in the alimentary tract, the tissue surface 3 can include a first treatment area and activation of the ablation structure 101 step can include activation of the ablation structure 101 to ablate the first treatment area, and further include moving the ablation structure 101 to a second area without removing the ablation structure 101 from the patient and activating the ablation structure 101 to ablate the second tissue area 3. Moving, in this sense, refers to moving the ablational structure to the locale of a target site, and thereafter, further moving of the structure into a therapeutically effected position can be performed variously by inflating a balloon member, or deflection or inflating a deflection member, as described in detail elsewhere. For example, where two or more areas of the tissue surface 3 of a target area in the wall of an organ in the gastrointestinal tract can be ablated by directing the ablation structure 101 to the first target region and then activating the ablation structure 101 to ablate the tissue surface 3. Then, without removing the ablation structure 101 from the patient, the ablation structure 101 can be directed to the second target area in the wall of an organ for ablation of the appropriate region of the tissue surface 3.

In general, in another aspect, an ablation device 100 is provided that includes an ablation structure 101 removably coupled to an endoscope distal end 110, and a deflection mechanism adapted and configured to move the ablation structure 101 toward a tissue surface 3 (see for example, FIGS. 5-19, 22, 22, 27-29, 30-32, 34A, 35A, 36A, 37, 38, 39, 42, 44, and 47).

In a related embodiment, the ablation device 100 additionally includes an ablation structure movement mechanism adapted to move the ablation structure 101 with respect to the endoscope 111. As discussed below and shown in FIGS. 26-28, and 30-32, the ablation structure movement mechanism can be a sheath 103 to which the ablation structure 101 is attached, wherein the sheath 103 is arranged and configured to move the ablation structure 101 with respect to an endoscope 111 received within the sheath 103. Alternatively, as discussed above and shown in FIGS. 34A, 35A, 36A, and 37-39, the ablation structure movement mechanism can be in the form of an internal coupling mechanism 215 of the ablation structure 100, wherein the ablation structure is connected to the internal coupling mechanism 215 and at least a portion of the internal coupling mechanism 215 is disposed internally to the endoscope.

In another embodiment, the ablation device 100 additionally includes a coupling mechanism designed to fit over an outside surface of an endoscope 111, to couple the ablation structure 101 with the endoscope 111. As discussed above, a spiral sheath 104, an elastomeric sheath 115, a rolled sheath 116 and an internal coupling mechanism as shown in FIGS. 15, 16, 40, and 41 respectively, are examples of such coupling mechanisms. In a particular embodiment, the coupling mechanism includes a sheath 103 capable of supporting the ablation structure 101. The sheath 103 can be tubing, a catheter or other suitable elongate members. The sheath 103 can be arranged and configured so that it can be moved independently of an associated endoscope.

As shown in FIG. 41, in another embodiment, the sheath 103 can be arranged and configured as a rolled sheath 116 that can be unrolled over the outside surface of the endoscope. In use, a rolled sheath 116 connected to the ablation device 100, for example at substantially near the proximal end of the housing 107 (from the perspective of an operator of the device), can be unrolled from such a position and continue to be unrolled toward the proximal end 112 of the endoscope 111 (see FIG. 47). In this way, the rolled sheath 116 can be caused to contact and cover all or a portion of the length of the endoscope 111 (not shown). Additionally, as the rolled sheath 116 is unrolled along the endoscope 111, it can sandwich the electrical connections 109 between the rolled sheath 116 and the endoscope 111 (see generally FIG. 41).

Figure 30:
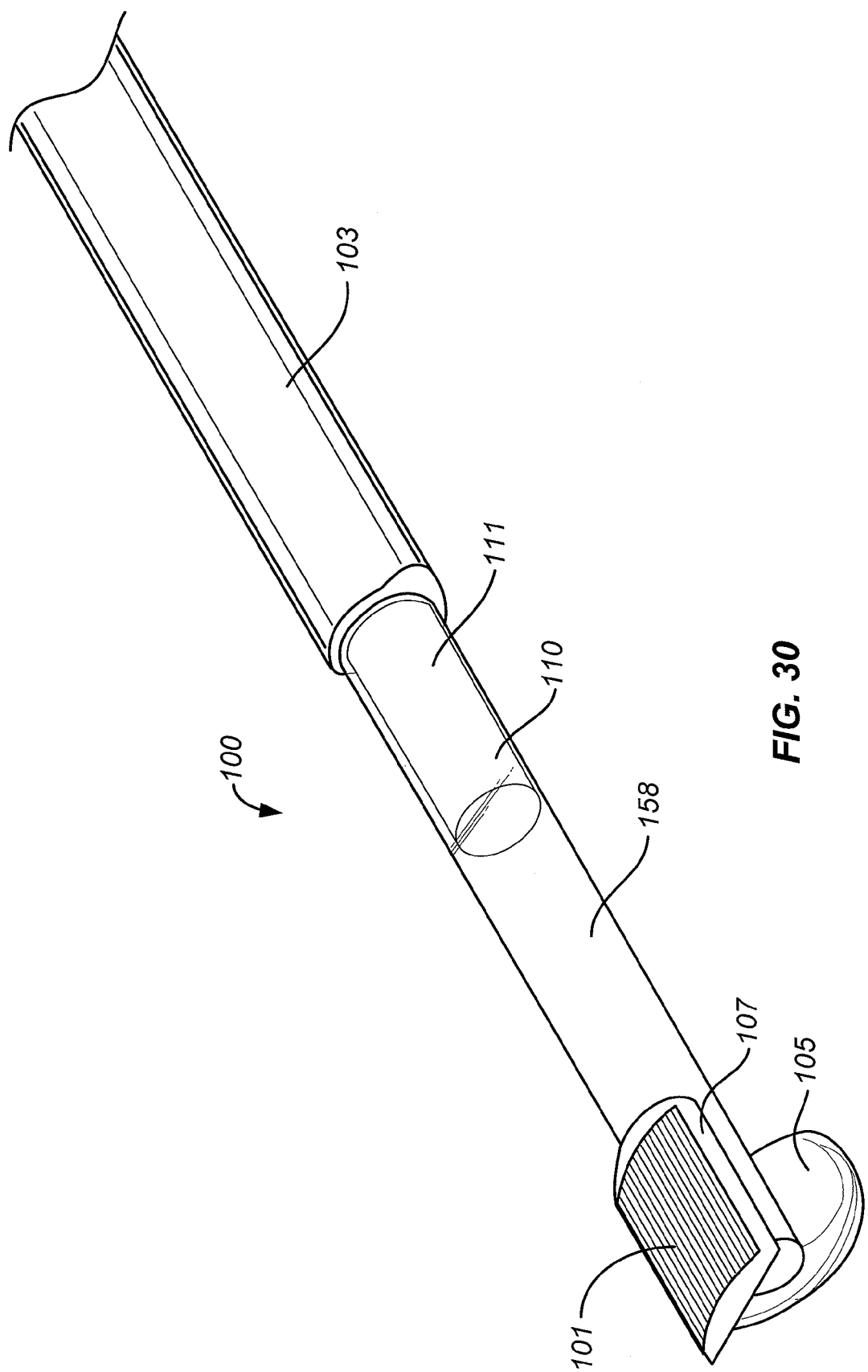
FIG. 30 is a view of the device including an alternative optically transmissive sheath feature and an inflation member feature in an expanded configuration.

In another embodiment, as shown in FIGS. 30 and 31, the sheath 103 can be arranged and configured to support a deflection mechanism wherein the deflection mechanism includes a deflection structure or deflection member 150. As illustrated in FIGS. 30 and 31, where the deflection member 150 is an inflation member 105, the inflation member 105 can be directly attached to the sheath 103. As shown in each case, the inflation member 105 is positioned opposite the placement of the ablation structure 101, which is also attached to the sheath 103. This configuration of the sheath 103 provides support for the inflation member 105 and the ablation structure 101 irrespective of the positioning of the endoscope distal end 110. For example, as shown in FIG. 30, the endoscope distal end 110 can be positioned to provide a gap between the distal end 110 and a distal end of the sheath 103 where the ablation structure 101 and inflation member 105 are positioned. In contrast, as shown in FIG. 31 the endoscope distal end 110 can extend through and beyond the distal end of the sheath 103.

Figure 26:
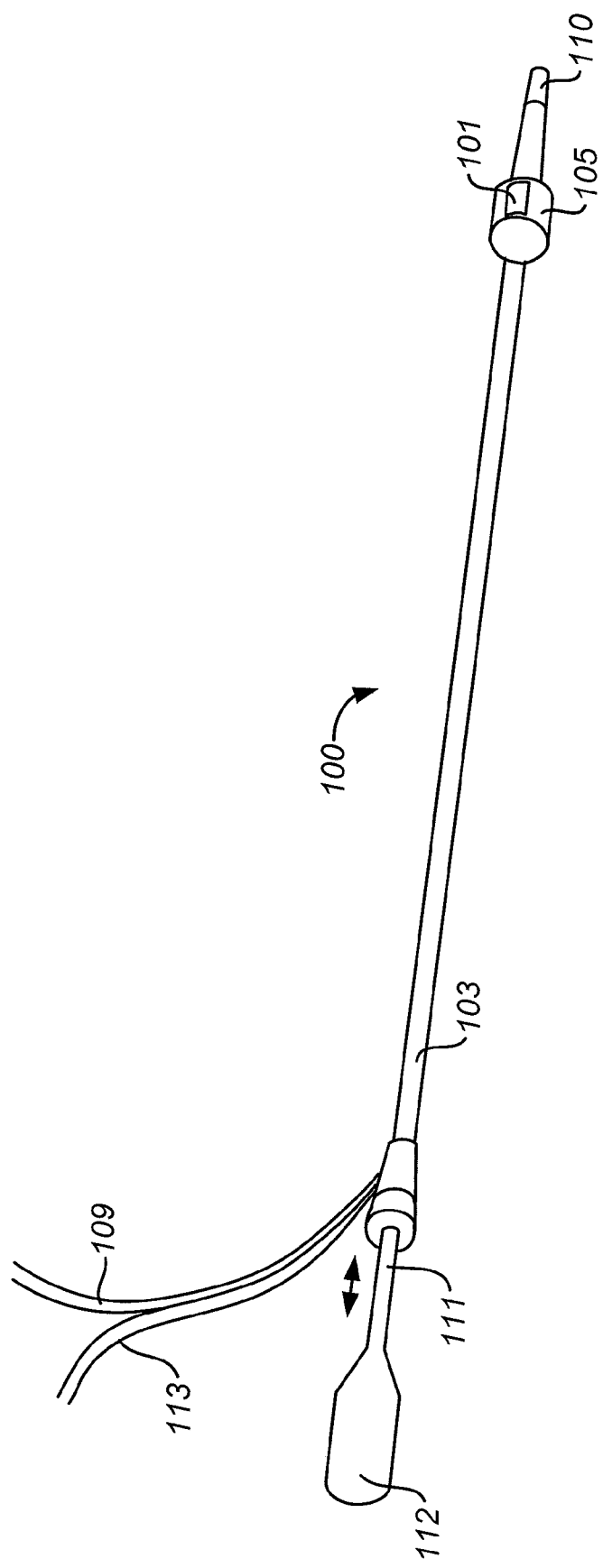
FIG. 26 is a view of the ablation device of the invention including an elongated sheath feature.

In another embodiment, as shown in FIG. 26, the sheath 103 can be elongated. FIG. 26 illustrates a sheath including electrical connections 109 and an inflation line 113. The sheath 103 may include pneumatic and/or over extruded wires impregnated within the sheath 103. In use, the sheath 103 can be introduced first into an alimentary tract, wherein the sheath 103 serves as a catheter like guide for introduction of the endoscope 111 within the sheath 103. Alternatively, the endoscope 111 may be introduced first and thereby serve as a guidewire for the sheath 103 to be introduced over. FIG. 26 also shows attachment of an inflation member 105 to the sheath 103, in an arrangement wherein the ablation structure 101 is attached to the inflation member 105 opposite the sheath 103 attachment point.

In yet another embodiment (not shown) the sheath 103 includes an optically transmissive portion 158 adapted and configured to cooperate with a visual channel 161 of an endoscope 111. For example, the sheath 103 may be made of clear, translucent or transparent polymeric tubing including PVC, acrylic, and Pebax® (a polyether block amide). As shown in FIG. 24, one component of an endoscope 111 can be a visual channel 161 that provides visual imaging of a tissue surface 3 as imaged from the endoscope distal end 110. For example, the transmissive portion 158 can allow visualization of the wall of an esophagus 3 through the transmissive portion 158 of the sheath 103. As shown in FIG. 28 and in the cross-section view provided in FIG. 29, the sheaths 103 shown in FIGS. 27 and 28, include an optically transmissive portion 158 arranged and configured to provide viewing of tissue surfaces 3 through the wall of the sheath 103, with the aid of an internally disposed endoscope 111 having a visual channel 161. Also shown in cross-section in FIG. 29 are portions of the sheath 103 through which electrical connections 109 and an inflation line 113 can pass. These features may be imbedded into the sheath 103 inner wall or attached to the sheath 103 inner wall. As shown in FIG. 27, the sheath 103 including a transmissive portion 158 can extend past the endoscope distal tip 110. Alternatively, as shown in FIGS. 27, 28, and 31, the endoscope distal end 110 can extend distally past the transmissive portion 158 of the sheath 103.

In another implementation, the transmissive portion 158 of the sheath 103 can be reinforced structurally with coil or braid elements incorporated therein to prevent ovalization and/or collapsing of the sheath 103, particularly while deflecting the ablation device 100

Figure 32:
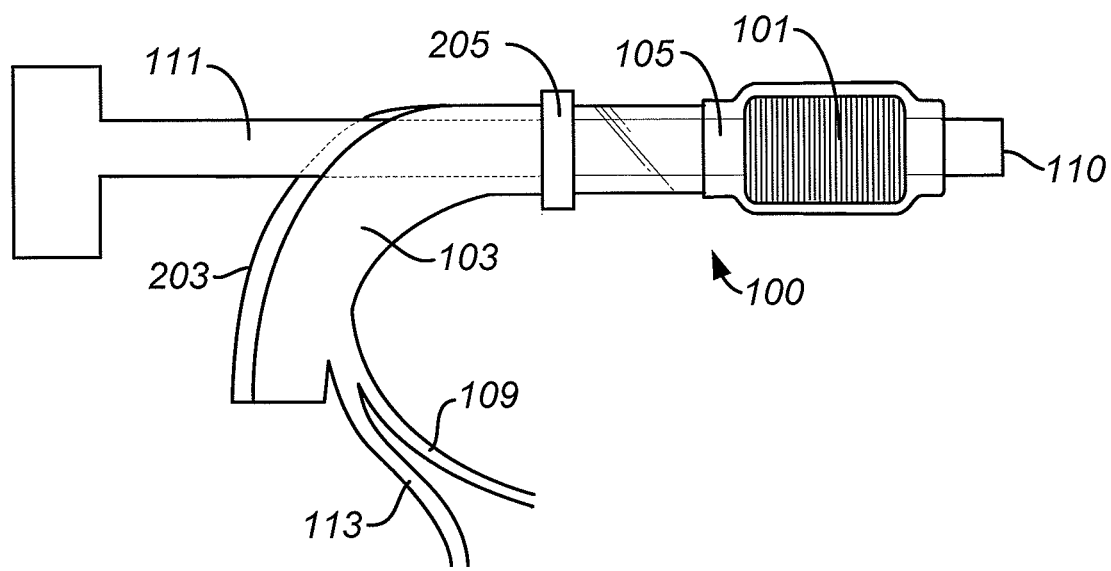
FIG. 32 is a view of the ablation device of the invention including a slit sheath feature.

In a further embodiment, the sheath 103 includes a slit 203 formed in a proximal portion of the sheath 103, the slit 203 being designed to open to admit an endoscope distal end 110 into the sheath 103. As shown in FIG. 32 the proximal portion of the sheath 103 can include a perforation region or slit 203. The slit 203 can extend partially of fully along the length of the sheath 103. The slit 203 enables the sheath 103 to be pulled back, or opened when, for example introducing an endoscope 111 into the sheath 103. In one implementation, as shown in FIG. 32, the sheath 103 additionally includes a locking collar 205 for locking the sheath 103 in a desired position in respect to the endoscope 111.

Figure 33A:
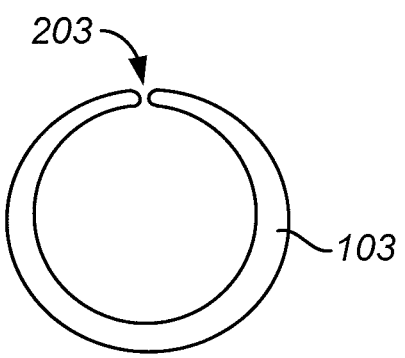
FIG. 33A is an end view of a slit sheath feature of the device wherein the sheath is in an unexpanded configuration.
Figure 33B:
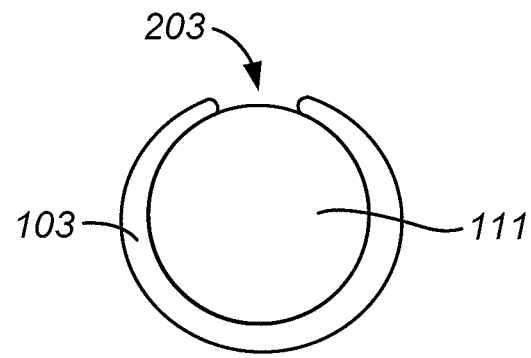
FIG. 33B is an end view of a slit sheath feature of the device and an endoscope wherein the sheath is in an expanded configuration.

As shown in FIGS. 33A and 33B, the distal portion of the sheath 103 can have a smaller outer diameter than a, proximal portion of the sheath 103, the distal portion of the sheath 103 being adapted and configured to be expanded when an endoscope 111 is inserted into it (not shown). This embodiment can aid in accessing an endoscope 111 in a case where the sheath 103 is advanced first into a target site within the alimentary tract. Since the distal end of the sheath 103 is smaller in diameter, but includes a slit 203, the sheath 103 can accept a larger outside diameter endoscope 111 because when the endoscope 111 is advanced, the slit 203 of the sheath 103 allows for widening of the sheath 103.

In general, in another aspect, a method of ablating tissue in within the alimentary tract includes advancing an ablation structure 101 into the alimentary tract while supporting the ablation structure 101 with an endoscope 111. The endoscope distal end 110 can be bent to move the ablation structure 101 into contact with a tissue surface followed by activation of the ablation structure 101 to ablate the tissue surface 3 (see e.g., FIG. 43). In a particular embodiment, the ablation structure 101 includes a plurality of electrodes and the activating step includes applying energy to the electrodes.

In general, in another aspect the coupling mechanism is designed to fit over an outside surface of an endoscope 111, to couple the ablation structure 101 with the endoscope 111, rather than being for example, a sheath (as discussed above), and is adapted and configured to provide a certain freedom of movement to the ablation structure 101, including but not limited to flexing and/or rotating and/or pivoting with respect to the endoscope 111 when coupled to the endoscope 111. The freedom of movement is with respect to one, two, or three axes, thereby providing one, two, or three degrees of freedom. Non-limiting examples of suitable coupling mechanisms include a flex joint, pin joint, U-joint, ball joint, or any combination thereof. The following described coupling mechanism embodiments advantageously provide for a substantially uniform apposition force between a supporting endoscope 111 and an ablation structure 101 when localized at a target tissue surface 3.

Figure 43:
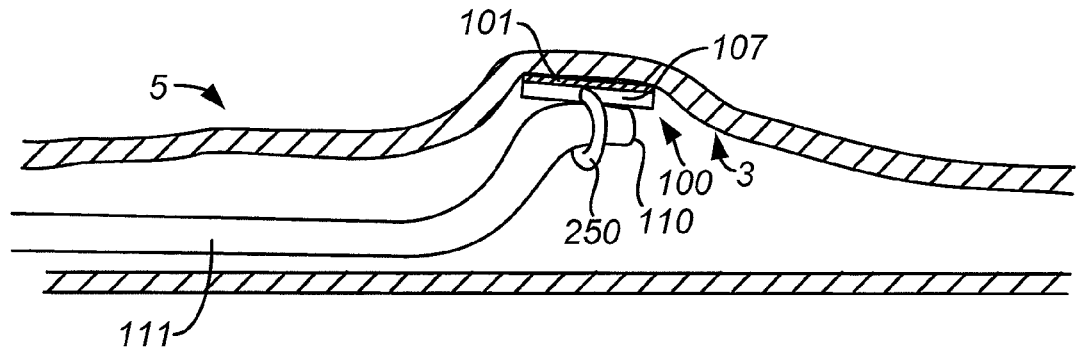
FIG. 43 is an illustration of the ablation device of the invention positioned within an esophagus showing a rotational feature.

As shown in FIGS. 43, 44, 45A, and 45B, the coupling mechanism can be a ring 250 attached to the housing 107 and the endoscope 111, wherein the housing 107 is adapted and configured to flex, rotate or pivot about the ring 250. For example, as illustrated in FIG. 43 (see detailed view in FIG. 38B), where the ablation device 100 is coupled to a deflectable distal end 110 of an endoscope 111 by a ring 250, when the device 100 is deflected toward the tissue surface 3 of the wall of the lumen of a gastrointestinal organ, the housing 107 upon contact aligns the ablation structure 101 with the tissue surface 3 by flexing, rotating or pivoting about the ring 250 coupling. In these embodiments, the endoscope and the housing that supports the ablation structure both have their own longitudinal axis, and these axes are situated parallel to each other. The coupling mechanism that attaches the housing to the endoscope allows a pivoting movement between the longitudinal axis of the housing and the longitudinal axis of the endoscope. Advantageously, sufficient contact pressure provided by deflection of the distal end 110 of the endoscope 101 can produce a desired degree of contact between the ablation structure 101 and the tissue surface 3, irrespective of the precise alignment of the distal end 112 in respect to a plane of the tissue surface 3 to be treated. For the purposes of this disclosure, a "desired degree of contact", "desired contact", "therapeutic contact", or "therapeutically effective contact" between the ablation structure 101 and the tissue surface 3, includes complete or substantially-complete contact between all or a portion of a predetermined target on the tissue surface 3 (e.g. a site on the wall of a luminal organ of the gastrointestinal tract) by all or a portion of the ablation structure 101.

As shown in FIG. 44, in a different yet related embodiment, where the deflection mechanism of the ablation device 100 is an inflatable member 105, a ring 250 coupling allows for flexing, rotating or pivoting of the housing 107 and ablation structure 101. As in the previous case, sufficient contact pressure provided through deflection, here by the inflatable member 105, can produce a desired degree of contact between the ablation structure 101 and the tissue surface 3. Again, advantageously, the desired contact can be achieved irrespective of the precise alignment of the deflected endoscope 111 distal end 110 in respect to a plane of the tissue surface 3 to be treated, because of the flexing, rotating or pivoting provided by the ring 250 coupling.

Figure 45A:
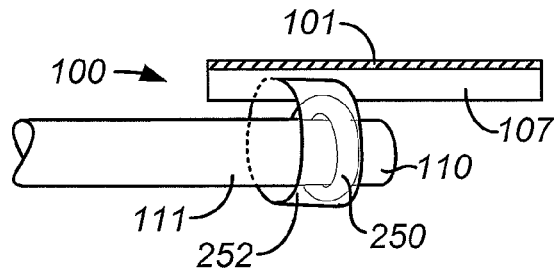
FIGS. 45A-45C are views of the ablation device of the invention showing alternative rotational features.
Figure 45B:
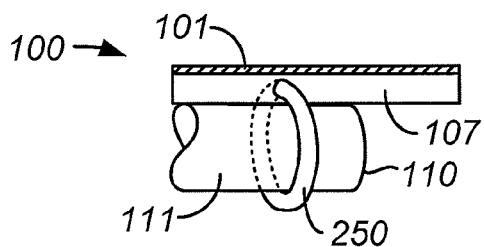
Figure 45C:
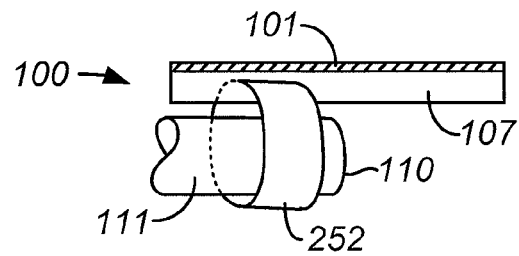

As shown in FIG. 45A, in a related embodiment, the coupling mechanism between the ablation device 100 and an endoscope 111 can be an elastic band 252, wherein the housing 107 of the device 100 is flexibly coupled to the elastic band 252. For example, as illustrated in FIG. 45C, where the ablation device 100 is coupled to a distal end 110 of an endoscope 111 by an elastic band 252, when the device 100 is deflected toward a tissue surface 3 of the wall of a luminal organ of the gastrointestinal tract, alignment between the housing 107 and accordingly the ablation structure 101 and the tissue surface 3, can be achieved by flexing about the elastic band 252 coupling. Once more, advantageously, the desired contact can be achieved irrespective of the precise alignment of the deflected endoscope's 111 distal end 110 in respect to a plane of the tissue surface 3 to be treated, because of the flexing capability provided by the elastic band 252 coupling.

As shown in FIG. 45A, in another related embodiment, the coupling mechanism between the ablation device 100 and an endoscope 111 can be a combination of a ring 250 and an elastic band 252, wherein the housing 107 of the device 100 is coupled to the elastic band 252. For example, as illustrated in FIG. 45A, where the ablation device 100 is coupled to a distal end 110 of an endoscope 111 by an elastic band 252, when the device 100 is deflected toward a tissue surface 3 of, for example, the wall of a luminal organ of the gastrointestinal tract (not shown), alignment between the housing 107 and accordingly the ablation structure 101, and the tissue surface 3 by flexing, rotating or pivoting about the ring 250 and the elastic band 252 coupling can be achieved. Again, advantageously, the desired contact can be achieved irrespective of the precise alignment of the deflected endoscope 111 distal end 110 in respect to a plane of the tissue surface 3 to be treated, because of the flexing rotating or pivoting provided by the elastic band 252 coupling.

In another embodiment, the ablation device 100 additionally includes an alternative coupling mechanism between the ablation device 100 and an endoscope 111 that is arranged and configured to fit within a channel of an endoscope 111. The coupling mechanism can be an internal coupling mechanism 215 and can be configured and arranged to couple the ablation structure 101 within an internal working channel 211 of an endoscope 111 (see FIG. 37 and as discussed above).

As shown in FIGS. 34A, 34B, 35A, 35B, 36A, and 36B, in one embodiment of such a coupling mechanism, the ablation structure 101 is adapted and configured to fit within the endoscope internal working channel 211. Additionally, as shown in FIGS. 34A, 34B, 35A, 35B, 36A, and 36B, in a related embodiment, the deflection mechanism is also adapted and configured to fit within the endoscope internal working channel 211.

In each of the embodiments described above and shown in FIGS. 34A, 34B, 35A, 35B, 36A, and 36B, after expansion of the inflatable member 105 or expandable member 209 and subsequent treatment of a target tissue 3, the coupling means can further serve as a means to draw, pull or retrieve the ablation structure 101 and deflection mechanism back into the endoscope internal working channel 211. Furthermore, in addition to providing coupling of the ablation structure 101 with the endoscope internal working channel 112, the coupling mechanism can include electrical connections 109 to provide energy to the ablation structure 101.

In a related embodiment, again wherein the ablation device 100 additionally includes a coupling mechanism adapted and configured to fit within a channel of an endoscope 111, the coupling mechanism can include a shape memory member and the deflection mechanism can include a bent portion of the shape memory member. As shown in FIGS. 37-39, the coupling mechanism can be an internal coupling mechanism 215. As shown, the internal coupling mechanism 215 can be disposed within an endoscope internal working channel 211 and extend beyond the endoscope distal end 100. Additionally, the internal coupling mechanism 215 can be connected to a deflection mechanism that is a deflection member 150. The deflection member 150 can include a bent portion and can be connected to the housing 107. As shown in FIG. 38 and discussed above, the bent portion of the deflection member 150 can be disposed within the endoscope internal working channel 211, causing the ablation structure 101 to move into a non-deployed position. Upon advancing the internal coupling mechanism 215 toward the endoscope distal end 110, the shape memory nature of the deflection member 150 facilitates deployment of the ablation structure 101 to a position suitable for ablation.

In general, in one aspect, the ablation structure 101 of the ablation device 100 includes an optically transmissive portion 158 adapted and configured to cooperate with a visual channel of an endoscope 111. As shown in FIGS. 27-31 and discussed above, the optically transmissive portion 158 can be a sheath 103 of the ablation device 100.

In one embodiment, the ablation structure 101 of the ablation device 100 is further adapted and configured to move from a first configuration to a second radially expanded configuration. As shown in FIGS. 19-22, the ablation structure 101 and housing 107 can be designed to reversibly move from a first less radially expanded configuration (see FIGS. 20 and 21) to a second radially expanded configuration useful for ablation. Foldable or deflectable configurations that provide for reversible radial expansion of the housing 107 and the ablation structure 101 can facilitate access to tissue surfaces because of reduced size. Additionally, foldable or deflectable configurations are helpful in regard to cleaning, introduction, retrieval, and repositioning of the device in the luminal organs of the gastrointestinal tract.

Figure 20:
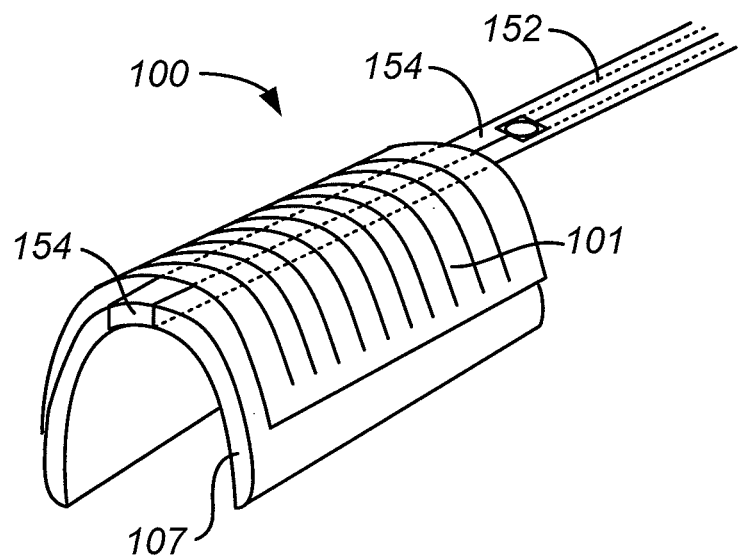
FIG. 20 is a view of device shown in FIG. 19 wherein the deflection member is in an unexpanded configuration.
Figure 21:
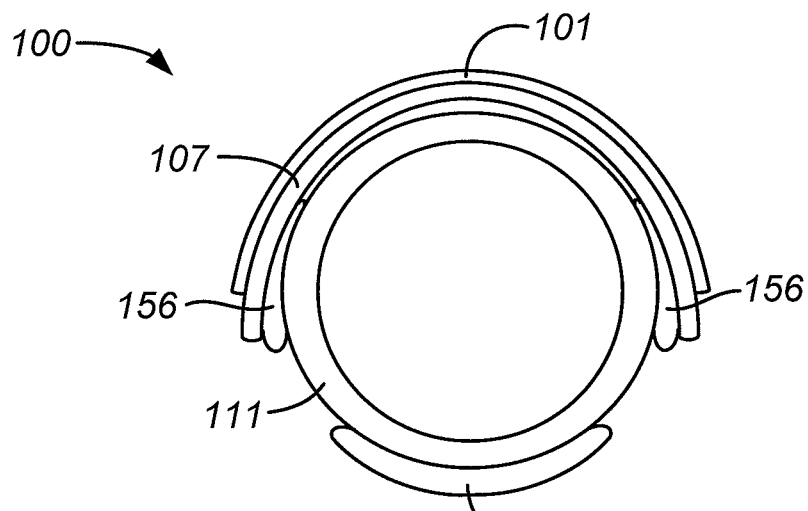
FIG. 21 is an end view of the device in an unexpanded configuration.

The ablation device 100 shown in FIGS. 19 and 20 includes an ablation structure actuator 152 arranged and configured to move the ablation structure 101 from the first configuration (see FIG. 20) to a second radially-expanded configuration (see FIG. 21). As shown in FIGS. 19 and 20, the actuator 152 can be elongate and designed to work with a receiver 154 arranged and configured to receive the actuator 152. The actuator 152 can be a wire, rod or other suitable elongate structure. Alternatively, the actuator 152 can be a hydraulic actuation means with or without a balloon component. In a particular embodiment, the actuator 152 is a stiffening wire.

As illustrated in FIG. 20, before the actuator 152 is disposed within the portion of receiver 154 attached to the housing 107, both the housing 107 and the ablation structure 101 are in a first position having a first configuration. As illustrated in FIG. 21, after the actuator 152 is partially or fully introduced into the receiver 154, the housing 107 and the ablation structure 101 are consequently changed to a second radially expanded configuration relative to the first configuration. Introduction of the actuator 152 into the receiver 154 can force the portions of the housing 107 and ablation structure 101 flanking the receiver 154 to expand radially (see FIG. 19). In one embodiment, the housing 107 is heat set in a flexed first configuration suitable for positioning the ablation device 100 near a target tissue surface 3. After a target tissue surface 3 has been reached, the actuator 152 can be introduced into the receiver 154 to achieve the second radially expanded configuration which is useful for ablation of the tissue surface 3.

In a related alternative embodiment, the housing 107 and ablation structure 101 include an unconstrained shape that is radially expanded and includes one or more flex points to allow for collapsed or reduced radial expansion when positioned distally to the distal end 110 of an endoscope 111 and compressed by an elastomeric sheath 115 (not shown).

Figure 22:
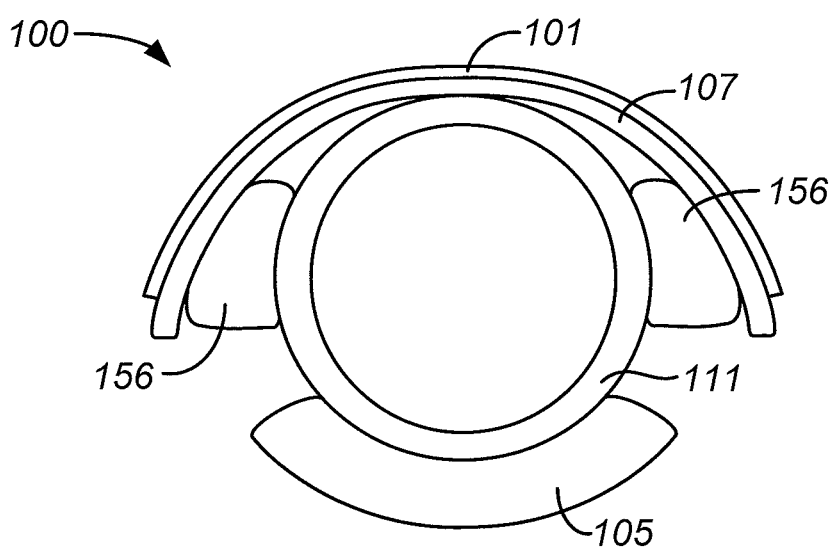
FIG. 22 is an end view of the device shown in FIG. 21 in an expanded configuration.

As shown in FIGS. 21 and 22, in another embodiment, the ablation structure 101 of the ablation device 100 is adapted and configured to move from a first configuration to a second radially expanded configuration wherein the ablation device 100 further includes an expandable member 156. As illustrated in FIG. 19, the expandable member 156 can be positioned between the housing 107 and the endoscope 111, where in unexpanded form, the ablation structure 101 is accordingly configured in a first configuration. Upon expansion of the expandable member 156, the ablation structure 101 configuration is changed to a second radially expanded configuration (see FIG. 20).

In one embodiment, the deflection mechanism of the ablation device 100 includes an inflatable inflation member 105. As shown in FIGS. 11, 21, 22, 25B, 27, 28, 30, 31, 34A, 34B, 42, 44, 46, and 47 and discussed above, the inflation member 105 can facilitate deflection of the device 100 in relation to a tissue surface 3.

In another embodiment, the deflection mechanism includes an expandable member 156 (see FIGS. 35B and 36B, discussed in detail above). As shown in FIG. 35B, the expandable member 209, can be an expandable stent, frame or cage device. As shown in FIG. 36B, the expandable member 209, can be an expanded series of connected hoops that can be folded or rolled prior to expansion.

Figure 46C:
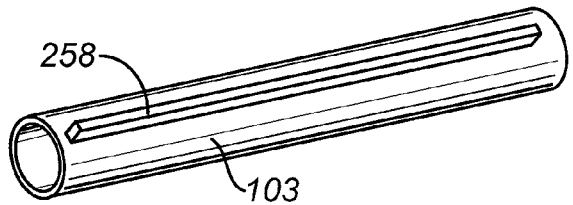
FIG. 46C is a view of a sheath feature of the device.

In another advantageous embodiment, the ablation device 100 further comprises a torque transmission member adapted and configured to transmit torque from a proximal end of the endoscope 111 to the ablation structure 101 to rotate the ablation structure 101 about a central axis of the endoscope 111. In a particular embodiment, the torque transmission member includes first and second interlocking members adapted to resist relative movement between the endoscope 111 and the ablation structure 101 about the central axis. As shown in FIGS. 46 and 47, in one embodiment the first interlocking member is a key 258 and the second interlocking member is a keyway 256. In one embodiment, the first interlocking member is attached to a sheath 103 surrounding the endoscope 111 and the second interlocking member is attached to a catheter 254 supporting the ablation structure 101. For example, as shown in FIGS. 46B, 46C, and 47, the key 258 can be attached to a sheath 103 surrounding the endoscope 111 and the keyway 256 can be attached to a catheter 254 supporting the ablation structure 101. In a further related embodiment, the catheter 254 and sheath 103 are arranged and configured for relative movement along the central axis of the endoscope 111. The sheath 103 can be, for example, an elastomeric sheath wherein the key 258 is attached to the outside of the sheath 103 substantially along a longitudinal axis of the sheath 103 (see FIG. 46C). In use, this embodiment provides for a 1-to-1 torque transmission of the ablation device 100 endoscope assembly 111 when the endoscope proximal end 112 is manipulated, while also providing for positioning of the ablation structure 101 either proximal or distal to the endoscope distal end 110 in situ. Additionally, the sheath 103 can be pre-loaded into the catheter 254 or loaded separately.

In general, in one aspect, an ablation device 100 is provided including an ablation structure 101, and a coupling mechanism adapted to removably couple the ablation structure 101 to a distal end 110 of an endoscope 111 and to permit the ablation structure 101 to rotate and/or pivot with respect to the endoscope when coupled to the endoscope. Various related embodiments wherein, for example, the coupling mechanism comprises a ring 250 and the ablation structure 101 is adapted to rotate and/or pivot about the ring 250; wherein the coupling mechanism comprises an elastic band 252 adapted to flex to permit the ablation structure 101 to rotate and/or pivot; wherein the ablation device 100 further includes a deflection mechanism adapted and configured to move the ablation structure 101 toward a tissue surface 3; and, wherein such a deflection mechanism includes an inflatable member, have been set out in detail above.

While most embodiments described herein have made use of radiofrequency energy as an exemplary ablational energy, and consequently have made use of electrodes as an energy transmitting element, it should be understood that these examples are not limiting with regard to energy source and energy delivery or transmitting elements. As also described herein, other forms of energy, as well as cryoablating approaches, may provide for ablation of target areas in such a manner that ablation is fractional or partial, as described herein, where some portions of target area tissue are ablated, and some portions of target area tissue are not substantially ablated.

Terms and Conventions

Unless defined otherwise, all technical terms used herein have the same meanings as commonly understood by one of ordinary skill in the art of ablational technologies and treatment for metabolic conditions and diseases such as obesity, metabolic syndrome, and diabetes mellitus. Specific methods, devices, and materials are described in this application, but any methods and materials similar or equivalent to those described herein can be used in the practice of the present invention. While embodiments of the invention have been described in some detail and by way of exemplary illustrations, such illustration is for purposes of clarity of understanding only, and is not intended to be limiting. Various terms have been used in the description to convey an understanding of the invention; it will be understood that the meaning of these various terms extends to common linguistic or grammatical variations or forms thereof. It will also be understood that when terminology referring to devices, equipment, or drugs that have been referred to by trade names, brand names, or common names, that these terms or names are provided as contemporary examples, and the invention is not limited by such literal scope. Terminology that is introduced at a later date that may be reasonably understood as a derivative of a contemporary term or designating of a hierarchal subset embraced by a contemporary term will be understood as having been described by the now contemporary terminology. Further, while some theoretical considerations have been advanced in furtherance of providing an understanding of, for example, the biology of metabolic disease, or the mechanisms of action of therapeutic ablation, the claims to the invention are not bound by such theory. Moreover, any one or more features of any embodiment of the invention can be combined with any one or more other features of any other embodiment of the invention, without departing from the scope of the invention. Still further, it should be understood that the invention is not limited to the embodiments that have been set forth for purposes of exemplification, but is to be defined only by a fair reading of claims that are appended to the patent application, including the full range of equivalency to which each element thereof is entitled.

What is claimed is:

1. A method of ablationally-treating tissue at a target area in a gastrointestinal tract of a patient with a pathophysiological metabolic condition comprising:
   delivering energy from an ablation structure to a tissue surface within the target area, the target area being a portion of the gastrointestinal tract that includes at least a portion of a jejunum; and
   controlling the delivery of energy to the tissue surface within the target area and into a depth of tissue within the target area to treat the pathophysiological metabolic condition.

2. The method of claim 1 wherein controlling the delivery of energy into depth of the tissue includes controlling the delivery of energy inwardly from the tissue surface such that sufficient energy to achieve ablation is delivered to some layers and insufficient energy is delivered to other layers to achieve ablation.

3. The method of claim 1 wherein controlling the delivery of energy to the tissue surface within the target area includes delivering sufficient energy to achieve ablation in one portion of the tissue target area to achieve ablation and delivering insufficient energy to another portion of the surface to achieve ablation.

4. The method of claim 3 wherein delivering sufficient energy to achieve ablation includes configuring an electrode pattern such that some spacing between electrodes is sufficiently close to allow conveyance of a level of energy sufficient to ablate and other spacing between electrodes is insufficiently close to allow conveyance of the level of energy sufficient to ablate.

5. The method of claim 3 wherein delivering sufficient energy to achieve ablation includes operating an electrode pattern such that the energy delivered between some electrodes is sufficient to ablate and energy sufficient to ablate is not delivered between some electrodes.

6. The method of claim 1 wherein controlling the delivery of energy into inwardly from the surface of the tissue consists of ablating some portion of tissue within the epithelial layer.

7. The method of claim 1 wherein controlling the delivery of energy into inwardly from the surface of the tissue consists of ablating some portion of tissue within the epithelial layer and the lamina propria.

8. The method of claim 1 wherein controlling the delivery of energy into inwardly from the surface of the tissue consists of ablating some portion of tissue within the epithelial layer, the lamina propria, and the muscularis mucosae.

9. The method of claim 1 wherein controlling the delivery of energy into inwardly from the surface of the tissue consists of ablating some portion of tissue within the epithelial layer, the lamina propria, the muscularis mucosae, and the submucosa.

10. The method of claim 1 wherein controlling the delivery of energy into inwardly from the surface of the tissue consists of ablating some portion of tissue within the epithelial layer, the lamina propria, the muscularis mucosae, the submucosa, and the muscularis propria.

11. The method of claim 1 wherein the pathophysiological metabolic condition includes any one or more of type 2 diabetes, insulin resistance, obesity, or metabolic syndrome.

12. The method of claim 1 further comprising restoring the pathophysiological metabolic condition of the patient toward a normal metabolic condition.

13. The method of claim 12 wherein restoring the metabolic condition toward a normal metabolic condition includes any of decreasing blood glucose levels, decreasing blood insulin levels, decreasing insulin resistance, decreasing body weight, or decreasing body mass index.

14. The method of claim 1 wherein the ablation target area includes cells that support the secretion of insulin in the patient, and wherein upon receiving transmitted energy from the ablation structure are rendered at least partially dysfunctional.

15. The method of claim 14 wherein the cells supporting the effect of insulin are endocrine cells.

16. The method of claim 14 wherein the cells supporting the effect of insulin are nerve cells.

17. The method of claim 1 wherein the ablation target area includes cells that support the response of the patient to insulin, and wherein upon receiving transmitted energy from the ablation structure are rendered at least partially dysfunctional.

18. The method of claim 17 wherein supporting the response to insulin includes any of promoting the greater effectiveness of secreted insulin or decreasing the effect of agents that have an anti-insulin effect.

19. The method of claim 17 wherein the cells supporting the effect of insulin are endocrine cells.

20. The method of claim 17 wherein the cells supporting the effect of insulin are nerve cells.

21. The method of claim 1 wherein the target area is located in the gastric antrum.

22. The method of claim 1 wherein the target area is located in the pylorus.

23. The method of claim 1 wherein controlling the delivery of energy across the tissue surface within the target area and into the depth of tissue within the target area allows achievement of a partial ablation in tissue layers of the gastrointestinal tract.

24. The method of claim 23 wherein the target area is in the epithelial layer of the gastric antrum.

25. The method of claim 23 wherein the target area is in epithelial layer of the any of the duodenum or jejunum.

26. The method of claim 23 wherein partial ablation in the epithelial layer slows the rate of nutrient absorption through the epithelial layer.

27. The method of claim 23 wherein the target area includes the muscularis of the gastric antrum causing a slowing of gastric emptying.

28. The method of claim 23 wherein the target area includes the muscularis of the pyloris causing a slowing of gastric emptying.

29. The method of claim 23 wherein the target area includes the muscularis of the duodenum causing a slowing of gastric emptying.

30. The method of claim 1 wherein the ablation has a permanent effect on the function of the target area.

31. The method of claim 1 wherein the ablation has a transient effect on the function of the target area.

32. The method of claim 31 wherein the transient effect has duration that ranges from a period of about one day to about one year.

33. The method of claim 31 wherein during the time when the function of the target region is transiently affected, the method further includes evaluating the patient for a beneficial therapeutic effect of the ablation.

34. The method of claim 33 wherein in the event of a beneficial therapeutic effect, the method further includes repeating the ablation of the target region.

35. The method of claim 34 wherein the repeated ablation is a transient ablation.

36. The method of claim 34 wherein the repeated ablation is a permanent ablation.

37. The method of claim 1 wherein the electrode pattern is configured circumferentially through 360 degrees around the ablation structure.

38. The method of claim 37 wherein transmitting energy from the ablation structure includes transmitting energy asymmetrically through the 360 degree circumference such that ablation is focused within an arc of less than 360 degrees.

39. The method of claim 1 wherein the electrode pattern is configured circumferentially through an arc of less than 360 degrees around the ablation structure.

40. The method of claim 1 further comprising evaluating the target area at a point in time after the delivering energy step to determine the status of the area.

41. The method of claim 40 wherein the evaluating step occurs in close time proximity after the delivery of energy, to evaluate the immediate post-treatment status of the site.

42. The method of claim 40 wherein the evaluating step occurs at least one day after the delivery of energy.

43. The method of claim 1 wherein the delivering energy step is performed more than once.

44. The method of claim 1 further compromising deriving energy for transmitting from an energy source that is controlled by a control system.

45. The method of claim 44 wherein the energy source is a generator.

46. The method of claim 44 further comprising feedback controlling the energy transmission so as to provide any of a specific power, power density, energy, energy density, circuit impedance, or tissue temperature.

47. The method of claim 1 wherein the energy comprises at least radiofrequency energy or steam heat.

48. The method of claim 1 wherein, the target area being a portion of the gastrointestinal tract that includes at least a portion of a duodenum.

* * * * *